United States Patent
Xiong et al.

(10) Patent No.: US 11,535,613 B2
(45) Date of Patent: Dec. 27, 2022

(54) CRYSTAL FORM AND SALT FORM OF PYRIDOIMIDAZOLE COMPOUND AND PREPARATION METHOD THEREFOR

(71) Applicant: GUANGDONG RAYNOVENT BIOTECH CO., LTD., Guangdong (CN)

(72) Inventors: Jian Xiong, Shanghai (CN); Xiaoxin Chen, Shanghai (CN); Jingjing Wang, Shanghai (CN); Zhuowei Liu, Shanghai (CN); Kevin X Chen, Shanghai (CN); Chengwu Liu, Shanghai (CN); Cheng Xie, Shanghai (CN); Chaofeng Long, Shanghai (CN); Peng Li, Shanghai (CN); Jian Li, Shanghai (CN); Shuhui Chen, Shanghai (CN)

(73) Assignee: GUANGDONG RAYNOVENT BIOTECH CO., LTD., Guangdong (CN)

( * ) Notice: Subject to any disclaimer, the term of this patent is extended or adjusted under 35 U.S.C. 154(b) by 260 days.

(21) Appl. No.: 16/975,600

(22) PCT Filed: Mar. 5, 2019

(86) PCT No.: PCT/CN2019/076916
§ 371 (c)(1),
(2) Date: Aug. 25, 2020

(87) PCT Pub. No.: WO2019/170067
PCT Pub. Date: Sep. 12, 2019

(65) Prior Publication Data
US 2020/0407354 A1    Dec. 31, 2020

(30) Foreign Application Priority Data

Mar. 5, 2018 (CN) .......................... 201810180641.8

(51) Int. Cl.
*C07D 471/04* (2006.01)
*A61K 31/506* (2006.01)
*A61P 31/16* (2006.01)

(52) U.S. Cl.
CPC .......... *C07D 471/04* (2013.01); *A61K 31/506* (2013.01); *A61P 31/16* (2018.01); *C07B 2200/13* (2013.01)

(58) Field of Classification Search
CPC   C07D 471/04; C07B 2200/13; A61K 31/506; A61P 31/16; C07C 309/30
See application file for complete search history.

(56) References Cited

FOREIGN PATENT DOCUMENTS

| CN | 103492381 A | 1/2014 |
|---|---|---|
| CN | 104922128 A | 9/2015 |
| CN | 106573920 A | 4/2017 |
| WO | 2017097234 A1 | 6/2017 |
| WO | 2017133670 A1 | 8/2017 |
| WO | 201841263 A1 | 3/2018 |

*Primary Examiner* — Scarlett Y Goon
*Assistant Examiner* — Eric Tran
(74) *Attorney, Agent, or Firm* — D'Ambrosio & Menon, PLLC; Usha Menon

(57) ABSTRACT

Disclosed are a crystal form and a salt form of a pyrazolo-pridine compound, and a preparation method therefor. Further included is the use of the crystal form in preparing anti-influenza virus drugs.

25 Claims, 18 Drawing Sheets

Fig. 11
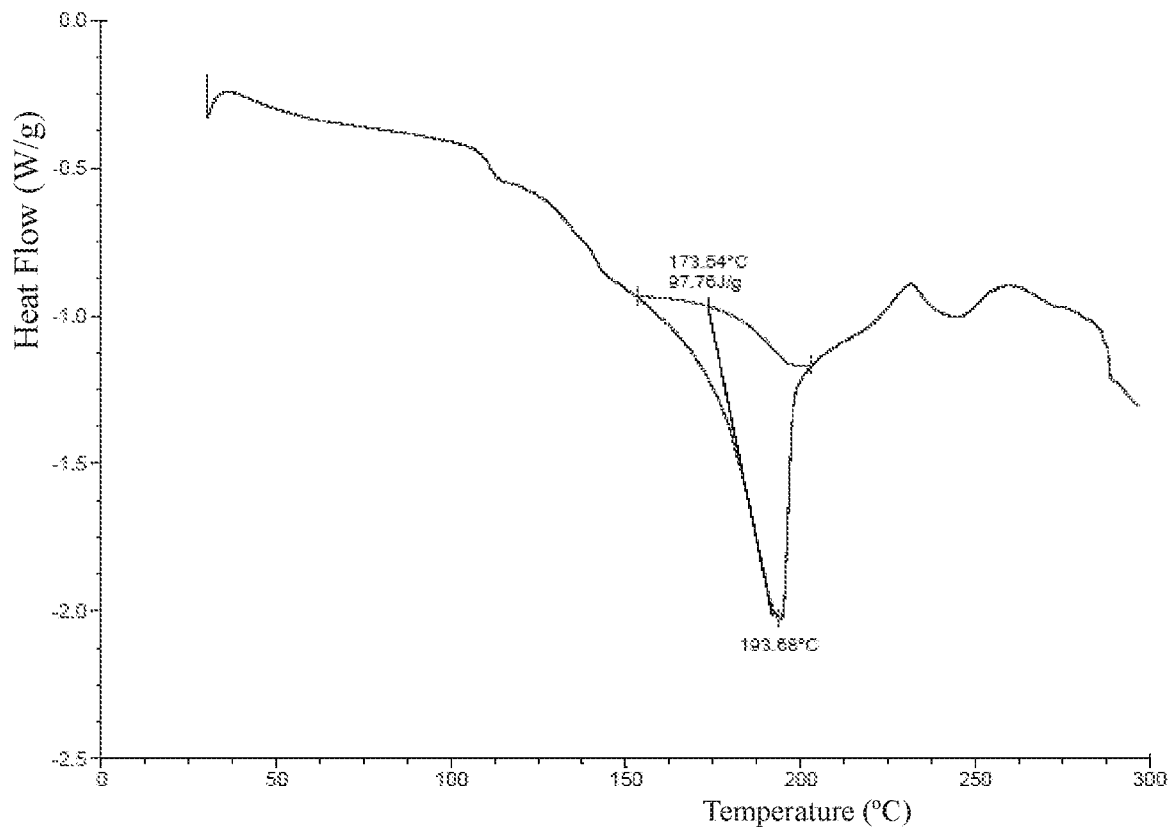
Fi.g 12
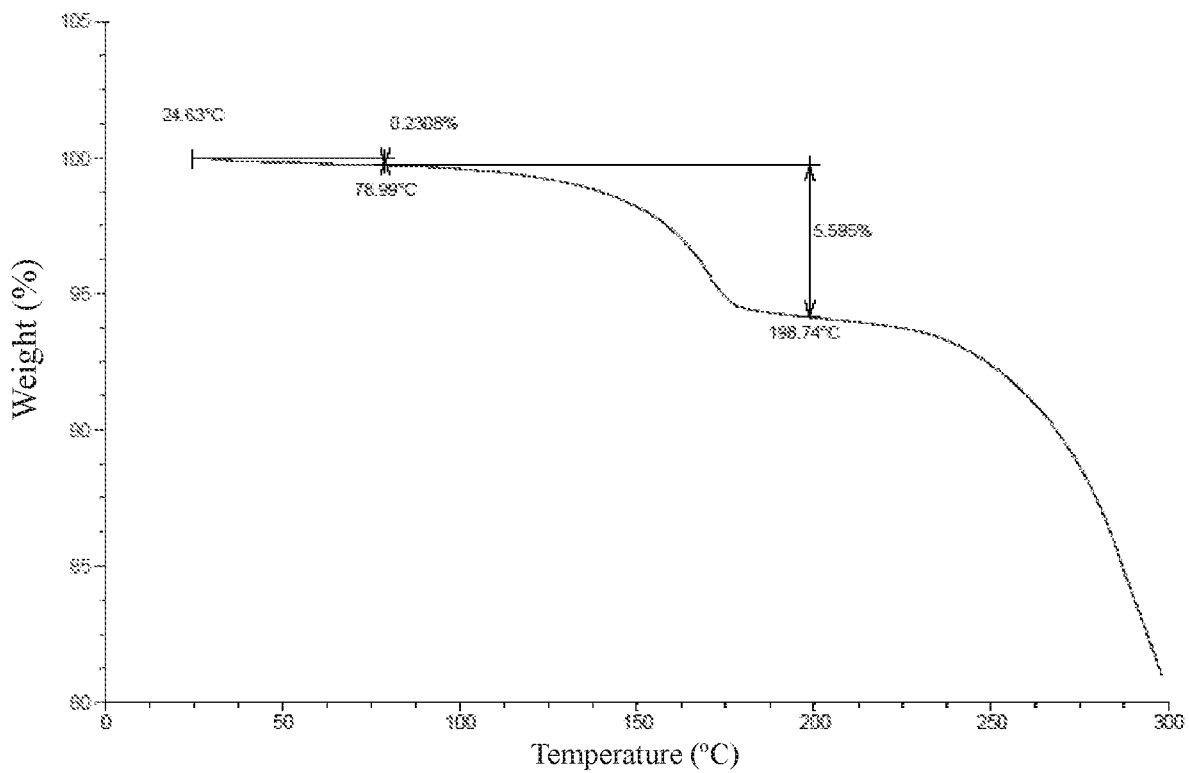

CRYSTAL FORM AND SALT FORM OF PYRIDOIMIDAZOLE COMPOUND AND PREPARATION METHOD THEREFOR

CROSS-REFERENCE TO RELATED APPLICATIONS

The present application claims the priority of CN201810180641.8 filed on Mar. 5, 2018.

TECHNICAL FIELD

The present disclosure relates to crystal- and salt forms of a pyridoimidazole-based compound and preparation methods thereof, and relates to use of the crystal forms in preparation of a medicament against influenza virus-associated diseases.

BACKGROUND

Influenza Virus (IFV) is a segmented single-stranded antisense RNA virus that can cause influenza in humans and animals. The influenza pandemic leads to thousands of deaths, causes great social panic, and increases social instability.

Influenza will cause direct costs of lost productivity and related medical resources and indirect costs of preventive measures. In the United States, influenza has caused an estimated annual loss of about 10 billion US dollars. It is estimated that future influenza pandemics can cause hundreds of billions of dollars in direct and indirect costs. Costs of prevention are also very high. Governments around the world have spent billions of dollars in preparing and planning for a possible H5N1 avian influenza pandemic. The cost is related to the purchase of drugs and vaccines, as well as the development of disaster drills and strategies to improve border control.

Current options for flu treatment include vaccination and chemotherapy and chemoprevention with antiviral drugs. Antiviral drugs can also be used to treat influenza, in which neuraminidase inhibitors, e.g., oseltamivir (Tamiflu), have an obvious effect on influenza A virus. However, after clinical observation, it has been found that virus strains resistant to this type of neuraminidase inhibitors have appeared. In the field of anti-influenza viruses, anti-influenza virus drugs with a new mechanism of action are in urgent clinical need, which can support the use of a single drug for treatment of influenza A, or can be used in combination with other existing anti-influenza virus drugs with other mechanisms of action for prevention and treatment of influenza A.

SUMMARY

To solve the shortcomings of the prior art, the present disclosure provides a pyridoimidazole compound and its salt forms, corresponding crystal forms, and preparation methods thereof, thereby providing a plurality of raw material options for developing the pyridoimidazole compound and its salt forms as a clinical drug.

For characterization of a crystal form of a compound, persons skilled in the art can understand that for a specific crystal form of a specific compound, 2θ angles of various diffraction peaks in its X-ray powder diffraction pattern (XRPD) would have some fluctuations in repeated experiments due to the influence of instrument(s), operation method, sample purity, human factors and the like during the characterization process, and the fluctuation range (error range) is usually within ±0.2°. In addition, persons skilled in the art can also understand that the stability and repeatability of diffraction peaks would be affected by a combination of factors like 2θ angle, absorption intensity (peak height) of various diffraction peaks of the X-ray powder diffraction pattern, etc. In particular, the stronger the absorption intensity, the better the separation, and the smaller the 2θ angle, the better the stability and repeatability of the diffraction peak, and the more it can be used to characterize the specific crystal form. In contrast, diffraction peaks with larger 2θ angle and/or poorer separation and/or weaker relative intensity may be subject to relatively larger fluctuations due to the influence of instrument(s), operation method, sample purity, human factors and the like, or cannot be repeated in repeated experiments. Therefore, for those skilled in the art, such absorption peaks are not necessary diffraction peaks for characterizing the crystal form; more specifically, the present disclosure comprehensively considers factors such as 2θ angle, absorption intensity (peak height) and the like when selecting peaks, and groups them according to the stability and repeatability.

Persons skilled in the art can understand that there may be little or no difference in certain physical characteristics between different hydrates, solvates, and anhydrates of a certain compound. Specially, for the series of the compounds of the present disclosure, different hydrates, solvates, and anhydrates of the same salt form tend to have the same XRPD pattern, while the differences lie in the different DSC and/or TGA patterns thereof.

The first object of the present disclosure is to provide a series of crystal forms of the compound of Formula (I), wherein n is selected from 0, 0.5, 1, 1.5, 2, 2.5, 3, 3.5 and 4.

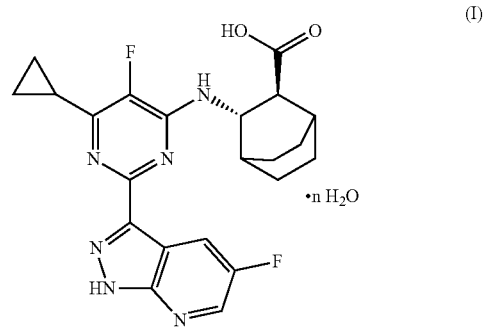 [SMILES: O=C(O)[C@H]1C2CCC(CC2)[C@@H]1Nc1nc(-c2n[nH]c3ncc(F)cc23)nc(C2CC2)c1F]

In particular, the crystal form A of the compound of Formula (I) has an X-ray powder diffraction pattern with characteristic diffraction peaks at 2θ angles of 6.61±0.2°, 9.27±0.2°, 14.66±0.2°; and further, the aforesaid crystal form A of the compound of Formula (I) has an X-ray powder diffraction pattern with characteristic diffraction peaks at 2θ angles of 6.61±0.2°, 9.27±0.2°, 14.66±0.2°, 16.69±0.2°, 18.65±0.2°, 19.79±0.2°, 21.85±0.2°, 24.63±0.2°.

In some embodiments of the present disclosure, the aforesaid crystal form A of the compound of Formula (I) may have XRPD analysis data as shown in Table 1. Persons skilled in the art can understand that as compared with the high volatility of the peak height, the 2θ value in the XRPD analysis data is more suitable for characterization of the crystal form due to its smaller volatility.

TABLE 1

XRPD analysis data of the crystal form A of the compound of Formula (I)

| No. | 2θ (±0.2°) | d (Å) | Background | Peak Height | Peak Height % | Area | Area % | Full Width at Half Maximum |
|---|---|---|---|---|---|---|---|---|
| 1 | 4.693 | 18.8155 | 487 | 401 | 2.3 | 4406 | 1.6 | 0.184 |
| 2 | 6.606 | 13.3686 | 382 | 17701 | 100 | 274152 | 100 | 0.26 |
| 3 | 7.371 | 11.9829 | 270 | 292 | 1.6 | 5378 | 2 | 0.309 |
| 4 | 9.272 | 9.5302 | 297 | 6379 | 36 | 93083 | 34 | 0.245 |
| 5 | 10.396 | 8.502 | 285 | 452 | 2.6 | 4594 | 1.7 | 0.171 |
| 6 | 14.66 | 6.0375 | 195 | 2566 | 14.5 | 38107 | 13.9 | 0.249 |
| 7 | 16.219 | 5.4605 | 203 | 450 | 2.5 | 7443 | 2.7 | 0.278 |
| 8 | 16.693 | 5.3063 | 213 | 1024 | 5.8 | 14014 | 5.1 | 0.23 |
| 9 | 17.502 | 5.063 | 208 | 552 | 3.1 | 7322 | 2.7 | 0.223 |
| 10 | 18.648 | 4.7544 | 219 | 831 | 4.7 | 13733 | 5 | 0.277 |
| 11 | 19.099 | 4.643 | 241 | 110 | 0.6 | 1006 | 0.4 | 0.153 |
| 12 | 19.793 | 4.4819 | 241 | 1962 | 11.1 | 28579 | 10.4 | 0.244 |
| 13 | 20.683 | 4.2909 | 220 | 479 | 2.7 | 5671 | 2.1 | 0.199 |
| 14 | 21.846 | 4.065 | 220 | 1545 | 8.7 | 23200 | 8.5 | 0.252 |
| 15 | 22.814 | 3.8947 | 254 | 252 | 1.4 | 5199 | 1.9 | 0.346 |
| 16 | 23.188 | 3.8327 | 214 | 560 | 3.2 | 15747 | 5.7 | 0.472 |
| 17 | 23.642 | 3.7601 | 222 | 670 | 3.8 | 9331 | 3.4 | 0.234 |
| 18 | 24.631 | 3.6114 | 231 | 722 | 4.1 | 13690 | 5 | 0.318 |
| 19 | 24.964 | 3.5639 | 208 | 339 | 1.9 | 14993 | 5.5 | 0.742 |
| 20 | 25.516 | 3.488 | 253 | 277 | 1.6 | 2981 | 1.1 | 0.181 |
| 21 | 26.385 | 3.3751 | 224 | 710 | 4 | 10695 | 3.9 | 0.253 |
| 22 | 27.138 | 3.2832 | 208 | 437 | 2.5 | 6496 | 2.4 | 0.249 |
| 23 | 27.946 | 3.19 | 184 | 268 | 1.5 | 3658 | 1.3 | 0.229 |
| 24 | 29.426 | 3.0329 | 194 | 175 | 1 | 2584 | 0.9 | 0.248 |
| 25 | 30.236 | 2.9535 | 171 | 343 | 1.9 | 6661 | 2.4 | 0.326 |
| 26 | 31.204 | 2.864 | 160 | 317 | 1.8 | 5911 | 2.2 | 0.313 |
| 27 | 31.675 | 2.8224 | 159 | 131 | 0.7 | 2179 | 0.8 | 0.279 |
| 28 | 33.02 | 2.7105 | 152 | 145 | 0.8 | 2714 | 1 | 0.314 |
| 29 | 33.65 | 2.6612 | 148 | 201 | 1.1 | 3217 | 1.2 | 0.269 |
| 30 | 35.623 | 2.5182 | 143 | 108 | 0.6 | 2882 | 1.1 | 0.448 |
| 31 | 36.259 | 2.4755 | 135 | 101 | 0.6 | 2272 | 0.8 | 0.377 |
| 32 | 38.665 | 2.3268 | 114 | 89 | 0.5 | 1244 | 0.5 | 0.235 |

In some embodiments of the present disclosure, the aforesaid crystal form A of the compound of Formula (I) has an XRPD pattern as shown in FIG. 1.

In some embodiments of the present disclosure, the aforesaid crystal form A of the compound of Formula (I) has a differential scanning calorimetry (DSC) curve with a starting point of an endothermic peak at 185.46° C.±3° C.; and further, in some embodiments of the present disclosure, the crystal form A of the compound of Formula (I) has a DSC pattern as shown in FIG. 2.

In some embodiments of the present disclosure, the aforesaid crystal form A of the compound of Formula (I) has a thermogravimetric analysis curve (TGA) at 120.00° C.±3° C. with a weight loss of 2.479%; and further, in some embodiments of the present disclosure, the crystal form A of the compound of Formula (I) has a TGA pattern as shown in FIG. 3.

In some embodiments of the present disclosure, in the aforesaid crystal form A of the compound of Formula (I), the compound of Formula (I) has a structure as represented by Compound 1:

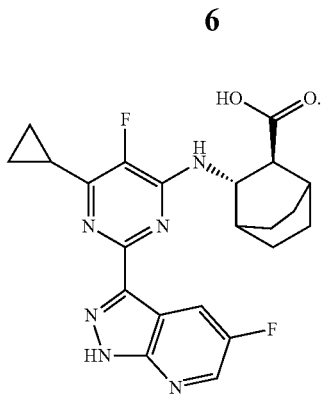

Compound 1

In particular, the crystal form B of the compound of Formula (I) has an X-ray powder diffraction pattern with characteristic diffraction peaks at 2θ angles of 7.14±0.2°, 11.19±0.2°, 22.39±0.2°; and further, the aforesaid crystal form B of the compound of Formula (I) has an X-ray powder diffraction pattern with characteristic diffraction peaks at 2θ angles of 7.14±0.2°, 11.19±0.2°, 12.00±0.2°, 17.28±0.2°, 18.84±0.2°, 22.39±0.2°, 26.90±0.2°, 27.95±0.2°.

In some embodiments of the present disclosure, the aforesaid crystal form B of the compound of Formula (I) may have XRPD analysis data as shown in Table 2. Persons skilled in the art can understand that as compared with the peak height with higher volatility, the 2θ value in XRPD analysis data is more suitable for characterization of the crystal form due to its smaller volatility.

TABLE 2

XRPD analysis data of the crystal form B of the compound of Formula (I)

| No. | 2θ (±0.2°) | d (Å) | Background | Peak Height | Peak Height % | Area | Area % | Full Width at Half Maximum |
|---|---|---|---|---|---|---|---|---|
| 1 | 7.143 | 12.3657 | 290 | 1693 | 31.4 | 24405 | 24.9 | 0.242 |
| 2 | 8.662 | 10.1994 | 231 | 387 | 7.2 | 5418 | 5.5 | 0.235 |
| 3 | 11.192 | 7.8992 | 264 | 3250 | 60.2 | 46337 | 47.3 | 0.239 |
| 4 | 12.003 | 7.3676 | 262 | 1655 | 30.7 | 22457 | 22.9 | 0.228 |
| 5 | 14.076 | 6.2864 | 221 | 629 | 11.7 | 9240 | 9.4 | 0.247 |
| 6 | 14.512 | 6.0988 | 222 | 254 | 4.7 | 7494 | 7.7 | 0.495 |
| 7 | 15.222 | 5.8159 | 257 | 376 | 7 | 3504 | 3.6 | 0.157 |
| 8 | 15.912 | 5.5652 | 210 | 166 | 3.1 | 1572 | 1.6 | 0.159 |
| 9 | 16.546 | 5.3534 | 264 | 167 | 3.1 | 1560 | 1.6 | 0.157 |
| 10 | 17.276 | 5.1288 | 276 | 1347 | 25 | 29481 | 30.1 | 0.368 |
| 11 | 18.088 | 4.9003 | 409 | 1115 | 20.7 | 12539 | 12.8 | 0.189 |
| 12 | 18.837 | 4.7069 | 304 | 1479 | 27.4 | 36490 | 37.3 | 0.414 |
| 13 | 19.55 | 4.537 | 338 | 108 | 2 | 567 | 0.6 | 0.088 |
| 14 | 19.964 | 4.4437 | 280 | 1308 | 24.2 | 21827 | 22.3 | 0.28 |
| 15 | 20.536 | 4.3213 | 305 | 167 | 3.1 | 2801 | 2.9 | 0.282 |
| 16 | 21.166 | 4.1941 | 245 | 98 | 1.8 | 848 | 0.9 | 0.145 |
| 17 | 22.393 | 3.9669 | 282 | 5395 | 100 | 97884 | 100 | 0.305 |
| 18 | 22.808 | 3.8956 | 339 | 1373 | 25.4 | 40075 | 40.9 | 0.49 |
| 19 | 23.658 | 3.7576 | 301 | 453 | 8.4 | 14926 | 15.2 | 0.553 |
| 20 | 24.032 | 3.6999 | 274 | 1052 | 19.5 | 21470 | 21.9 | 0.343 |
| 21 | 25.037 | 3.5537 | 233 | 105 | 1.9 | 797 | 0.8 | 0.127 |
| 22 | 25.497 | 3.4906 | 251 | 222 | 4.1 | 4887 | 5 | 0.37 |
| 23 | 25.871 | 3.441 | 271 | 226 | 4.2 | 5548 | 5.7 | 0.412 |
| 24 | 26.562 | 3.353 | 272 | 681 | 12.6 | 24540 | 25.1 | 0.605 |
| 25 | 26.898 | 3.3119 | 259 | 1703 | 31.6 | 33293 | 34 | 0.328 |
| 26 | 27.946 | 3.1901 | 242 | 1150 | 21.3 | 19928 | 20.4 | 0.291 |
| 27 | 29.566 | 3.0188 | 237 | 488 | 9 | 10325 | 10.5 | 0.355 |

TABLE 2-continued

XRPD analysis data of the crystal form B of the compound of Formula (I)

| No. | 2θ (±0.2°) | d (Å) | Background | Peak Height | Peak Height % | Area | Area % | Full Width at Half Maximum |
|---|---|---|---|---|---|---|---|---|
| 28 | 30.181 | 2.9587 | 255 | 90 | 1.7 | 738 | 0.8 | 0.138 |
| 29 | 30.889 | 2.8924 | 230 | 254 | 4.7 | 3356 | 3.4 | 0.222 |
| 30 | 31.759 | 2.8152 | 267 | 334 | 6.2 | 4842 | 4.9 | 0.243 |
| 31 | 32.294 | 2.7698 | 219 | 268 | 5 | 7224 | 7.4 | 0.453 |
| 32 | 32.687 | 2.7374 | 239 | 106 | 2 | 1431 | 1.5 | 0.227 |
| 33 | 33.4 | 2.6806 | 230 | 154 | 2.9 | 2012 | 2.1 | 0.219 |
| 34 | 34.246 | 2.6162 | 248 | 359 | 6.7 | 7055 | 7.2 | 0.33 |
| 35 | 34.721 | 2.5815 | 215 | 159 | 2.9 | 6019 | 6.1 | 0.636 |
| 36 | 36.225 | 2.4777 | 197 | 238 | 4.4 | 5486 | 5.6 | 0.387 |
| 37 | 38 | 2.366 | 190 | 188 | 3.5 | 7441 | 7.6 | 0.665 |

In some embodiments of the present disclosure, the aforesaid crystal form B of the compound of Formula (I) has an XRPD pattern as shown in FIG. 4.

In some embodiments of the present disclosure, the aforesaid crystal form B of the compound of Formula (I) has a differential scanning calorimetry curve with an endothermic peak at 101.04° C.±3° C. and a starting point of an endothermic peak at 188.30° C.±3° C.; and further, in some embodiments of the present disclosure, the crystal form B of the compound of Formula (I) has a DSC pattern as shown in FIG. 5.

In some embodiments of the present disclosure, the aforesaid crystal form B of the compound of Formula (I) has a thermogravimetric analysis curve with a weight loss of 4.087% at 154.18° C.±3° C. and a weight loss of up to 4.610% at 196.80° C.±3° C.; and further, in some embodiments of the present disclosure, the crystal form B of the compound of Formula (I) has a TGA pattern as shown in FIG. 6.

In some embodiments of the present disclosure, in the aforesaid crystal form B of the compound of Formula (I), the compound of Formula (I) has a structure as represented by Compound 2:

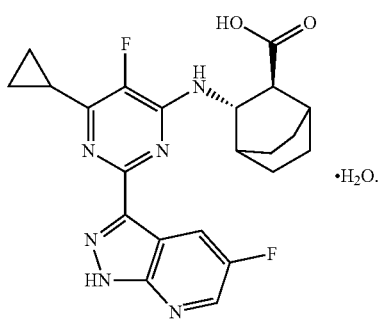

Compound 2

·$H_2O$.

The second object of the present disclosure is to provide a compound as represented by Formula (II) as below and a series of corresponding crystal forms thereof, wherein $n_2$ is selected from 1; and $m_2$ is selected from 0, 0.5, 1, 1.5, 2, 2.5, 3, 3.5 and 4.

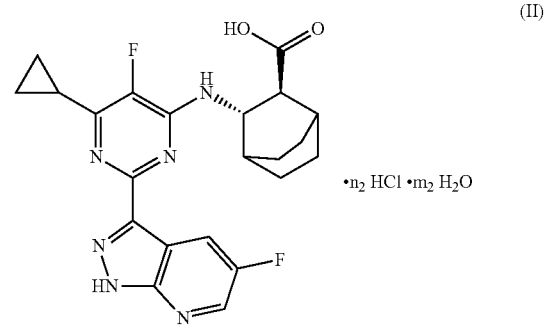

(II)

·$n_2$ HCl ·$m_2$ $H_2O$

Further, the present disclosure further provides a crystal form C of the compound of Formula (II) having an X-ray powder diffraction pattern with characteristic diffraction peaks at 2θ angles of 8.00±0.2°, 15.06±0.2°, 15.84±0.2°. Further, the aforesaid crystal form C of the compound of Formula (II) has an X-ray powder diffraction pattern with characteristic diffraction peaks at 2θ angles of 5.90±0.2°, 6.52±0.2°, 8.00±0.2°, 12.28±0.2°, 15.06±0.2°, 15.84±0.2°, 21.22±0.2°, 26.82±0.2°.

In some embodiments of the present disclosure, the aforesaid crystal form C of the compound of Formula (II) may have XRPD analysis data as shown in Table 3. Persons skilled in the art can understand that as compared with the peak height with higher volatility, the 2θ value in XRPD analysis data is more suitable for characterization of the crystal form due to its smaller volatility.

TABLE 3

XRPD analysis data of crystal form C of the compound of Formula (II)

| No. | 2θ (±0.2°) | d (Å) | Background | Peak Height | Peak Height % | Area | Area % | Full Width at Half Maximum |
|---|---|---|---|---|---|---|---|---|
| 1 | 5.896 | 14.9784 | 339 | 190 | 9 | 2458 | 6.1 | 0.217 |
| 2 | 6.525 | 13.5359 | 330 | 286 | 13.5 | 4340 | 10.7 | 0.254 |
| 3 | 7.65 | 11.5464 | 301 | 467 | 22 | 17551 | 43.2 | 0.63 |
| 4 | 8.004 | 11.0363 | 281 | 2121 | 100 | 40592 | 100 | 0.321 |

TABLE 3-continued

XRPD analysis data of crystal form C of the compound of Formula (II)

| No. | 2θ (±0.2°) | d (Å) | Background | Peak Height | Peak Height % | Area | Area % | Full Width at Half Maximum |
|---|---|---|---|---|---|---|---|---|
| 5 | 10.647 | 8.3027 | 201 | 170 | 8 | 2539 | 6.3 | 0.25 |
| 6 | 11.615 | 7.6124 | 210 | 75 | 3.5 | 807 | 2 | 0.18 |
| 7 | 12.285 | 7.1988 | 225 | 332 | 15.7 | 6529 | 16.1 | 0.33 |
| 8 | 12.834 | 6.8921 | 217 | 131 | 6.2 | 4129 | 10.2 | 0.528 |
| 9 | 13.977 | 6.3308 | 227 | 69 | 3.3 | 709 | 1.7 | 0.172 |
| 10 | 15.064 | 5.8764 | 298 | 396 | 18.7 | 6736 | 16.6 | 0.285 |
| 11 | 15.837 | 5.5914 | 318 | 332 | 15.7 | 5314 | 13.1 | 0.268 |
| 12 | 17.036 | 5.2003 | 268 | 131 | 6.2 | 1905 | 4.7 | 0.244 |
| 13 | 17.888 | 4.9544 | 272 | 119 | 5.6 | 1458 | 3.6 | 0.205 |
| 14 | 19.762 | 4.4888 | 232 | 114 | 5.4 | 1865 | 4.6 | 0.274 |
| 15 | 21.218 | 4.1839 | 262 | 261 | 12.3 | 6294 | 15.5 | 0.404 |
| 16 | 21.871 | 4.0604 | 263 | 122 | 5.8 | 3129 | 7.7 | 0.43 |
| 17 | 24.566 | 3.6207 | 225 | 54 | 2.5 | 712 | 1.8 | 0.221 |
| 18 | 25.44 | 3.4983 | 275 | 75 | 3.5 | 847 | 2.1 | 0.189 |
| 19 | 26.031 | 3.4202 | 326 | 124 | 5.8 | 3185 | 7.8 | 0.431 |
| 20 | 26.822 | 3.3212 | 306 | 153 | 7.2 | 6330 | 15.6 | 0.694 |
| 21 | 31.148 | 2.869 | 215 | 78 | 3.7 | 1189 | 2.9 | 0.256 |
| 22 | 32.943 | 2.7167 | 189 | 50 | 2.4 | 528 | 1.3 | 0.177 |
| 23 | 37.924 | 2.3705 | 148 | 51 | 2.4 | 1150 | 2.8 | 0.378 |
| 24 | 38.066 | 2.362 | 147 | 62 | 2.9 | 1166 | 2.9 | 0.315 |

Further, in some embodiments of the present disclosure, the aforesaid crystal form C of the compound of Formula (II) has an XRPD pattern as shown in FIG. 7.

Further, in some embodiments of the present disclosure, the aforesaid crystal form C of the compound of Formula (II) has a differential scanning calorimetry curve with an endothermic peak at 193.754° C.±3° C. and with an endothermic peak at 235.53° C.±3° C.; and further, in some embodiments of the present disclosure, the aforesaid crystal form C of the compound of Formula (II) has a DSC pattern as shown in FIG. 8.

Further, in some embodiments of the present disclosure, the aforesaid crystal form C of the compound of Formula (II) has a thermogravimetric analysis curve with a weight loss of 5.000% at 117.79° C.±3° C. and a weight loss of up to 12.377% at 222.15° C.±3° C.; and further, in some embodiments of the present disclosure, the aforesaid crystal form C of the compound of Formula (II) has a TGA pattern as shown in FIG. 9.

In some embodiments of the present disclosure, in the aforesaid crystal form C of the compound of Formula (II), the compound of Formula (II) is a compound II-1 as shown below:

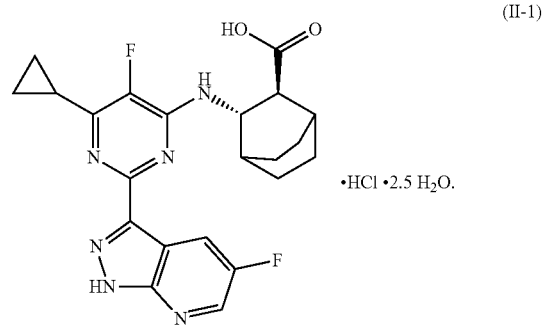

(II-1)

·HCl ·2.5 H$_2$O.

Further, the present disclosure further provides a crystal form D of the compound of Formula (II) having an X-ray powder diffraction pattern with characteristic diffraction peaks at 2θ angles of 6.96±0.2°, 10.31±0.2°, 14.95±0.2°; and further, the aforesaid crystal form D of the compound of Formula (II) has an X-ray powder diffraction pattern with characteristic diffraction peaks at 2θ angles of 6.96±0.2°, 9.44±0.2°, 10.31±0.2°, 14.95±0.2°, 17.38±0.2°, 20.67±0.2°, 21.89±0.2°, 22.72±0.2°. In some embodiments of the present disclosure, the aforesaid crystal form D of the compound of Formula (II) may have XRPD analysis data as shown in Table 4. Persons skilled in the art can understand that as compared with the peak height with higher volatility, the 2θ value in XRPD analysis data is more suitable for characterization of the crystal form due to its smaller volatility.

TABLE 4

XRPD analysis data of the crystal form D of the compound of Formula (II)

| No. | 2θ (0.2°) | d (Å) | Background | Peak Height | Peak Height % | Area | Area % | Full Width at Half Maximum |
|---|---|---|---|---|---|---|---|---|
| 1 | 6.958 | 12.6937 | 327 | 10504 | 100 | 107634 | 100 | 0.172 |
| 2 | 9.444 | 9.3567 | 215 | 475 | 4.5 | 4245 | 3.9 | 0.15 |
| 3 | 10.311 | 8.5723 | 200 | 1397 | 13.3 | 14513 | 13.5 | 0.174 |
| 4 | 12.128 | 7.2917 | 167 | 240 | 2.3 | 2131 | 2 | 0.149 |
| 5 | 12.819 | 6.8999 | 158 | 134 | 1.3 | 1079 | 1 | 0.135 |

TABLE 4-continued

XRPD analysis data of the crystal form D of the compound of Formula (II)

| No. | 2θ (0.2°) | d (Å) | Background | Peak Height | Peak Height % | Area | Area % | Full Width at Half Maximum |
|---|---|---|---|---|---|---|---|---|
| 6 | 14.946 | 5.9227 | 192 | 1447 | 13.8 | 18762 | 17.4 | 0.217 |
| 7 | 15.322 | 5.7781 | 220 | 1572 | 15 | 18161 | 16.9 | 0.194 |
| 8 | 15.892 | 5.5719 | 230 | 180 | 1.7 | 1653 | 1.5 | 0.154 |
| 9 | 16.268 | 5.4439 | 201 | 274 | 2.6 | 3362 | 3.1 | 0.206 |
| 10 | 17.376 | 5.0993 | 149 | 421 | 4 | 4400 | 4.1 | 0.175 |
| 11 | 18.698 | 4.7417 | 133 | 349 | 3.3 | 4010 | 3.7 | 0.193 |
| 12 | 19.72 | 4.4983 | 140 | 95 | 0.9 | 1047 | 1 | 0.185 |
| 13 | 20.666 | 4.2944 | 150 | 1249 | 11.9 | 15103 | 14 | 0.203 |
| 14 | 21.89 | 4.0569 | 166 | 1428 | 13.6 | 15943 | 14.8 | 0.187 |
| 15 | 22.717 | 3.9111 | 154 | 553 | 5.3 | 5277 | 4.9 | 0.16 |
| 16 | 23.806 | 3.7346 | 138 | 112 | 1.1 | 962 | 0.9 | 0.144 |
| 17 | 24.63 | 3.6114 | 138 | 93 | 0.9 | 2102 | 2 | 0.379 |
| 18 | 24.907 | 3.5719 | 134 | 102 | 1 | 2120 | 2 | 0.348 |
| 19 | 25.792 | 3.4514 | 141 | 498 | 4.7 | 4780 | 4.4 | 0.161 |
| 20 | 26.704 | 3.3355 | 155 | 363 | 3.5 | 3656 | 3.4 | 0.169 |
| 21 | 27.452 | 3.2462 | 149 | 139 | 1.3 | 1234 | 1.1 | 0.149 |
| 22 | 28.202 | 3.1616 | 149 | 312 | 3 | 4510 | 4.2 | 0.242 |
| 23 | 28.595 | 3.1191 | 135 | 206 | 2 | 6277 | 5.8 | 0.511 |
| 24 | 28.966 | 3.0799 | 145 | 286 | 2.7 | 6164 | 5.7 | 0.361 |
| 25 | 30.843 | 2.8967 | 127 | 188 | 1.8 | 3685 | 3.4 | 0.329 |
| 26 | 31.198 | 2.8645 | 112 | 320 | 3 | 8234 | 7.6 | 0.431 |
| 27 | 31.75 | 2.816 | 134 | 274 | 2.6 | 1954 | 1.8 | 0.12 |
| 28 | 32.584 | 2.7458 | 109 | 204 | 1.9 | 2685 | 2.5 | 0.221 |
| 29 | 34.359 | 2.6079 | 96 | 129 | 1.2 | 2416 | 2.2 | 0.314 |
| 30 | 35.168 | 2.5497 | 100 | 59 | 0.6 | 645 | 0.6 | 0.183 |
| 31 | 35.816 | 2.505 | 90 | 143 | 1.4 | 2744 | 2.5 | 0.322 |
| 32 | 37.196 | 2.4152 | 85 | 58 | 0.6 | 2118 | 2 | 0.612 |
| 33 | 37.569 | 2.3921 | 84 | 70 | 0.7 | 2106 | 2 | 0.504 |

In some embodiments of the present disclosure, the aforesaid crystal form D of the compound of Formula (II) has an XRPD pattern as shown in FIG. 10.

In some embodiments of the present disclosure, the aforesaid crystal form D of the compound of Formula (II) has a differential scanning calorimetry curve with an endothermic peak at 193.68° C.±3° C.; and further, in some embodiments of the present disclosure, the crystal form D of the compound of Formula (II) has a DSC pattern as shown in FIG. 11.

In some embodiments of the present disclosure, the aforesaid crystal form D of the compound of Formula (II) has a thermogravimetric analysis curve with a weight loss of 0.231% at 78.99° C.±3° C. and a weight loss of up to 5.826% at 198.74° C.±3° C.; and further, in some embodiments of the present disclosure, the crystal form D of the compound of Formula (II) has a TGA pattern as shown in FIG. 12.

In some embodiments of the present disclosure, in the aforesaid crystal form D of the compound of Formula (II), the compound of Formula (II) has the structure of Compound II-2.

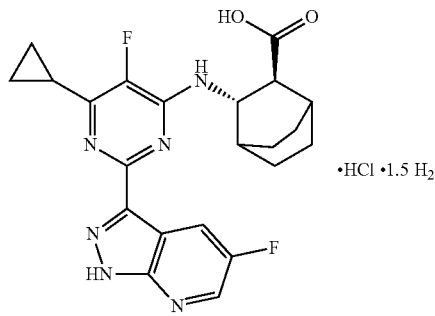

(II-2)

·HCl ·1.5 H₂O.

The third object of the present disclosure is to provide a compound of Compound 3 and its crystal forms.

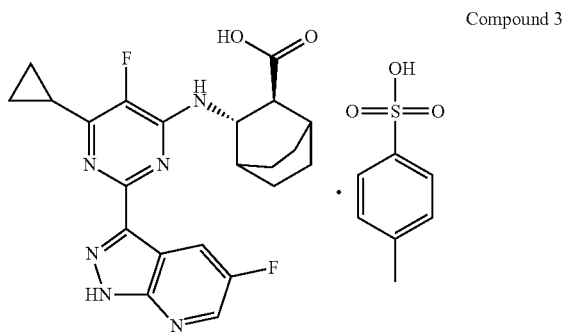

Compound 3

Further, a crystal form E of Compound 3 has an X-ray powder diffraction pattern with characteristic diffraction peaks at 2θ angles of 8.10±0.2°, 9.60±0.2°, 22.97±0.2°; and further, the crystal form E of Compound 3 has an X-ray powder diffraction pattern with characteristic diffraction peaks at 2θ angles of 8.10±0.2°, 9.60±0.2°, 16.09±0.2°, 17.61±0.2°, 18.42±0.2°, 22.97±0.2°, 23.58±0.2°, 25.14±0.2°. In some embodiments of the present disclosure, the crystal form E of Compound 3 may have XRPD analysis data as shown in Table 5. Persons skilled in the art can understand that as compared with the peak height with higher volatility, the 2θ value in XRPD analysis data is more suitable for characterization of the crystal form due to its smaller volatility.

TABLE 5

XRPD analysis data of the crystal form E of Compound 3

| No. | 2θ (±0.2°) | d (Å) | Background | Peak Height | Peak Height % | Area | Area % | Full Width at Half Maximum |
|---|---|---|---|---|---|---|---|---|
| 1 | 8.104 | 10.9007 | 220 | 2030 | 88.6 | 15236 | 69.8 | 0.126 |
| 2 | 9.599 | 9.2062 | 199 | 2212 | 96.6 | 17218 | 78.9 | 0.131 |
| 3 | 9.833 | 8.9879 | 196 | 653 | 28.5 | 6318 | 29 | 0.162 |
| 4 | 11.066 | 7.9888 | 173 | 135 | 5.9 | 1234 | 5.7 | 0.153 |
| 5 | 11.712 | 7.5497 | 176 | 318 | 13.9 | 2476 | 11.3 | 0.131 |
| 6 | 12.487 | 7.0825 | 172 | 491 | 21.4 | 3731 | 17.1 | 0.127 |
| 7 | 12.978 | 6.8158 | 161 | 311 | 13.6 | 2342 | 10.7 | 0.126 |
| 8 | 13.707 | 6.4551 | 153 | 473 | 20.7 | 4368 | 20 | 0.155 |
| 9 | 15.753 | 5.6208 | 167 | 987 | 43.1 | 12876 | 59 | 0.219 |
| 10 | 16.093 | 5.5028 | 177 | 1908 | 83.3 | 16769 | 76.8 | 0.147 |
| 11 | 16.722 | 5.2973 | 185 | 637 | 27.8 | 4379 | 20.1 | 0.115 |
| 12 | 16.996 | 5.2124 | 177 | 852 | 37.2 | 7617 | 34.9 | 0.15 |
| 13 | 17.612 | 5.0316 | 171 | 1586 | 69.3 | 10697 | 49 | 0.113 |
| 14 | 18.415 | 4.8138 | 156 | 973 | 42.5 | 8908 | 40.8 | 0.153 |
| 15 | 19.227 | 4.6125 | 168 | 703 | 30.7 | 5282 | 24.2 | 0.126 |
| 16 | 19.542 | 4.5387 | 159 | 340 | 14.8 | 3998 | 18.3 | 0.197 |
| 17 | 20.077 | 4.4191 | 180 | 464 | 20.3 | 3472 | 15.9 | 0.125 |
| 18 | 20.351 | 4.3601 | 177 | 1111 | 48.5 | 7717 | 35.4 | 0.116 |
| 19 | 21.513 | 4.1271 | 155 | 848 | 37 | 6209 | 28.5 | 0.123 |
| 20 | 22.204 | 4.0004 | 211 | 647 | 28.3 | 5816 | 26.7 | 0.151 |
| 21 | 22.595 | 3.932 | 255 | 182 | 7.9 | 1028 | 4.7 | 0.095 |
| 22 | 22.974 | 3.8679 | 179 | 2290 | 100 | 21823 | 100 | 0.16 |
| 23 | 23.254 | 3.822 | 234 | 169 | 7.4 | 2243 | 10.3 | 0.223 |
| 24 | 23.585 | 3.769 | 222 | 2202 | 96.2 | 21025 | 96.3 | 0.16 |
| 25 | 24.199 | 3.6748 | 183 | 511 | 22.3 | 4274 | 19.6 | 0.14 |
| 26 | 24.907 | 3.5719 | 168 | 534 | 23.3 | 7062 | 32.4 | 0.222 |
| 27 | 25.143 | 3.5389 | 163 | 1575 | 68.8 | 14955 | 68.5 | 0.159 |
| 28 | 25.595 | 3.4775 | 155 | 75 | 3.3 | 862 | 3.9 | 0.193 |
| 29 | 26.073 | 3.4148 | 146 | 334 | 14.6 | 2842 | 13 | 0.143 |
| 30 | 26.765 | 3.3281 | 142 | 72 | 3.1 | 588 | 2.7 | 0.137 |
| 31 | 27.252 | 3.2696 | 169 | 230 | 10 | 2174 | 10 | 0.158 |
| 32 | 27.507 | 3.24 | 181 | 112 | 4.9 | 1090 | 5 | 0.163 |
| 33 | 27.885 | 3.1969 | 151 | 323 | 14.1 | 4950 | 22.7 | 0.257 |
| 34 | 28.417 | 3.1382 | 206 | 494 | 21.6 | 3007 | 13.8 | 0.102 |
| 35 | 28.932 | 3.0835 | 153 | 402 | 17.6 | 3593 | 16.5 | 0.15 |
| 36 | 29.564 | 3.019 | 137 | 171 | 7.5 | 2349 | 10.8 | 0.23 |
| 37 | 30.076 | 2.9688 | 123 | 280 | 12.2 | 4390 | 20.1 | 0.263 |
| 38 | 31.055 | 2.8774 | 119 | 103 | 4.5 | 847 | 3.9 | 0.138 |
| 39 | 31.673 | 2.8227 | 160 | 146 | 6.4 | 2491 | 11.4 | 0.286 |
| 40 | 32.263 | 2.7724 | 125 | 150 | 6.6 | 3742 | 17.1 | 0.418 |
| 41 | 32.539 | 2.7495 | 153 | 176 | 7.7 | 1735 | 8 | 0.165 |
| 42 | 33.116 | 2.7029 | 120 | 107 | 4.7 | 790 | 3.6 | 0.124 |
| 43 | 34.414 | 2.6038 | 110 | 125 | 5.5 | 2594 | 11.9 | 0.348 |
| 44 | 35.364 | 2.536 | 100 | 72 | 3.1 | 2592 | 11.9 | 0.604 |
| 45 | 35.634 | 2.5174 | 103 | 138 | 6 | 2742 | 12.6 | 0.333 |
| 46 | 35.735 | 2.5105 | 103 | 122 | 5.3 | 2720 | 12.5 | 0.374 |
| 47 | 37.236 | 2.4127 | 105 | 68 | 3 | 1379 | 6.3 | 0.34 |
| 48 | 37.851 | 2.3749 | 113 | 69 | 3 | 1045 | 4.8 | 0.254 |
| 49 | 38.124 | 2.3586 | 115 | 55 | 2.4 | 1049 | 4.8 | 0.32 |
| 50 | 38.953 | 2.3103 | 112 | 71 | 3.1 | 884 | 4.1 | 0.209 |

In some embodiments of the present disclosure, the aforesaid crystal form E of Compound 3 has an XRPD pattern as shown in FIG. 13.

In some embodiments of the present disclosure, the aforesaid crystal form E of Compound 3 has a differential scanning calorimetry curve with a starting point of an endothermic peak at 258.27° C.±3° C.; and further, in some embodiments of the present disclosure, the crystal form E of Compound 3 has a DSC pattern as shown in FIG. 14.

In some embodiments of the present disclosure, the aforesaid crystal form E of Compound 3 has a thermogravimetric analysis curve with a weight loss of 0.905% at 121.35° C.±3° C.; and further, in some embodiments of the present disclosure, the crystal form E of Compound 3 has a TGA pattern as shown in FIG. 15.

The fourth object of the present disclosure is to provide a compound of Formula (III) as shown below and its crystal forms,

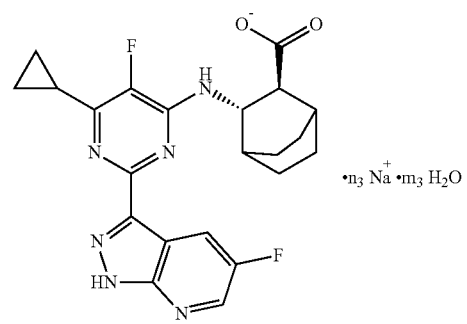

(III)

·$n_3$ Na$^+$ ·$m_3$ H$_2$O wherein,
$n_3$ is selected from 1;
$m_3$ is selected from 0, 0.5, 1, 1.5, 2, 2.5, 3, 3.5 and 4.

In particular, the present disclosure further provides a crystal form F of the compound of Formula (III) having an X-ray powder diffraction pattern with characteristic diffraction peaks at 2θ angles of 6.47±0.2°, 9.11±0.2°, 9.90±0.2°; and further, the aforesaid crystal form F of the compound of Formula (III) has an X-ray powder diffraction pattern with characteristic diffraction peaks at 2θ angles of 6.47±0.2°, 9.11±0.2°, 9.90±0.2°, 15.85±0.2°, 16.28±0.2°, 19.40±0.2°, 20.37±0.2°, 24.10±0.2°.

In some embodiments of the present disclosure, the aforesaid crystal form F of the compound of Formula (III) may have XRPD analysis data as shown in Table 6. Persons skilled in the art can understand that as compared with the peak height with higher volatility, the 2θ value in XRPD analysis data is more suitable for characterization of the crystal form due to its smaller volatility.

TABLE 6

XRPD analysis data of crystal form F of the compound of Formula (III)

| No. | 2θ (±0.2°) | d (Å) | Background | Peak Height | Peak Height % | Area | Area % | Full Width at Half Maximum |
|---|---|---|---|---|---|---|---|---|
| 1 | 4.477 | 19.7217 | 646 | 127 | 2.6 | 3659 | 7.7 | 0.483 |
| 2 | 6.467 | 13.6557 | 371 | 4830 | 100 | 47786 | 100 | 0.166 |
| 3 | 9.109 | 9.7009 | 263 | 675 | 14 | 5855 | 12.3 | 0.145 |
| 4 | 9.895 | 8.9319 | 246 | 872 | 18.1 | 8527 | 17.8 | 0.164 |
| 5 | 11.189 | 7.9011 | 183 | 50 | 1 | 402 | 0.8 | 0.135 |
| 6 | 11.779 | 7.5069 | 178 | 58 | 1.2 | 220 | 0.5 | 0.064 |
| 7 | 12.899 | 6.8576 | 186 | 268 | 5.5 | 2041 | 4.3 | 0.128 |
| 8 | 14.473 | 6.1151 | 198 | 95 | 2 | 702 | 1.5 | 0.124 |
| 9 | 15.34 | 5.7714 | 263 | 245 | 5.1 | 868 | 1.8 | 0.059 |
| 10 | 15.854 | 5.5855 | 199 | 788 | 16.3 | 10575 | 22.1 | 0.225 |
| 11 | 16.285 | 5.4384 | 231 | 159 | 3.3 | 769 | 1.6 | 0.081 |
| 12 | 17.416 | 5.0878 | 197 | 246 | 5.1 | 2615 | 5.5 | 0.178 |
| 13 | 17.885 | 4.9553 | 197 | 228 | 4.7 | 2194 | 4.6 | 0.161 |
| 14 | 18.693 | 4.743 | 197 | 255 | 5.3 | 2562 | 5.4 | 0.168 |
| 15 | 19.402 | 4.5712 | 202 | 395 | 8.2 | 4724 | 9.9 | 0.201 |
| 16 | 20.374 | 4.3553 | 176 | 365 | 7.6 | 4119 | 8.6 | 0.189 |
| 17 | 21.377 | 4.1532 | 155 | 61 | 1.3 | 668 | 1.4 | 0.184 |
| 18 | 22.221 | 3.9972 | 153 | 43 | 0.9 | 441 | 0.9 | 0.172 |
| 19 | 23.235 | 3.8251 | 186 | 169 | 3.5 | 1524 | 3.2 | 0.151 |
| 20 | 23.59 | 3.7682 | 177 | 60 | 1.2 | 1161 | 2.4 | 0.324 |
| 21 | 24.099 | 3.6898 | 178 | 406 | 8.4 | 5888 | 12.3 | 0.243 |
| 22 | 24.707 | 3.6003 | 180 | 151 | 3.1 | 924 | 1.9 | 0.103 |
| 23 | 26.368 | 3.3772 | 139 | 91 | 1.9 | 1466 | 3.1 | 0.27 |
| 24 | 27.608 | 3.2284 | 152 | 172 | 3.6 | 2013 | 4.2 | 0.196 |
| 25 | 28.159 | 3.1663 | 128 | 236 | 4.9 | 5256 | 11 | 0.373 |
| 26 | 29.862 | 2.9896 | 112 | 44 | 0.9 | 1299 | 2.7 | 0.495 |
| 27 | 31.77 | 2.8142 | 99 | 45 | 0.9 | 705 | 1.5 | 0.263 |
| 28 | 32.327 | 2.767 | 97 | 36 | 0.7 | 431 | 0.9 | 0.201 |
| 29 | 35.334 | 2.5381 | 78 | 59 | 1.2 | 756 | 1.6 | 0.215 |
| 30 | 37.497 | 2.3965 | 78 | 50 | 1 | 793 | 1.7 | 0.266 |

In some embodiments of the present disclosure, the aforesaid crystal form F of the compound of Formula (III) has an XRPD pattern as shown in FIG. 16.

In some embodiments of the present disclosure, the aforesaid crystal form F of the compound of Formula (III) has a differential scanning calorimetry curve with an endothermic peak at 78.73° C.±3° C., a starting point of an endothermic peak at 222.37° C.±3° C., and an exothermic peak at 245.01° C.±3° C.; and further, in some embodiments of the present disclosure, the aforesaid crystal form F of the compound of Formula (III) has a DSC pattern as shown in FIG. 17.

In some embodiments of the present disclosure, the aforesaid crystal form F of the compound of Formula (III) has a thermogravimetric analysis curve with a weight loss of 1.192% at 39.57° C.±3° C., a weight loss of up to 3.683% at 81.27° C.±3° C., and a weight loss of up to 6.023% at 199.63° C.±3° C.; and further, in some embodiments of the present disclosure, the aforesaid crystal form F has a TGA pattern as shown in FIG. 18.

In particular, the present disclosure further provides a crystal form G of the compound of Formula (III) having an X-ray powder diffraction pattern with characteristic diffraction peaks at 2θ angles of 6.23±0.2°, 7.20±0.2°, 14.30±0.2°. Further, the aforesaid crystal form G of the compound of Formula (III) has an X-ray powder diffraction pattern with characteristic diffraction peaks at 2θ angles of 6.23±0.2°, 7.20±0.2°, 7.81±0.2°, 11.22±0.2°, 12.38±0.2°, 14.30±0.2°, 15.90±0.2°, 18.97±0.2°.

In some embodiments of the present disclosure, the aforesaid crystal form G of the compound of Formula (III) may have XRPD analysis data as shown in Table 7. Persons skilled in the art can understand that as compared with the peak height with higher volatility, the 2θ value in XRPD analysis data is more suitable for characterization of the crystal form due to its smaller volatility.

TABLE 7

XRPD analysis data of the crystal form G of the compound of Formula (III)

| # | 2θ (±0.2°) | d (Å) | Background | Peak Height | Peak Height % | Area | Area % | Full Width at Half Maximum |
|---|---|---|---|---|---|---|---|---|
| 1 | 4.806 | 18.3721 | 417 | 116 | 8.5 | 915 | 5 | 0.132 |
| 2 | 5.933 | 14.8846 | 350 | 338 | 24.7 | 11701 | 64.2 | 0.58 |
| 3 | 6.23 | 14.1754 | 338 | 1179 | 86.2 | 16504 | 90.6 | 0.235 |
| 4 | 6.527 | 13.5313 | 326 | 147 | 10.8 | 2596 | 14.2 | 0.296 |
| 5 | 7.197 | 12.2729 | 290 | 1367 | 100 | 18223 | 100 | 0.223 |
| 6 | 7.809 | 11.3122 | 260 | 385 | 28.2 | 4176 | 22.9 | 0.182 |
| 7 | 9.5 | 9.3019 | 210 | 135 | 9.9 | 758 | 4.2 | 0.094 |
| 8 | 9.9 | 8.9269 | 200 | 65 | 4.8 | 598 | 3.3 | 0.154 |
| 9 | 10.182 | 8.6802 | 196 | 62 | 4.5 | 569 | 3.1 | 0.154 |
| 10 | 11.217 | 7.8817 | 184 | 282 | 20.6 | 3130 | 17.2 | 0.186 |
| 11 | 11.785 | 7.5029 | 193 | 87 | 6.4 | 1236 | 6.8 | 0.238 |
| 12 | 12.383 | 7.1422 | 189 | 442 | 32.3 | 4194 | 23 | 0.159 |
| 13 | 12.915 | 6.8488 | 181 | 57 | 4.2 | 433 | 2.4 | 0.127 |
| 14 | 13.327 | 6.6383 | 186 | 167 | 12.2 | 1471 | 8.1 | 0.148 |
| 15 | 13.918 | 6.3576 | 203 | 308 | 22.5 | 3768 | 20.7 | 0.205 |
| 16 | 14.298 | 6.1896 | 199 | 1013 | 74.1 | 11879 | 65.2 | 0.197 |
| 17 | 14.634 | 6.0479 | 202 | 340 | 24.9 | 5330 | 29.2 | 0.263 |
| 18 | 15.617 | 5.6694 | 212 | 197 | 14.4 | 3722 | 20.4 | 0.317 |
| 19 | 15.895 | 5.5711 | 211 | 639 | 46.7 | 9982 | 54.8 | 0.262 |
| 20 | 16.439 | 5.388 | 226 | 61 | 4.5 | 788 | 4.3 | 0.217 |
| 21 | 16.737 | 5.2927 | 218 | 96 | 7 | 558 | 3.1 | 0.097 |
| 22 | 17.071 | 5.1897 | 220 | 60 | 4.4 | 247 | 1.4 | 0.069 |
| 23 | 17.555 | 5.0477 | 213 | 72 | 5.3 | 509 | 2.8 | 0.119 |
| 24 | 17.931 | 4.9428 | 212 | 84 | 6.1 | 1072 | 5.9 | 0.214 |
| 25 | 18.177 | 4.8763 | 212 | 53 | 3.9 | 969 | 5.3 | 0.307 |
| 26 | 18.969 | 4.6746 | 203 | 702 | 51.4 | 9135 | 50.1 | 0.218 |
| 27 | 19.921 | 4.4532 | 188 | 104 | 7.6 | 2581 | 14.2 | 0.416 |
| 28 | 20.173 | 4.3982 | 183 | 164 | 12 | 2586 | 14.2 | 0.264 |
| 29 | 21.065 | 4.214 | 178 | 127 | 9.3 | 1614 | 8.9 | 0.213 |
| 30 | 21.984 | 4.0397 | 188 | 187 | 13.7 | 2299 | 12.6 | 0.206 |
| 31 | 22.401 | 3.9656 | 192 | 189 | 13.8 | 5545 | 30.4 | 0.492 |
| 32 | 22.679 | 3.9175 | 197 | 130 | 9.5 | 4452 | 24.4 | 0.574 |
| 33 | 22.816 | 3.8943 | 198 | 102 | 7.5 | 3129 | 17.2 | 0.514 |
| 34 | 23.528 | 3.778 | 191 | 129 | 9.4 | 1302 | 7.1 | 0.169 |
| 35 | 25.319 | 3.5147 | 178 | 380 | 27.8 | 7725 | 42.4 | 0.341 |
| 36 | 26.107 | 3.4104 | 191 | 165 | 12.1 | 2726 | 15 | 0.277 |
| 37 | 27.315 | 3.2622 | 202 | 97 | 7.1 | 1046 | 5.7 | 0.181 |
| 38 | 28.063 | 3.177 | 201 | 208 | 15.2 | 4429 | 24.3 | 0.357 |
| 39 | 28.753 | 3.1023 | 189 | 322 | 23.6 | 4225 | 23.2 | 0.22 |
| 40 | 30.273 | 2.9499 | 179 | 52 | 3.8 | 1169 | 6.4 | 0.377 |
| 41 | 30.905 | 2.891 | 165 | 90 | 6.6 | 1440 | 7.9 | 0.268 |
| 42 | 31.454 | 2.8418 | 173 | 86 | 6.3 | 927 | 5.1 | 0.181 |
| 43 | 33.08 | 2.7057 | 129 | 54 | 4 | 1369 | 7.5 | 0.425 |
| 44 | 33.43 | 2.6782 | 122 | 62 | 4.5 | 2397 | 13.2 | 0.648 |
| 45 | 35.019 | 2.5602 | 118 | 45 | 3.3 | 971 | 5.3 | 0.362 |
| 46 | 35.402 | 2.5334 | 119 | 49 | 3.6 | 983 | 5.4 | 0.336 |
| 47 | 36.172 | 2.4812 | 123 | 58 | 4.2 | 712 | 3.9 | 0.206 |
| 48 | 36.721 | 2.4454 | 121 | 62 | 4.5 | 424 | 2.3 | 0.115 |
| 49 | 37.749 | 2.3811 | 118 | 46 | 3.4 | 429 | 2.4 | 0.156 |
| 50 | 38.508 | 2.3359 | 116 | 49 | 3.6 | 322 | 1.8 | 0.11 |

Further, in some embodiments of the present disclosure, the aforesaid crystal form G of the compound of Formula (III) has an XRPD pattern as shown in FIG. 19.

In some embodiments of the present disclosure, the aforesaid crystal form G of the compound of Formula (III) has a differential scanning calorimetry curve with an endothermic peak at 70.13° C.±3° C.; and further, in some embodiments of the present disclosure, the aforesaid crystal form G of the compound of Formula (III) has a DSC pattern as shown in FIG. 20.

In some embodiments of the present disclosure, the aforesaid crystal form G of the compound of Formula (III) has a thermogravimetric analysis curve as shown in FIG. 21.

In some embodiments of the present disclosure, in the aforesaid crystal forms F and G of the compound of Formula (III), the compound of Formula (III) has a structure of compound

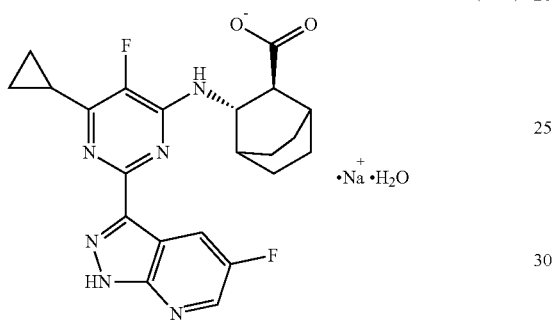

(III-1)

The fourth object of the present disclosure is to further provide a compound as represented by Formula (IV):

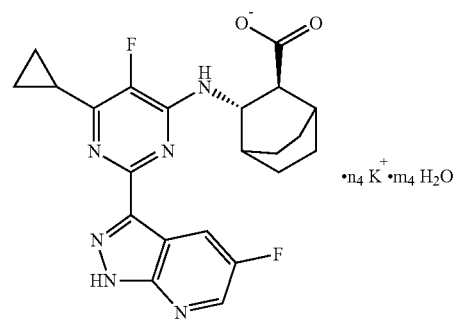

(IV)

wherein, $n_4$ is selected from 1;

$m_4$ is selected from 0, 0.5, 1, 1.5, 2, 2.5, 3, 3.5 and 4.

In particular, the present disclosure further provides a crystal form H of the compound of Formula (IV) having an X-ray powder diffraction pattern with characteristic diffraction peaks at 2θ angles of 4.71±0.2°, 5.56±0.2°, 18.16±0.2°, and further, the aforesaid crystal form H of the compound of Formula (IV) has an X-ray powder diffraction pattern with characteristic diffraction peaks at 2θ angles of 4.71±0.2°, 5.56±0.2°, 7.98±0.2°, 8.97±0.2°, 18.16±0.2°, 22.42±0.2°, 26.37±0.2°, 27.10±0.2°.

Further, in some embodiments of the present disclosure, the aforesaid crystal form H of the compound of Formula (IV) may have XRPD analysis data as shown in Table 8. Persons skilled in the art can understand that as compared with the peak height with higher volatility, the 2θ value in XRPD analysis data is more suitable for characterization of the crystal form due to its smaller volatility.

TABLE 8

XRPD analysis data of the crystal form H of the compound of Formula (IV)

| No. | 2θ (±0.2°) | d (Å) | Background | Peak Height | Peak Height % | Area | Area % | Full Width at Half Maximum |
|---|---|---|---|---|---|---|---|---|
| 1 | 4.71 | 18.7467 | 698 | 1810 | 100 | 27322 | 78.8 | 0.253 |
| 2 | 5.559 | 15.8846 | 325 | 1530 | 84.5 | 34660 | 100 | 0.38 |
| 3 | 7.984 | 11.0651 | 254 | 196 | 10.8 | 2728 | 7.9 | 0.233 |
| 4 | 8.971 | 9.8493 | 236 | 192 | 10.6 | 2660 | 7.7 | 0.232 |
| 5 | 12.543 | 7.0513 | 154 | 54 | 3 | 383 | 1.1 | 0.119 |
| 6 | 13.361 | 6.6212 | 156 | 50 | 2.8 | 358 | 1 | 0.12 |
| 7 | 14.352 | 6.1665 | 194 | 107 | 5.9 | 1976 | 5.7 | 0.31 |
| 8 | 15.186 | 5.8293 | 194 | 141 | 7.8 | 2261 | 6.5 | 0.269 |
| 9 | 16.125 | 5.4921 | 168 | 47 | 2.6 | 518 | 1.5 | 0.185 |
| 10 | 16.743 | 5.2906 | 163 | 155 | 8.6 | 2577 | 7.4 | 0.279 |
| 11 | 18.163 | 4.8802 | 158 | 267 | 14.8 | 11959 | 34.5 | 0.751 |
| 12 | 18.518 | 4.7875 | 203 | 247 | 13.6 | 11351 | 32.7 | 0.77 |
| 13 | 19.151 | 4.6305 | 296 | 87 | 4.8 | 501 | 1.4 | 0.097 |
| 14 | 19.659 | 4.512 | 226 | 79 | 4.4 | 2728 | 7.9 | 0.579 |
| 15 | 19.921 | 4.4533 | 208 | 115 | 6.4 | 2649 | 7.6 | 0.386 |
| 16 | 22.42 | 3.9622 | 132 | 199 | 11 | 5833 | 16.8 | 0.491 |
| 17 | 23.268 | 3.8197 | 136 | 55 | 3 | 288 | 0.8 | 0.088 |
| 18 | 26.367 | 3.3773 | 188 | 289 | 16 | 5642 | 16.3 | 0.327 |
| 19 | 27.097 | 3.2881 | 199 | 101 | 5.6 | 4789 | 13.8 | 0.795 |
| 20 | 27.574 | 3.2322 | 231 | 64 | 3.5 | 1007 | 2.9 | 0.264 |
| 21 | 28.355 | 3.1449 | 173 | 50 | 2.8 | 467 | 1.3 | 0.157 |
| 22 | 29.319 | 3.0437 | 148 | 70 | 3.9 | 2241 | 6.5 | 0.537 |
| 23 | 30.035 | 2.9727 | 154 | 61 | 3.4 | 2045 | 5.9 | 0.562 |
| 24 | 32.92 | 2.7185 | 109 | 41 | 2.3 | 385 | 1.1 | 0.157 |

Further, in some embodiments of the present disclosure, the aforesaid crystal form H of the compound of Formula (IV) has an XRPD pattern as shown in FIG. 22.

In some embodiments of the present disclosure, the aforesaid crystal form H of the compound of Formula (IV) has a differential scanning calorimetry curve with an endothermic peak at 141.17° C.±3° C., an endothermic peak at 243.06° C.±3° C., and an exothermic peak at 257.74° C.±3° C.; and further, in some embodiments of the present disclosure, the aforesaid crystal form H of the compound of Formula (IV) has a DSC pattern as shown in FIG. 23.

In some embodiments of the present disclosure, the aforesaid crystal form H of the compound of Formula (IV) has a thermogravimetric analysis curve with a weight loss of 1.328% at 73.74±3° C., a weight loss of up to 4.986% at 207.43° C.±3° C., and a weight loss of up to 5.627% at 249.40° C.±3° C.; and further, in some embodiments of the present disclosure, the aforesaid crystal form H of the compound of Formula (IV) has a TGA pattern as shown in FIG. 24.

In particular, the present disclosure further provides a crystal form I of the compound of Formula (IV) having an X-ray powder diffraction pattern with characteristic diffraction peaks at 2θ angles of 4.89±0.2°, 6.19±0.2°, 7.45±0.2°; and further, the aforesaid crystal form I of the compound of Formula (IV) has an X-ray powder diffraction pattern with characteristic diffraction peaks at 2θ angles of 4.89±0.2°, 6.19±0.2°, 7.45±0.2°, 16.23±0.2°, 18.28±0.2°, 18.95±0.2°, 26.31±0.2°, 27.04±0.2°. In some embodiments of the present disclosure, the aforesaid crystal form I of the compound of Formula (IV) may have XRPD analysis data as shown in Table 9. Persons skilled in the art can understand that as compared with the peak height with higher volatility, the 2θ value in XRPD analysis data is more suitable for characterization of the crystal form due to its smaller volatility.

TABLE 9

XRPD analysis data of the crystal form I of the compound of Formula (IV)

| No. | 2θ | d (Å) | Background | Peak Height | Peak Height % | Area | Area % | Full Width at Half Maximum |
|---|---|---|---|---|---|---|---|---|
| 1 | 4.889 | 18.0604 | 377 | 2218 | 100 | 31536 | 100 | 0.238 |
| 2 | 6.188 | 14.2714 | 301 | 540 | 24.3 | 5892 | 18.7 | 0.183 |
| 3 | 7.452 | 11.8528 | 243 | 524 | 23.6 | 5901 | 18.7 | 0.189 |
| 4 | 9.717 | 9.0947 | 164 | 61 | 2.8 | 1422 | 4.5 | 0.391 |
| 5 | 9.968 | 8.866 | 160 | 48 | 2.2 | 1264 | 4 | 0.441 |
| 6 | 12.225 | 7.2338 | 150 | 108 | 4.9 | 1007 | 3.2 | 0.156 |
| 7 | 14.529 | 6.0914 | 164 | 53 | 2.4 | 1492 | 4.7 | 0.472 |
| 8 | 15.022 | 5.8928 | 179 | 145 | 6.5 | 2218 | 7 | 0.256 |
| 9 | 15.814 | 5.5992 | 168 | 86 | 3.9 | 1879 | 6 | 0.366 |
| 10 | 16.226 | 5.4581 | 164 | 130 | 5.9 | 1754 | 5.6 | 0.226 |
| 11 | 18.28 | 4.8493 | 186 | 169 | 7.6 | 5975 | 18.9 | 0.593 |
| 12 | 18.954 | 4.6783 | 183 | 151 | 6.8 | 6072 | 19.3 | 0.674 |
| 13 | 19.822 | 4.4754 | 163 | 106 | 4.8 | 1441 | 4.6 | 0.228 |
| 14 | 20.923 | 4.2422 | 134 | 96 | 4.3 | 965 | 3.1 | 0.169 |
| 15 | 21.821 | 4.0696 | 135 | 88 | 4 | 962 | 3.1 | 0.183 |
| 16 | 22.575 | 3.9353 | 135 | 61 | 2.8 | 645 | 2 | 0.177 |
| 17 | 23.384 | 3.801 | 129 | 47 | 2.1 | 524 | 1.7 | 0.187 |
| 18 | 26.307 | 3.3849 | 148 | 151 | 6.8 | 2685 | 8.5 | 0.298 |
| 19 | 27.035 | 3.2955 | 166 | 152 | 6.9 | 2571 | 8.2 | 0.284 |
| 20 | 28.12 | 3.1707 | 168 | 73 | 3.3 | 1308 | 4.1 | 0.3 |
| 21 | 29.98 | 2.9781 | 153 | 82 | 3.7 | 2135 | 6.8 | 0.437 |
| 22 | 35.366 | 2.5359 | 92 | 36 | 1.6 | 450 | 1.4 | 0.21 |
| 23 | 38.437 | 2.34 | 105 | 42 | 1.9 | 333 | 1.1 | 0.133 |

Further, in some embodiments of the present disclosure, the aforesaid crystal form I of the compound of Formula (IV) has an XRPD pattern as shown in FIG. 25.

In some embodiments of the present disclosure, the aforesaid crystal form I of the compound of Formula (IV) has a differential scanning calorimetry curve with an endothermic peak at 86.86° C.±3° C.; and further, in some embodiments of the present disclosure, the aforesaid crystal form I of the compound of Formula (IV) has a DSC pattern as shown in FIG. 26.

In some embodiments of the present disclosure, the aforesaid crystal form I of the compound of Formula (IV) has a thermogravimetric analysis curve with a weight loss of 1.298% at 46.81° C.±3° C., a weight loss of up to 3.607% at 89.20° C.±3° C. and a weight loss of up to 4.641% at 169.65° C.±3° C.; and further, in some embodiments of the present disclosure, the aforesaid crystal form I of the compound of Formula (IV) has a TGA pattern as shown in FIG. 27.

In particular, the present disclosure further provides a crystal form J of the compound of Formula (IV) having an X-ray powder diffraction pattern with characteristic diffraction peaks at 2θ angles of 4.97±0.2°, 16.33±0.2°, 23.92±0.2°; and further, the aforesaid crystal form J of the compound of Formula (IV) has an X-ray powder diffraction pattern with characteristic diffraction peaks at 2θ angles of 4.97±0.2°, 6.19±0.2°, 16.33±0.2°, 19.15±0.2°, 19.84±0.2°, 21.02±0.2°, 22.68±0.2°, 23.92±0.2°. Further, in some embodiments of the present disclosure, the aforesaid crystal form J of the compound of Formula (IV) may have XRPD analysis data as shown in Table 10. Persons skilled in the art can understand that as compared with the peak height with higher volatility, the 2θ value in XRPD analysis data is more suitable for characterization of the crystal form due to its smaller volatility.

Further, in some embodiments of the present disclosure, the aforesaid crystal form J of the compound of Formula (IV) has an XRPD pattern as shown in FIG. 28.

In some embodiments of the present disclosure, the aforesaid crystal form J of the compound of Formula (IV) has a differential scanning calorimetry curve with an endothermic peak at 61.29° C.±3° C., an endothermic peak at 86.40° C.±3° C., and an endothermic peak at 151.50° C.±3° C.; and further, in some embodiments of the present disclosure, the aforesaid crystal form J of the compound of Formula (IV) has a DSC pattern as shown in FIG. 29.

In some embodiments of the present disclosure, the aforesaid crystal form J of the compound of Formula (IV) has a thermogravimetric analysis curve with a weight loss of 3.412% at 220.12° C.±3° C.; and further, in some embodiments of the present disclosure, the aforesaid crystal form J of the compound of Formula (IV) has a TGA pattern as shown in FIG. 30.

In particular, the present disclosure further provides the crystal form K of the compound of Formula (IV) having an X-ray powder diffraction pattern with characteristic diffraction peaks at 2θ angles of 4.83±0.2°, 7.39±0.2°, 14.80±0.2°; further, the aforesaid crystal form K of the compound of Formula (IV) has an X-ray powder diffraction pattern with characteristic diffraction peaks at 2θ angles of 4.83±0.2°, 7.39±0.2°, 11.61±0.2°, 14.81±0.2°, 16.19±0.2°, 18.50±0.2°, 19.29±0.2°, 20.86±0.2°.

In some embodiments of the present disclosure, the aforesaid crystal form K of the compound of Formula (IV) may have XRPD analysis data as shown in Table 11. Persons skilled in the art can understand that as compared with the peak height with higher volatility, the 2θvalue in XRPD analysis data is more suitable for characterization of the crystal form due to its smaller volatility.

TABLE 10

XRPD analysis data of the crystal form J of the compound of Formula (IV)

| # | 2θ (±0.2°) | d (Å) | Background | Peak Height | Peak Height % | Area | Area % | Full Width at Half Maximum |
|---|---|---|---|---|---|---|---|---|
| 1 | 4.967 | 17.7781 | 437 | 5372 | 100 | 77952 | 100 | 0.243 |
| 2 | 6.191 | 14.2641 | 356 | 269 | 5 | 2956 | 3.8 | 0.184 |
| 3 | 9.94 | 8.8913 | 169 | 84 | 1.6 | 1776 | 2.3 | 0.354 |
| 4 | 11.773 | 7.5108 | 145 | 74 | 1.4 | 1453 | 1.9 | 0.329 |
| 5 | 14.569 | 6.0747 | 145 | 123 | 2.3 | 1504 | 1.9 | 0.205 |
| 6 | 15.043 | 5.8844 | 151 | 149 | 2.8 | 2816 | 3.6 | 0.317 |
| 7 | 15.739 | 5.6258 | 158 | 44 | 0.8 | 791 | 1 | 0.301 |
| 8 | 16.326 | 5.4249 | 142 | 309 | 5.8 | 5108 | 6.6 | 0.277 |
| 9 | 18.378 | 4.8234 | 165 | 164 | 3.1 | 2806 | 3.6 | 0.287 |
| 10 | 19.148 | 4.6313 | 172 | 224 | 4.2 | 6040 | 7.7 | 0.452 |
| 11 | 19.839 | 4.4715 | 145 | 211 | 3.9 | 3016 | 3.9 | 0.24 |
| 12 | 21.021 | 4.2227 | 122 | 277 | 5.2 | 4568 | 5.9 | 0.276 |
| 13 | 21.728 | 4.0869 | 123 | 49 | 0.9 | 313 | 0.4 | 0.107 |
| 14 | 22.679 | 3.9176 | 123 | 169 | 3.1 | 1947 | 2.5 | 0.193 |
| 15 | 23.448 | 3.7908 | 126 | 127 | 2.4 | 1890 | 2.4 | 0.25 |
| 16 | 23.922 | 3.7167 | 110 | 968 | 18 | 4543 | 5.8 | 0.079 |
| 17 | 26.328 | 3.3823 | 127 | 105 | 2 | 2810 | 3.6 | 0.449 |
| 18 | 27.037 | 3.2952 | 124 | 95 | 1.8 | 4131 | 5.3 | 0.729 |
| 19 | 28.043 | 3.1792 | 128 | 80 | 1.5 | 2033 | 2.6 | 0.426 |
| 20 | 28.682 | 3.1098 | 134 | 43 | 0.8 | 472 | 0.6 | 0.184 |
| 21 | 29.895 | 2.9863 | 127 | 100 | 1.9 | 1393 | 1.8 | 0.234 |
| 22 | 30.996 | 2.8827 | 120 | 64 | 1.2 | 1523 | 2 | 0.399 |
| 23 | 34.409 | 2.6042 | 96 | 49 | 0.9 | 710 | 0.9 | 0.243 |
| 24 | 39.37 | 2.2867 | 97 | 37 | 0.7 | 233 | 0.3 | 0.106 |

TABLE 11

XRPD analysis data of the crystal form K of the compound of Formula (IV)

| No. | 2θ (±0.2°) | d (Å) | Background | Peak Height | Peak Height % | Area | Area % | Full Width at Half Maximum |
|---|---|---|---|---|---|---|---|---|
| 1 | 4.827 | 18.2898 | 488 | 5225 | 100 | 54267 | 100 | 0.174 |
| 2 | 5.989 | 14.7457 | 383 | 166 | 3.2 | 2008 | 3.7 | 0.203 |
| 3 | 7.393 | 11.9482 | 264 | 1203 | 23 | 11688 | 21.5 | 0.163 |
| 4 | 9.814 | 9.0053 | 173 | 152 | 2.9 | 1726 | 3.2 | 0.19 |
| 5 | 11.14 | 7.936 | 169 | 46 | 0.9 | 527 | 1 | 0.192 |
| 6 | 11.612 | 7.6141 | 162 | 165 | 3.2 | 3343 | 6.2 | 0.34 |
| 7 | 14.204 | 6.2304 | 153 | 79 | 1.5 | 1319 | 2.4 | 0.28 |
| 8 | 14.473 | 6.1151 | 147 | 148 | 2.8 | 3587 | 6.6 | 0.406 |
| 9 | 14.807 | 5.9778 | 150 | 253 | 4.8 | 4322 | 8 | 0.286 |
| 10 | 15.042 | 5.8848 | 161 | 92 | 1.8 | 3356 | 6.2 | 0.612 |
| 11 | 16.187 | 5.4712 | 140 | 315 | 6 | 4790 | 8.8 | 0.255 |
| 12 | 18.499 | 4.7923 | 186 | 184 | 3.5 | 4248 | 7.8 | 0.387 |
| 13 | 18.933 | 4.6835 | 141 | 187 | 3.6 | 9242 | 17 | 0.829 |
| 14 | 19.287 | 4.5982 | 174 | 226 | 4.3 | 5022 | 9.3 | 0.373 |
| 15 | 19.66 | 4.5117 | 180 | 108 | 2.1 | 1002 | 1.8 | 0.156 |
| 16 | 20.863 | 4.2542 | 122 | 246 | 4.7 | 3836 | 7.1 | 0.261 |
| 17 | 22.48 | 3.9517 | 117 | 100 | 1.9 | 1330 | 2.5 | 0.223 |
| 18 | 23.292 | 3.8159 | 114 | 134 | 2.6 | 2038 | 3.8 | 0.255 |
| 19 | 26.245 | 3.3928 | 97 | 46 | 0.9 | 1096 | 2 | 0.399 |
| 20 | 26.504 | 3.3602 | 97 | 50 | 1 | 1096 | 2 | 0.367 |
| 21 | 27.841 | 3.2018 | 102 | 70 | 1.3 | 1576 | 2.9 | 0.377 |
| 22 | 28.477 | 3.1317 | 118 | 50 | 1 | 550 | 1 | 0.184 |
| 23 | 34.215 | 2.6185 | 78 | 39 | 0.7 | 906 | 1.7 | 0.389 |

Further, in some embodiments of the present disclosure, the aforesaid crystal form K of the compound of Formula (IV) has an XRPD pattern as shown in FIG. 31.

In some embodiments of the present disclosure, the aforesaid crystal form K of the compound of Formula (IV) has a differential scanning calorimetry curve as shown in FIG. 32.

In some embodiments of the present disclosure, the aforesaid crystal form K of the compound of Formula (IV) has a thermogravimetric analysis curve with a weight loss of 3.442% at 83.69° C.±3° C. and a weight loss of up to 4.947% at 183.76° C.±3° C.; and further, in some embodiments of the present disclosure, the aforesaid crystal form K of the compound of Formula (IV) has a TGA pattern as shown in FIG. 33.

In some embodiments of the present disclosure, in the aforesaid crystal forms H and K of the compound of Formula (IV), the compound of Formula (IV) has a structural formula of Compound IV-1.

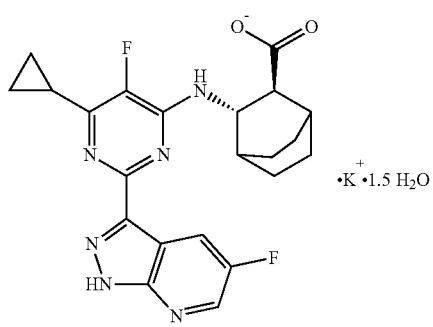

(IV-1)

In some embodiments of the present disclosure, in the aforesaid crystal forms I and J of the compound of Formula (IV), the compound of Formula (IV) has a structural formula of Compound IV-2.

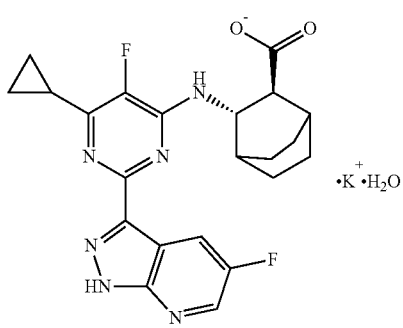

(IV-2)

The fifth object of the present disclosure is to further provide a compound of Formula (V) as below and its crystal forms,

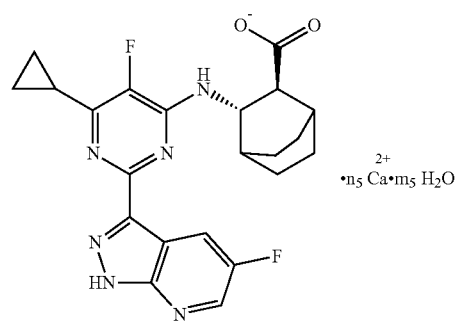

(V)

wherein, $n_5$ is selected from 0.5 and 1;
$m_5$ is selected from 0, 0.5, 1, 1.5, 2, 2.5, 3, 3.5 and 4.

In particular, the present disclosure further provides the crystal form L of the compound of Formula (V) having an X-ray powder diffraction pattern with characteristic diffraction peaks at 2θ angles of 10.39±0.2°, 18.04±0.2°, 20.31±0.2°; and further, the aforesaid crystal form L of the compound of Formula (V) has an X-ray powder diffraction pattern with characteristic diffraction peaks at 2θ angles of 7.91±0.2°, 10.39±0.2°, 14.18±0.2°, 16.01±0.2°, 16.47±0.2°, 18.04±0.2°, 20.31±0.2°, 21.91±0.2°. Further, in some embodiments of the present disclosure, the aforesaid crystal form L of the compound of Formula (V) may have XRPD analysis data as shown in Table 12. Persons skilled in the art can understand that as compared with the peak height with higher volatility, the 2θ value in XRPD analysis data is more suitable for characterization of the crystal form due to its smaller volatility.

TABLE 12

XRPD analysis data of the crystal form L of the compound of Formula (V)

| # | 2θ (±0.2°) | d (Å) | Background | Peak Height | Peak Height % | Area | Area % | Full Width at Half Maximum |
|---|---|---|---|---|---|---|---|---|
| 1 | 7.906 | 11.174 | 247 | 286 | 45.5 | 4309 | 38.8 | 0.253 |
| 2 | 10.393 | 8.5049 | 174 | 620 | 98.7 | 9862 | 88.8 | 0.267 |
| 3 | 11.788 | 7.501 | 154 | 51 | 8.1 | 1053 | 9.5 | 0.346 |
| 4 | 13.626 | 6.4933 | 143 | 77 | 12.3 | 1250 | 11.3 | 0.272 |
| 5 | 14.18 | 6.2406 | 141 | 254 | 40.4 | 4469 | 40.2 | 0.295 |
| 6 | 15.049 | 5.8822 | 133 | 62 | 9.9 | 527 | 4.7 | 0.143 |
| 7 | 15.774 | 5.6133 | 137 | 143 | 22.8 | 4449 | 40.1 | 0.522 |
| 8 | 16.012 | 5.5306 | 144 | 248 | 39.5 | 5255 | 47.3 | 0.355 |
| 9 | 16.466 | 5.379 | 160 | 195 | 31.1 | 1815 | 16.3 | 0.156 |
| 10 | 17.164 | 5.1617 | 164 | 54 | 8.6 | 293 | 2.6 | 0.091 |
| 11 | 18.044 | 4.9121 | 153 | 628 | 100 | 11105 | 100 | 0.296 |
| 12 | 19.86 | 4.4669 | 158 | 112 | 17.8 | 1477 | 13.3 | 0.221 |
| 13 | 20.311 | 4.3687 | 131 | 289 | 46 | 8238 | 74.2 | 0.478 |
| 14 | 20.829 | 4.2612 | 166 | 144 | 22.9 | 1527 | 13.8 | 0.178 |
| 15 | 21.91 | 4.0532 | 137 | 319 | 50.8 | 4936 | 44.4 | 0.259 |
| 16 | 22.538 | 3.9418 | 139 | 202 | 32.2 | 3490 | 31.4 | 0.29 |
| 17 | 23.194 | 3.8318 | 122 | 132 | 21 | 1332 | 12 | 0.169 |
| 18 | 24.59 | 3.6173 | 141 | 81 | 12.9 | 503 | 4.5 | 0.104 |
| 19 | 25.124 | 3.5416 | 138 | 145 | 23.1 | 2721 | 24.5 | 0.315 |
| 20 | 25.417 | 3.5014 | 149 | 59 | 9.4 | 1526 | 13.7 | 0.434 |
| 21 | 25.894 | 3.438 | 141 | 71 | 11.3 | 1080 | 9.7 | 0.255 |
| 22 | 26.35 | 3.3795 | 122 | 149 | 23.7 | 2310 | 20.8 | 0.26 |
| 23 | 28.104 | 3.1725 | 108 | 131 | 20.9 | 3172 | 28.6 | 0.406 |
| 24 | 28.632 | 3.1151 | 113 | 136 | 21.7 | 2515 | 22.6 | 0.31 |
| 25 | 29.821 | 2.9936 | 91 | 38 | 6.1 | 817 | 7.4 | 0.36 |
| 26 | 31.395 | 2.847 | 98 | 115 | 18.3 | 3227 | 29.1 | 0.47 |

TABLE 12-continued

XRPD analysis data of the crystal form
L of the compound of Formula (V)

| # | 2θ (±0.2°) | d (Å) | Background | Peak Height | Peak Height % | Area | Area % | Full Width at Half Maximum |
|---|---|---|---|---|---|---|---|---|
| 27 | 32.48 | 2.7543 | 97 | 40 | 6.4 | 294 | 2.6 | 0.123 |
| 28 | 34.257 | 2.6154 | 88 | 61 | 9.7 | 1095 | 9.9 | 0.301 |
| 29 | 35.399 | 2.5336 | 84 | 42 | 6.7 | 1052 | 9.5 | 0.42 |
| 30 | 39.383 | 2.286 | 73 | 43 | 6.8 | 754 | 6.8 | 0.294 |

In some embodiments of the present disclosure, the aforesaid crystal form L of the compound of Formula (V) has an XRPD pattern as shown in FIG. 34.

In some embodiments of the present disclosure, the aforesaid crystal form L of the compound of Formula (V) has a differential scanning calorimetry curve with an endothermic peak at 168.08° C.±3° C., and a starting point of an endothermic peak at 204.17° C.±3° C.; and further, in some embodiments of the present disclosure, the aforesaid crystal form L of the compound of Formula (V) has a DSC pattern as shown in FIG. 35.

In some embodiments of the present disclosure, the aforesaid crystal form L of the compound of Formula (V) has a thermogravimetric analysis curve with a weight loss of 0.830% at 80.19° C.±3° C., a weight loss of up to 3.058% at 149.87° C.±3° C., and a weight loss of up to 4.648% at 201.25° C.±3° C.; and further, in some embodiments of the present disclosure, the aforesaid crystal form L of the compound of Formula (V) has a TGA pattern as shown in FIG. 36.

Further, in some embodiments of the present disclosure, in the aforesaid crystal form L of the compound of Formula (V), the compound of Formula (V) is Compound V-1.

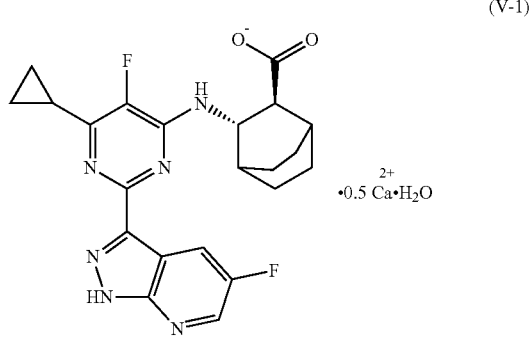

(V-1)

The present disclosure further provides use of the aforesaid crystal forms in preparation of anti-influenza drugs.

Technical Effect

The crystal forms provided in the present disclosure have good stability, low moisture absorption, and good prospect as drugs.

In particular, the present disclosure provides free form, potassium salt form, sodium salt form, calcium salt form, hydrochloride salt form, and tosylate salt form of a pyrazolopyridine compound, as well as crystal forms corresponding to the free form and various salt forms. Further experiments indicate that the resultant crystal forms of the free form and the various salt forms all have relatively high stability, and show that the impurity content does not change significantly during storage at high temperature and high humidity, and the crystal forms remain substantially unchanged, and thus it appears that these crystal forms have better properties for drug formation; in addition, for some of the aforesaid crystal forms, they can also be used as intermediate crystal forms to prepare other stable crystal forms.

In addition, the compounds of the present disclosure also show positive effects in the tests of inhibiting influenza virus replication at cellular level, and the corresponding salt forms and their crystal forms can be understood to also have positive effects that are substantially consistent with the free form of the compounds.

Definitions and Explanations

Unless otherwise stated, the following terms and phrases as used herein are intended to have the following meanings. A specific phrase or term should not be deemed indefinite or unclear without specific definition, but understood in accordance with its ordinary meaning. When a trade name is used herein, it is intended to refer to the corresponding commercial product or its active ingredient.

The intermediate compounds of the present disclosure can be prepared by various synthetic methods which are well known to those skilled in the art, including the specific embodiments as listed below, the embodiments formed by combining the specific embodiments with other chemical synthesis methods, and equivalent alternatives which are well known to those skilled in the art. The preferred embodiments include, but are not limited to, the examples of the present disclosure.

The chemical reactions of the specific embodiments of the present disclosure are performed in suitable solvent(s) which must be suitable for the chemical changes of the present disclosure and the required reagents and materials. In order to obtain the compounds of the present disclosure, those skilled in the art sometimes need to modify or select the synthesis steps or the reaction schemes based on the existing embodiments.

Hereinafter the present disclosure will be described in details by ways of examples. These examples are not intended to limit the present disclosure in any manner.

All the solvents used in the present disclosure are commercially available, and can be used without further purification.

The following abbreviates are used in the present disclosure: DMF represents dimethylformamide; MsOH represents methanesulfonic acid; EtOH represents ethanol; and NaOH represents sodiumhydroxide.

The compounds are named manually or by ChemDraw® software, while commercially available compounds are used with their supplier catalog names.

X-Ray Powder Diffractometer (XRPD) Method of the Present Disclosure

Instrument Model: Bruker D8 advance X-ray diffractometer

Detection Method: About 10-20 mg of sample is used in XRPD detection.

Detailed XRPD parameters are as follows:
Light Tube: Cu, kα, (λ=1.54056 Å).
Light Tube Voltage: 40 kV, Light Tube Current: 40 mA
Divergence Slit: 0.60 mm
Detector Slit: 10.50 mm
Anti-Scatter Slit: 7.10 mm
Scanned Range: 4-40 deg Step Size: 0.02 deg
Step Length: 0.12 sec
Rotating Speed of Sample Disc: 15 rpm Differential Scanning Calorimeter (DSC) Method of the Present Disclosure Instrument Model: TA Q2000 differential scanning calorimeter Detection Method: A sample (~1 mg) is placed in a DSC aluminum pot for detection, for which the sample is heated from 30° C. to 280° C., at a heating rate of 10° C./min, under the condition of 50 mL/min N2.

Thermal Gravimetric Analyzer (TGA) Method of the Present Disclosure

Instrument Model: TA Q5000IR thermal gravimetric analyzer

Detection Method: A sample (2-5 mg) is placed in a TGA platinum pot for detection, for which the sample is heated from room temperature to 300° C., at a heating rate of 10° C./min, under the condition of 25 mL/min N2.

High Performance Liquid Chromatograph (HPLC)

The analytic method is as follows:

TABLE 13

Detection and Analysis Method of Content of Crystal Form A and Related Materials

| | |
|---|---|
| Instrument | Agilent 1200 High Performance Liquid Chromatograph |
| Column | Ascentis Express C18, 4.6 × 150 mm, 2.7 μm (94#) |
| Mobile Phase A | 0.1% aqueous solution of phosphoric acid |
| Mobile Phase B | Acetonitrile solution |
| Flowrate | 1.2 mL/min |
| Injection Volume | 5.0 μL |
| Detection Wavelength | 210 nm |
| Column Temperature | 40° C. |
| Diluent | Acetonitrile:pure water = 3/1 (v/v) |
| Sample Concentration | 0.5 mg/mL |

| Gradient Elution Procedure | Time (min) | Mobile Phase A (%) | Mobile Phase B (%) |
|---|---|---|---|
| | 0.00 | 85 | 15 |
| | 25.00 | 5 | 95 |
| | 27.00 | 5 | 95 |
| | 27.01 | 85 | 15 |
| | 30.00 | 85 | 15 |

TABLE 14

Detection and Analysis Method of Content of Crystal Form B and Related Materials

| | |
|---|---|
| Instrument | Agilent 1200 High Performance Liquid Chromatograph |
| Column | Agilent Eclipse plus C18, 4.6 × 150 mm, 3.5 μm (150#) |
| Mobile Phase A | 0.04% aqueous solution of trifluoroacetic acid |
| Mobile Phase B | Acetonitrile solution |
| Flowrate | 1.0 mL/min |
| Injection Volume | 10.0 μl |
| Detection Wavelength | 220 nm |
| Column Temperature | 40° C. |
| Diluent | Ethanol-water (80:20) |
| HPLC save path: | E:\ PDS-NDL\ 2017\Formulation internal\FL056 |

| Gradient Elution Procedure | Time (min) | Mobile Phase A (%) | Mobile Phase B (%) |
|---|---|---|---|
| | 0.00 | 90 | 10 |
| | 50.00 | 10 | 90 |
| | 55.00 | 10 | 90 |
| | 55.01 | 90 | 10 |
| | 60.00 | 90 | 10 |

BRIEF DESCRIPTION OF THE DRAWINGS

FIG. 11: A DSC pattern of the crystal form D;
FIG. 12: A TGA pattern of the crystal form D.

DETAILED DESCRIPTION

Figure 1:
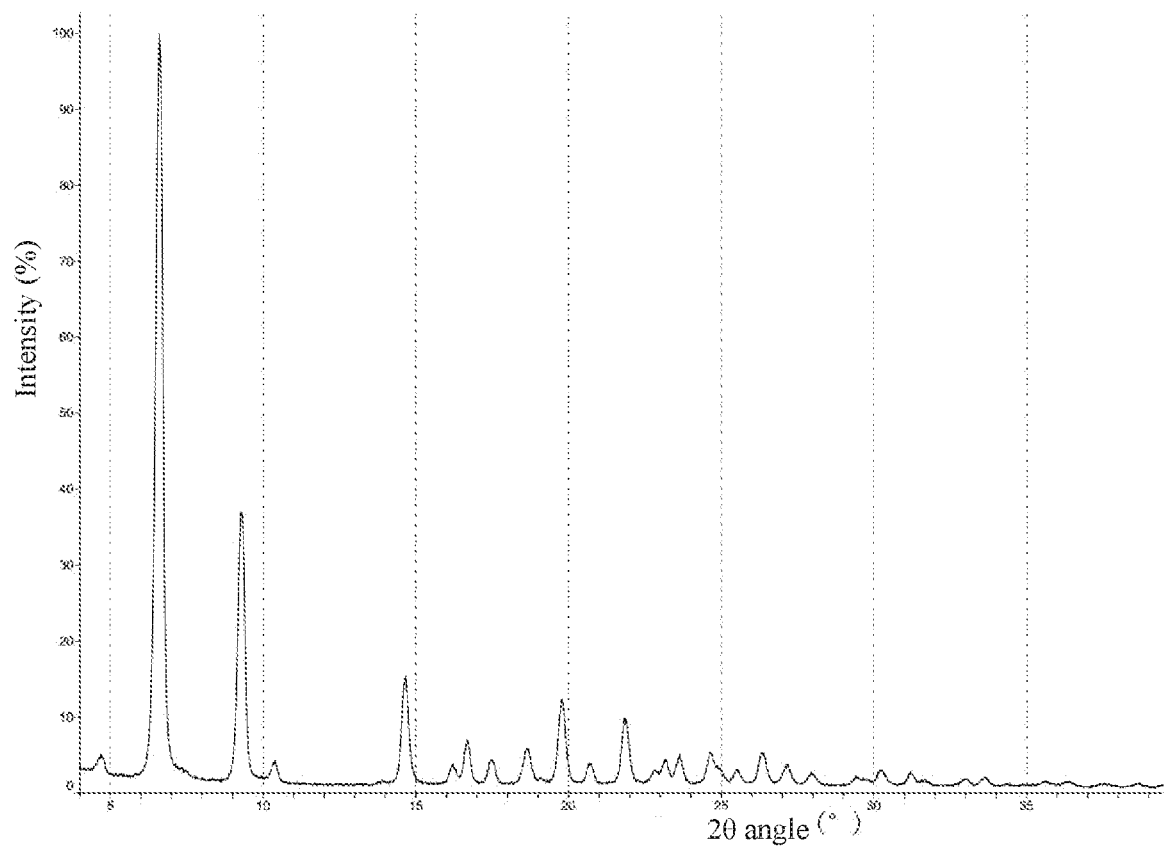
FIG. 1: A Cu-Kα radiated XRPD pattern of the crystal form A.

To better understand the present disclosure, hereinafter it is further described by reference to specific examples. However, the present disclosure is not limited to the specific embodiments.

Reference Example 1: Preparation of Compound BB-1

Step 1: Synthesis of Compound BB-1-2:

To a solution of Compound BB-1-1 (300 mg, 1.97 mmol) in bromoform (5 mL) was added t-butyl nitrite (406 mg, 3.94 mmol). The mixture was stirred at 60° C. for 1 hr, and then stirred at 90° C. for 1 hr. The reaction mixture was cooled to room temperature, and concentrated to give a crude product, which was purified by flash chromatography with silica gel (5-20% ethyl acetate/petroleum ether) to give Compound BB-1-2 (300.00 mg, yield: 70.50%). $^1$H NMR (400 MHz, CDCl$_3$) δ: 11.25 (br s, 1H), 8.54 (dd, J=1.88, 2.64 Hz, 1H), 7.69 (dd, J=2.51, 7.28 Hz, 1H). MS (ESI) m/z: 215.9 (M+H$^+$).

Step 2: Synthesis of Compound BB-1-3:

To a solution of Compound BB-1-2 (300 mg, 1.39 mmol) in N,N-dimethylformamide (5 mL) was added triphenylmethyl chloride (426 mg, 1.53 mmol) and potassium carbonate (576 mg, 4.17 mmol). The mixture was stirred at 25° C. for 12 hrs. The reaction mixture was diluted with ethyl acetate (50 mL), and washed with saturated brine (15 mL×3). The organic phase was dried over anhydrous sodium sulfate, concentrated to give a crude product, which was purified by flash chromatograph with silica gel (0-10% ethyl acetate/petroleum ether) to give Compound BB-1-3 (350 mg, yield: 54.94%). $^1$H NMR (400 MHz, CDCl$_3$) δ: 8.16 (dd, J=1.25, 2.76 Hz, 1H), 7.53 (dd, J=3.01, 7.53 Hz, 1H), 7.25 (s, 15H). MS (ESI) m/z: 458.2 (M+H$^+$).

Step 3: Synthesis of Compound BB-1:

To a solution of Compound BB-1-3 (350 mg, 763.66 µmol) and Bis(pinacolato)diboron (291 mg, 1.15 mmol) in N,N-dimethylformamide (7 mL) was added potassium acetate (225 mg, 2.29 mmol) and r-bis(di-tert-butylphosphine) palladium ferrocene dichloride (28 mg, 38.18 μmol). The mixture was stirred at 100° C. under nitrogen protection for 2 hr. The reaction mixture was cooled to room temperature and then filtered. The filtrate was diluted with ethyl acetate (50 mL), and washed with saturated brine (20 mL×3). The organic phase was dried over anhydrous sodium sulfate, and concentrated to give a crude product, which was purified by flash chromatograph with silica gel (0-10% ethyl acetate/petroleum ether) to give BB-1 (300 mg, yield: 77.73%). MS (ESI) m/z: 733.2 (M+Na$^+$).

Example 1: Preparation of Compound 1

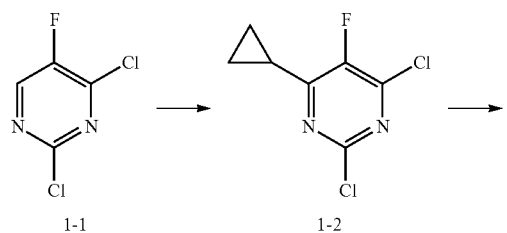

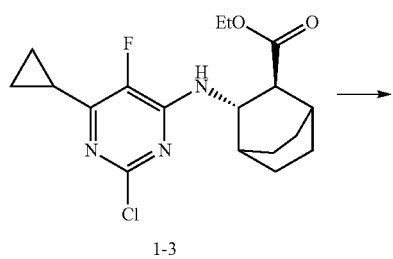

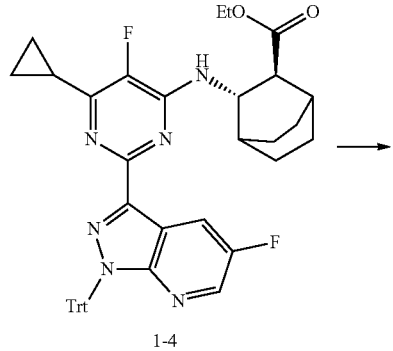

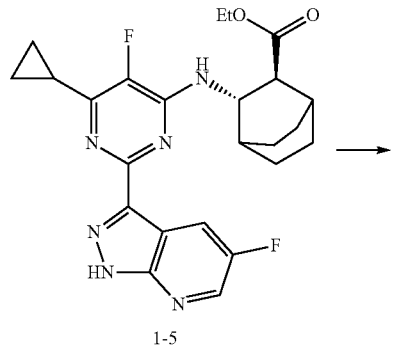

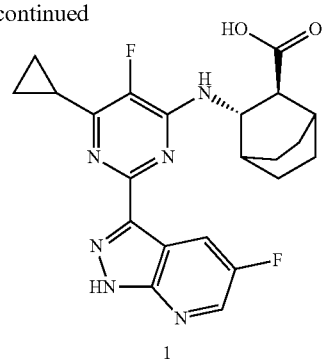

1

Step 1: Synthesis of Compound 1-2

At 0° C., Compound 1-1 (25.00 g, 149.73 mmol) was dissolved into glycol dimethyl ether (80 mL), and cyclopropylmagnesium bromide (0.5 M, 500.10 mL) was dropwise added. The reaction mixture was stirred at room temperature overnight. Then, the reaction mixture was cooled to 0° C., and a solution of triethylamine (15.15 g, 149.73 mmol, 20.75 mL) in tetrafuran (30 mL) and a solution of iodine (38.00 g, 149.73 mmol) in tetrafuran (30 mL) were respectively added. The reaction mixture was stirred at room temperature for 3 hr. To the reaction mixture was added ethyl acetate (1 L), washed with water (300 mL×3) and saturated brine (300 mL), respectively, dried over anhydrous sodium sulfate, filtered and concentrated under reduced pressure. The obtained crude product was purified by silica gel column (petroleum ether) to give Compound 1-2 (8 g, yield: 25.8%).

Step 2: Synthesis of Compound 1-3

Compound (2S,3S)-ethyl 3-aminobiscyclo[2.2.2]octane-2-carboxylate (450 mg, 2.28 mmol) and Compound 1-2 (450 mg, 2.17 mmol) were dissolved into tetrahydrofuran (5.00 mL), and diisopropylethylamine (841.35 mg, 6.51 mmol) was added. The reaction mixture was stirred at 55° C. for 3 hr. The reaction mixture was concentrated under reduced pressure, and the crude product was purified by flash column with silica gel (petroleum ether: ethyl acetate=10:1 to 5:1) to give Compound 1-3 (460.00 mg, yield: 57.6%).

Step 3: Synthesis of Compound 1-4

At room temperature, Compounds 1-3 (460.00 mg, 1.25 mmol) and BB-1 (1.05 g, 1.25 mmol) were dissolved into 2-methyltetrahydrofuran (8.00 mL) and water (2.00 mL), and potassium phosphate (796.34 mg, 3.75 mmol), tri (dibenzalacetone)dipalladium (114.51 mg, 125.05 μmol) and 2-biscyclohexylphosphine-2',4',6'-triisopropylbiphenyl (119 mg, 250 μmol) were respectively added. The reaction mixture was reacted at 80° C. overnight. The reaction mixture was cooled to room temperature, and water (30 mL) was added. Then, the mixture was filtered, and the filtrate was extracted with ethyl acetate (10 mL×3). The organic phases were combined, and dried over anhydrous sodium sulfate, filtered and concentrated under reduced pressure. The obtained crude product was purified by flash column with silica gel (petroleum ether: ethyl acetate=20:1 to 3:1) to give Compound 1-4 (600 mg, yield: 61%). MS (ESI) m/z: 773.4 (M+H$^+$).

Step 4: Synthesis of Compound 1-5

At room temperature, Compound 1-4 (600.00 mg, 844.11 μmol) was dissolved into dichloromethane (6.00 mL), and trifluoroacetic acid (962.45 mg, 8.44 mmol) and triethyl hydrosilane (981.53 mg, 8.44 mmol) were added. The reaction mixture was reacted at room temperature for 4 hr. The reaction mixture was concentrated under reduced pressure, and the obtained crude product was purified by flash column with silica gel (petroleum ether: ethyl acetate=10:1 to 2:1) to give Compound 1-5 (350.00 mg, yield: 87.6%). MS (ESI) m/z: 469.2 (M+H$^+$).

Step 5: Synthesis of Compound 1

At room temperature, Compound 1-5 (160.00 mg, 341.52 μmol) was dissolved into dioxane (3.00 mL) and water (500.00 μL), and sodium hydroxide (136.61 mg, 3.42 mmol) was added. The reaction mixture was reacted at 80° C. for 1 hr. The reaction mixture was concentrated under reduced pressure and then adjusted to pH=5 by adding 1 M HCl. The precipitated solid was filtered, and the filter cake was washed with water (10 mL), and dried to give 1 (55.4 mg, yield: 36.5%). $^1$H NMR (400 MHz, d$_4$-MeOH) δ 8.49-8.58 (m, 2H), 4.92 (br s, 1H), 2.78 (br d, J=6.78 Hz, 1H), 2.22-2.31 (m, 1H), 2.11 (br s, 1H), 1.80-2.02 (m, 4H), 1.61-1.77 (m, 3H), 1.44-1.59 (m, 2H), 1.25-1.34 (m, 3H), 1.03-1.11 (m, 2H). MS m/z: 441.1 [M+1]$^+$.

Figure 2:
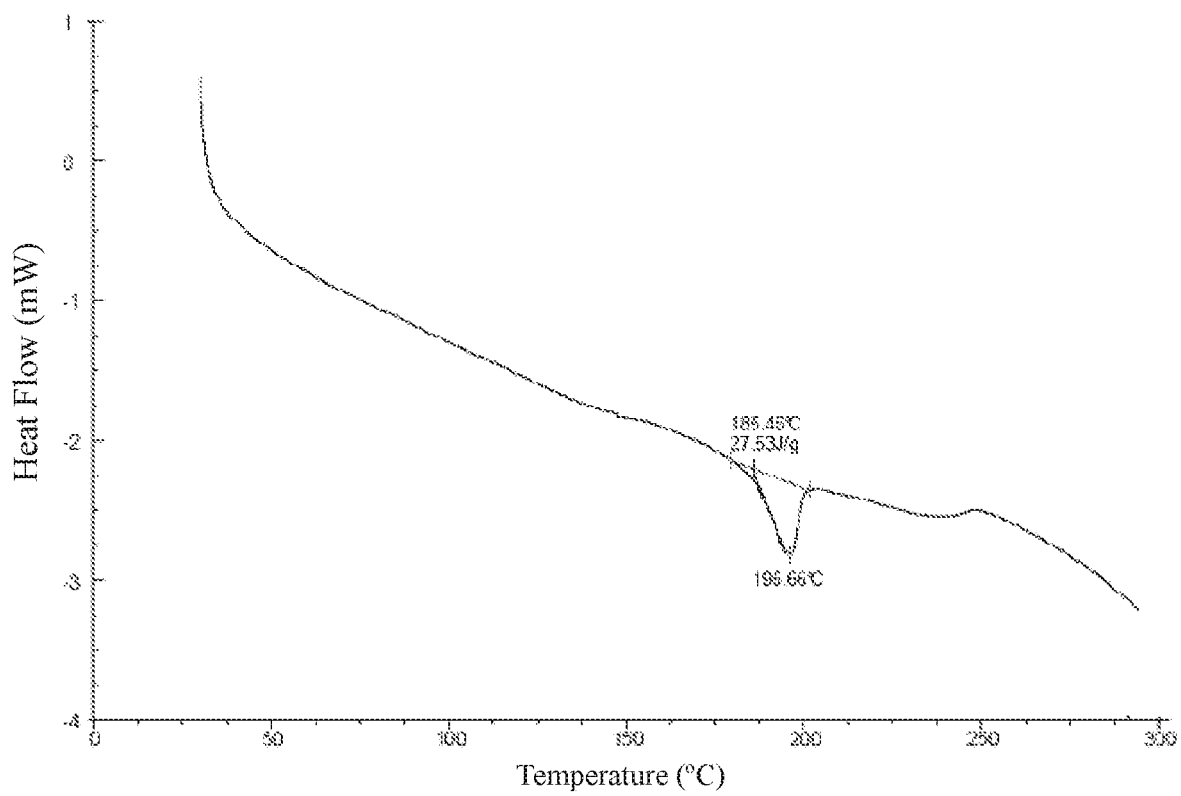
FIG. 2: A DSC pattern of the crystal form A.
Figure 3:
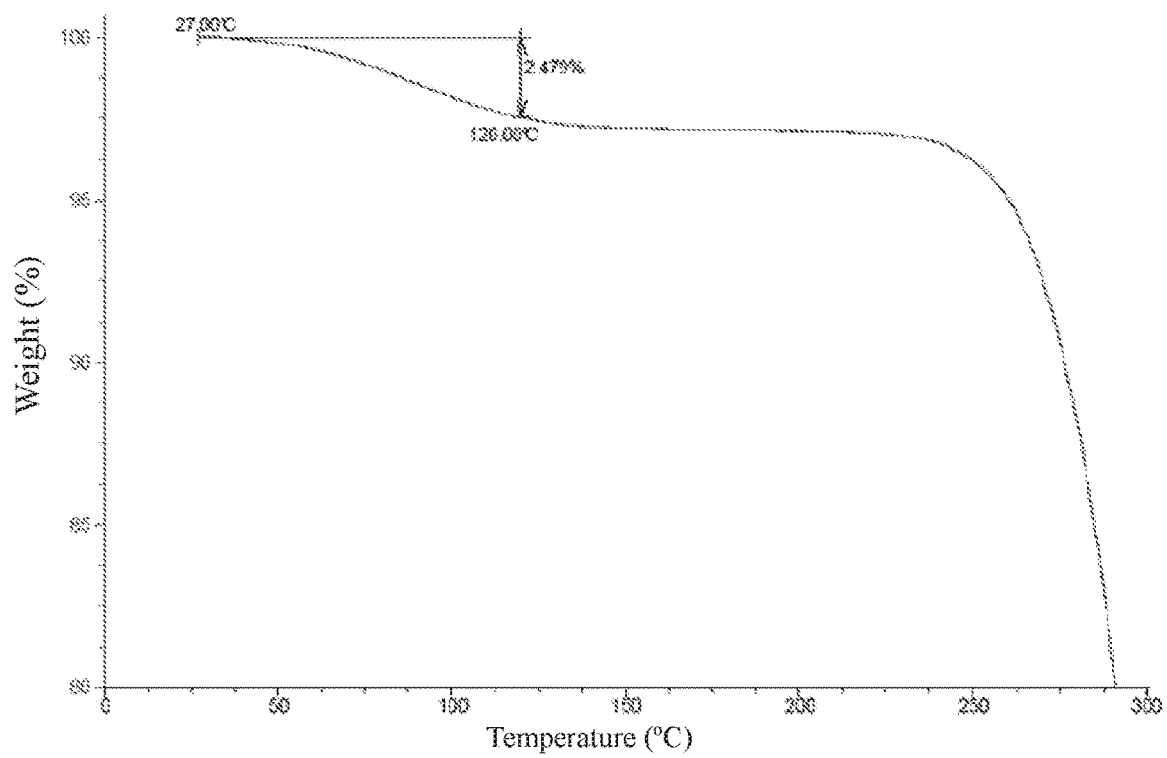
FIG. 3: A TGA pattern of the crystal form A.

Example 2: Preparation of Crystal Form A 100 mg of Compound 1 was placed into a glass flask, and 0.8 mL of ethanol was added to form a suspension. The suspension sample was placed in a thermomixer (40° C.) for conducting an experiment (in dark). The suspension sample was shaken at 40° C. for 60 hr, and centrifuged. Then, the residual sample was dried in a vacuum drying oven (40° C.) overnight, to give the crystal form A. The obtained crystal form A has an XRPD pattern as shown in FIG. 1, a DSC pattern as shown in FIG. 2, and a TGA pattern as shown in FIG. 3.

Example 3: Preparation of Crystal Form A 100 mg of Compound 1 was placed into a glass flask, and 1.2 mL of ethyl acetate was added to form a suspension. The suspension sample was placed in a thermomixer (40° C.) for conducting an experiment (in dark). The suspension sample was shaken at 40° C. for 60 hr, and centrifuged. Then, the residual sample was dried in a vacuum drying oven (40° C.) overnight, to give the crystal form A which was substantially consistent with that of Example 2.

Figure 4:
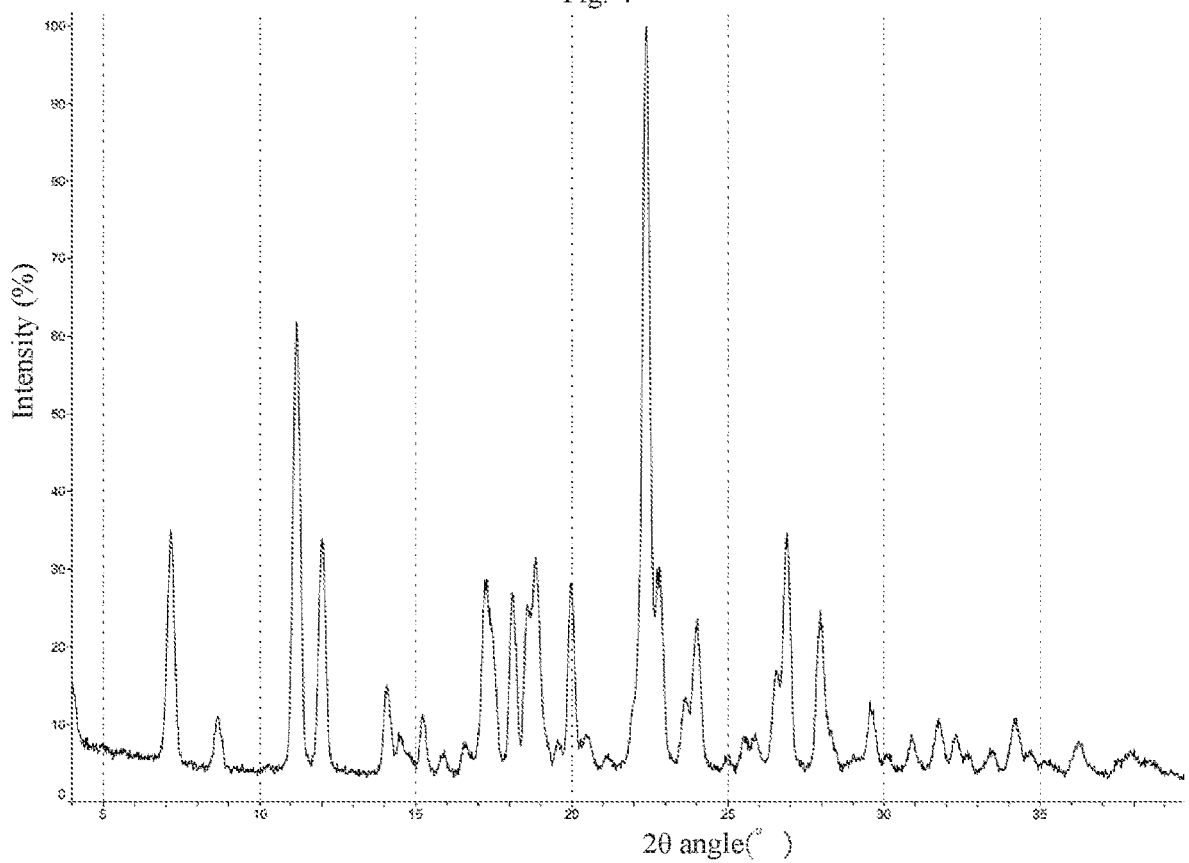
FIG. 4: A Cu-Kα radiated XRPD pattern of the crystal form B.
Figure 5:
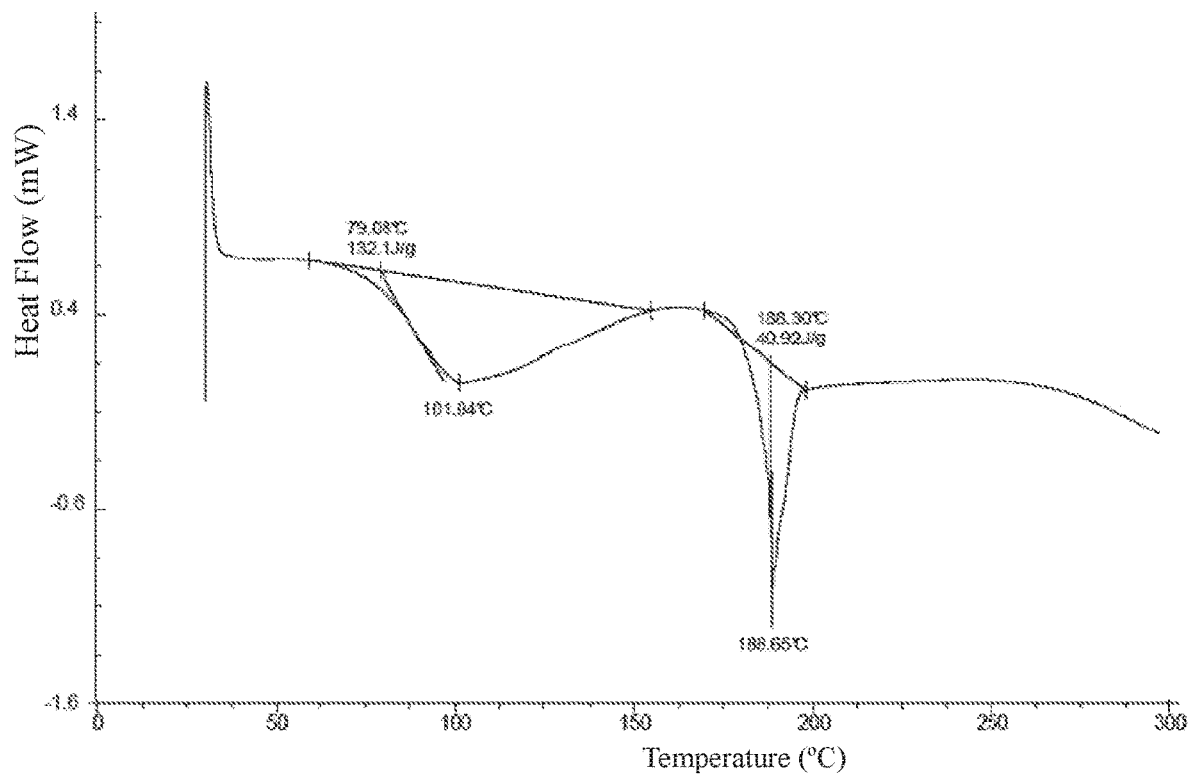
FIG. 5: A DSC pattern of the crystal form B.
Figure 6:
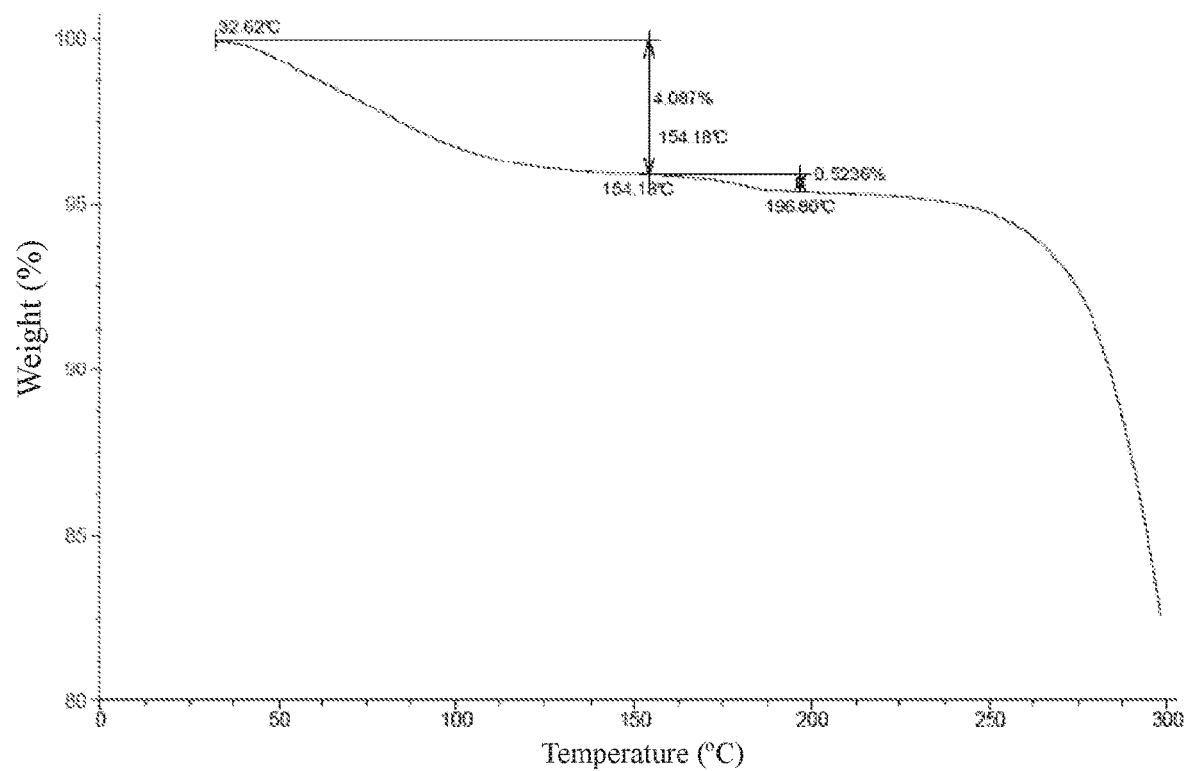
FIG. 6: A TGA pattern of the crystal form B.

Example 4: Preparation of Crystal Form B 66 g of Compound 1 was added into a mixed solution (600 mL) of ethanol and water (ethanol: water=1:1) to form a suspension. The suspension was placed on a stirrer, stirred at 40° C. for 48 hr, and filtered. The filter cake was oven-dried to give the crystal form B. The obtained crystal form B has an XRPD pattern as shown in FIG. 4, a DSC pattern as shown in FIG. 5, and a TGA pattern as shown in FIG. 6.

Example 5: Preparation Crystal Form B 66 g of Compound 1 was added into a mixed solution (600 mL) of ethanol and water (ethanol: water=3:1) to form a suspension. The suspension was placed on a stirrer and stirred at 40° C. for 48 hr, and filtered. The filter cake was oven-dried to give the crystal form B which was substantially consistent with that of Example 4.

Figure 7:
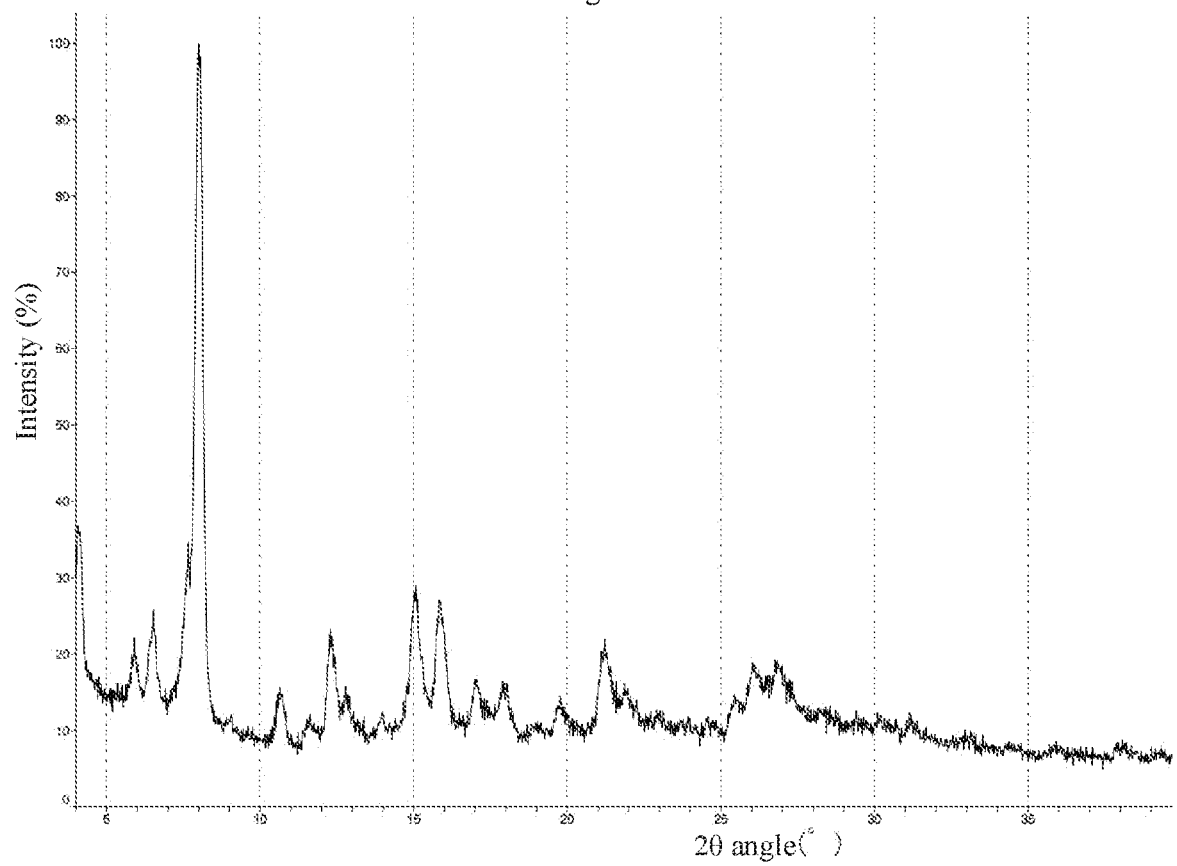
FIG. 7: A Cu-Kα radiated XRPD pattern of the crystal form C.
Figure 8:
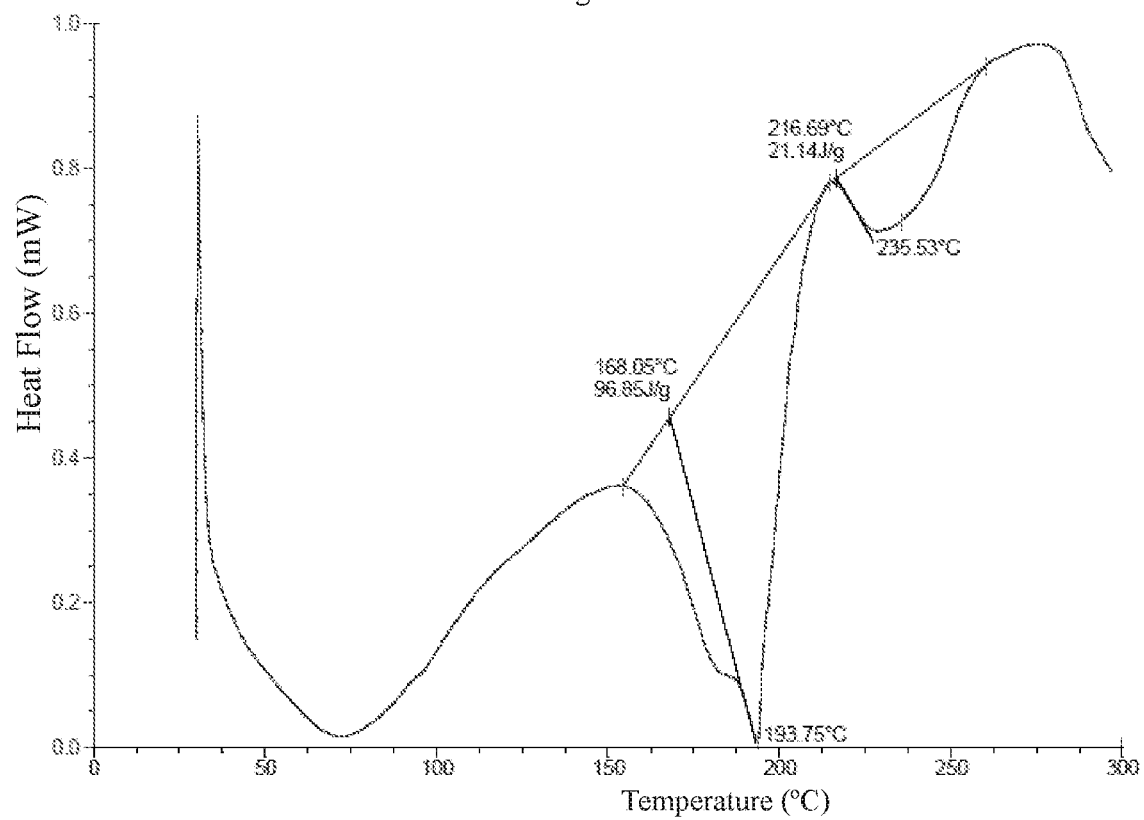
FIG. 8: A DSC pattern of the crystal form C.
Figure 9:
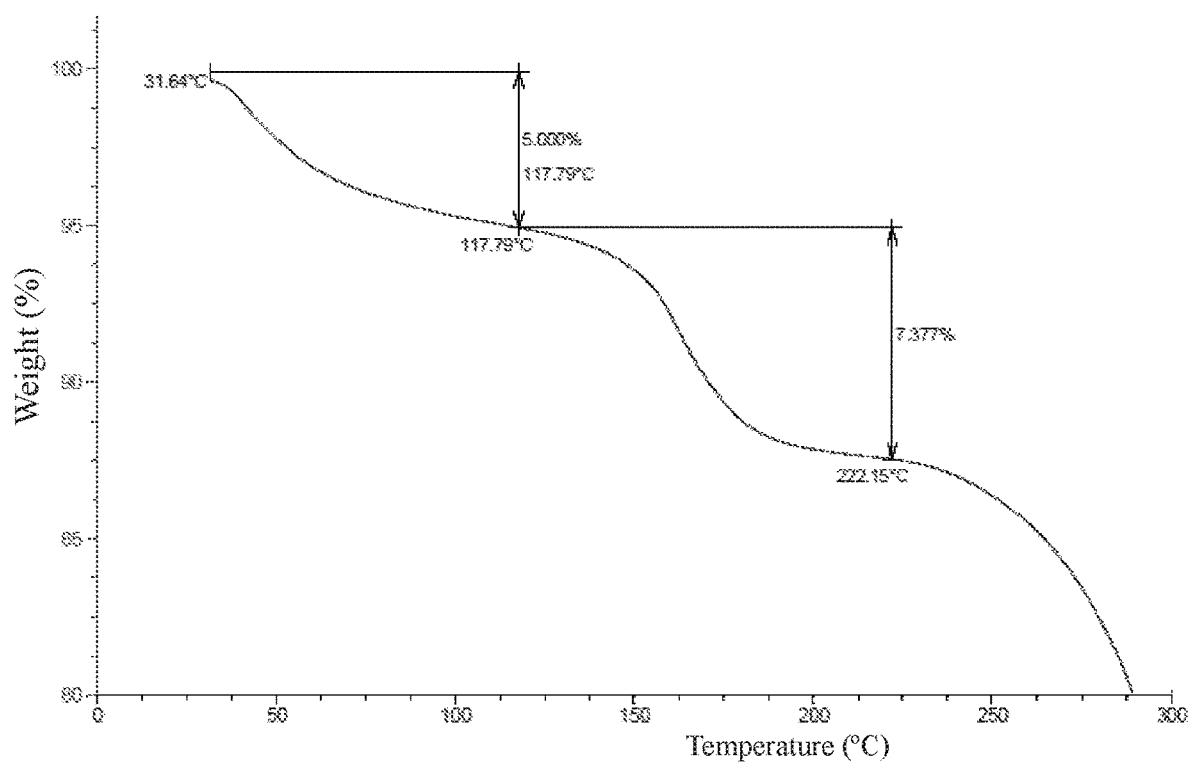
FIG. 9: A TGA pattern of the crystal form C.

Example 6: Preparation of Crystal Form C 5 g of Compound 1 was added into a 250 mL eggplant-shaped flask, THF (100 mL) was added, and hydrochloric acid (0.98 mL, dissolved in 9 mL THF) was added. The mixture was stirred at 30° C. for 12 hr, and the solid was filtered. The filter cake was dried under vacuum at 40° C. to give the crystal form C (4.29 g). The obtained crystal form C has an XRPD pattern as shown in FIG. 7, a DSC pattern as shown in FIG. 8, and a TGA pattern as shown in FIG. 9.

Example 7: Preparation of Crystal Form D

Figure 10:
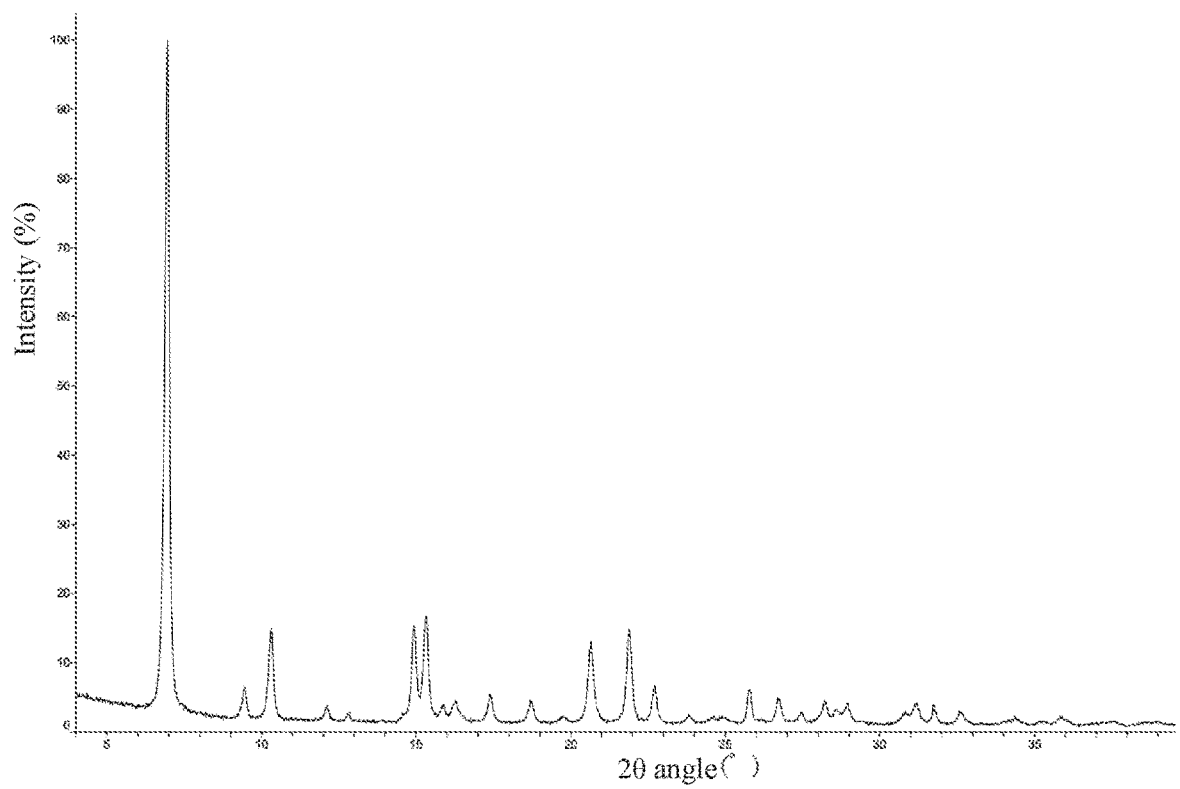
FIG. 10: A Cu-Kα radiated XRPD pattern of the crystal form D.

Crystal form C (0.201 g) was dissolved into acetonitrile (3 mL) and beaten. The mixture was stirred at 30° C. for 12 hr, and the solid was filtered. The filter cake was dried under vacuum at 40° C. to give the crystal form D. The obtained crystal form D has an XRPD pattern as shown in FIG. 10, a DSC pattern as shown in FIG. 11, and a TGA pattern as shown in FIG. 12.

Figure 13:
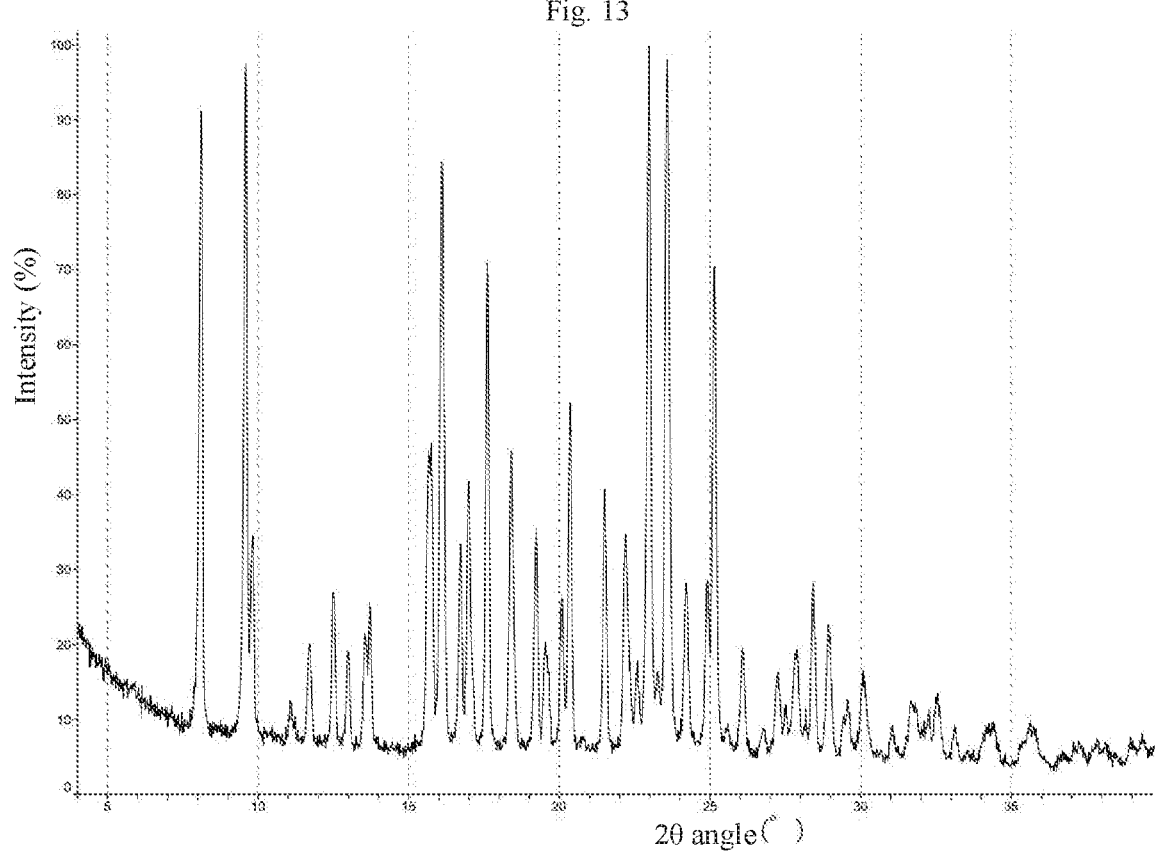
FIG. 13: A Cu-Kα radiated XRPD pattern of the crystal form E.
Figure 14:
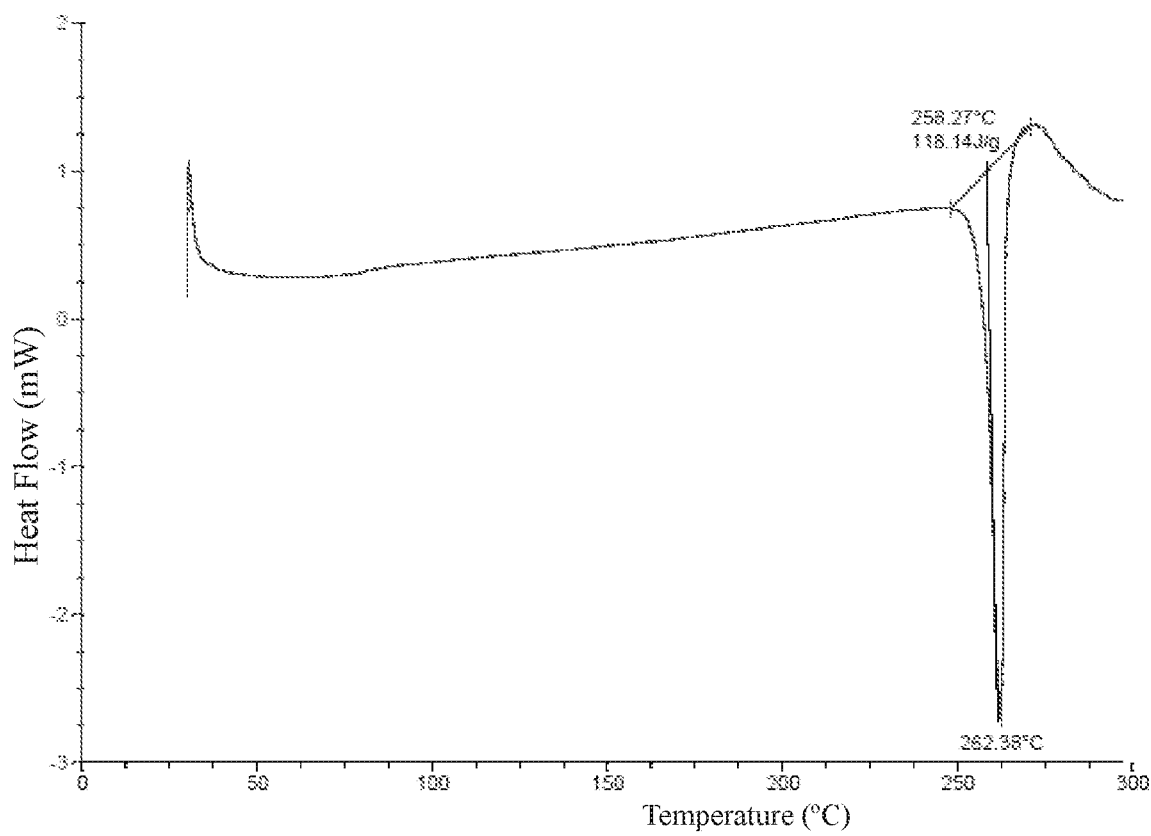
FIG. 14: A DSC pattern of the crystal form E.
Figure 15:
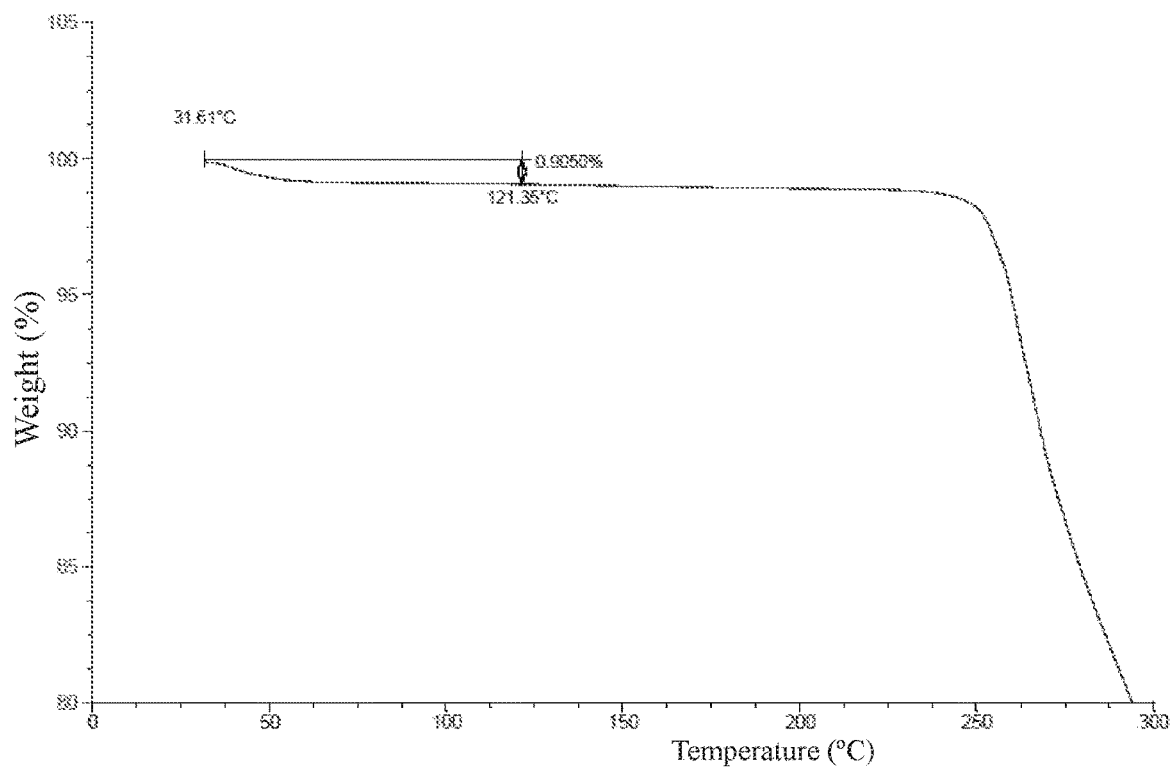
FIG. 15: A TGA pattern of the crystal form E.

Example 8: Preparation of Crystal Form E 5 g of Compound 1 was added into a 250 mL eggplant-shaped flask, THF (100 mL) was added, and p-toluenesulfonic acid monohydrate (2.26 g, dissolved in 10 mL THF) was added. The mixture was stirred at 30° C. for 12 hr, and the solid was filtered. The filter cake was dried under vacuum at 40° C. to give a solid (0.425 g). The solid (0.101 g) was added into acetone (2 mL) and beaten for 12h to give the crystal form E. The obtained crystal form E has an XRPD pattern as shown in FIG. 13, a DSC pattern as shown in FIG. 14, and a TGA pattern as shown in FIG. 15.

Figure 16:
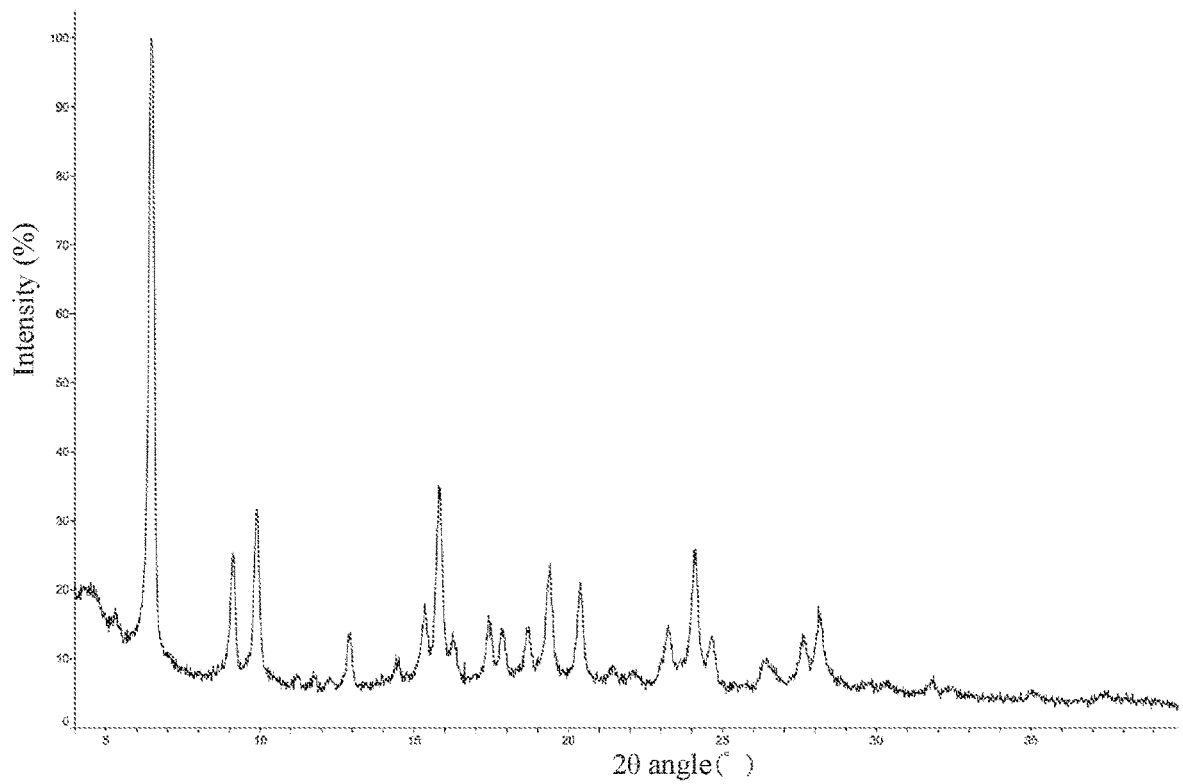
FIG. 16: A Cu-Kα radiated XRPD pattern of the crystal form F.
Figure 17:
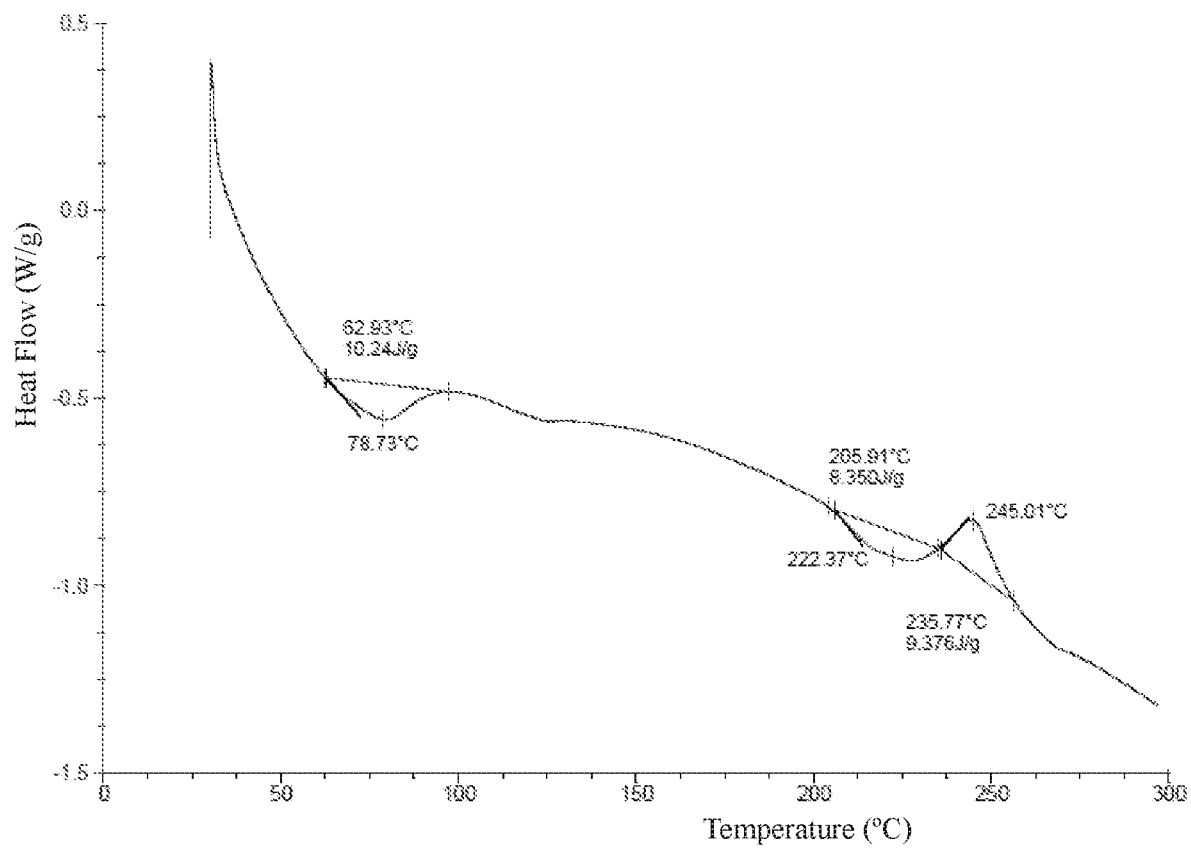
FIG. 17: A DSC pattern of the crystal form F.
Figure 18:
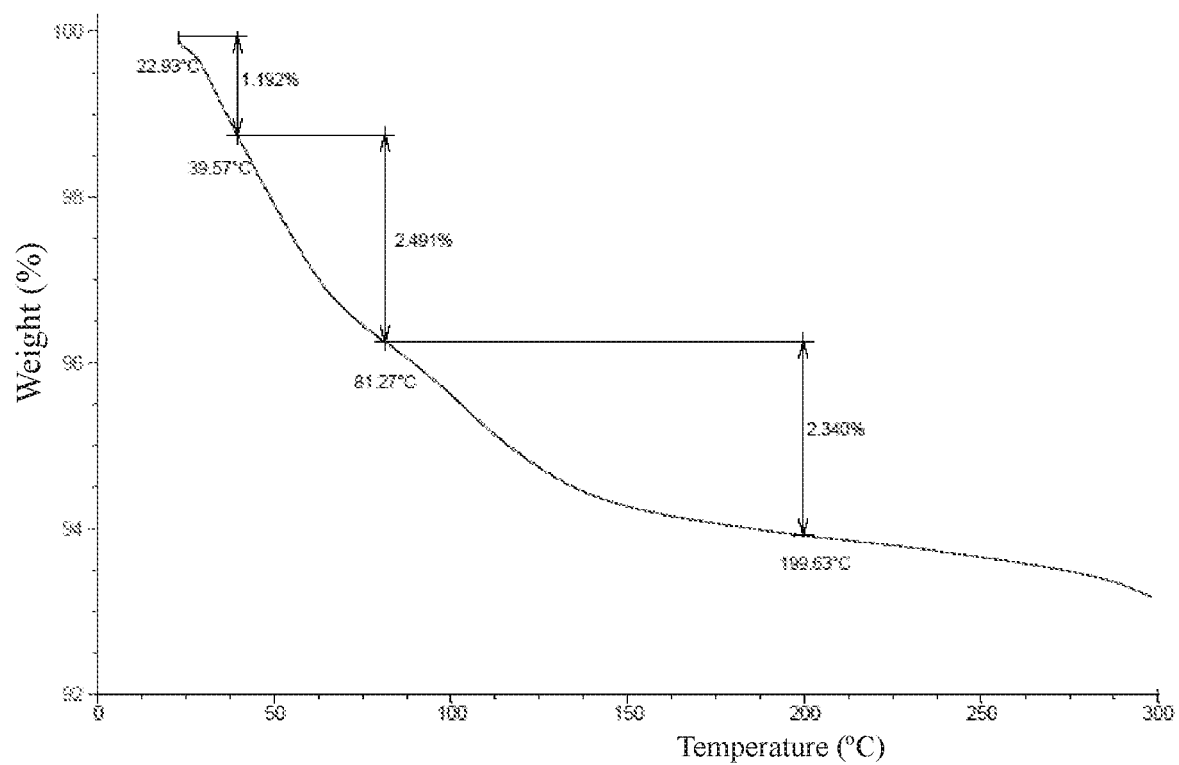
FIG. 18: A TGA pattern of the crystal form F.

Example 9: Preparation of Crystal Form F 5 g of Compound 1 was added into a 250 mL eggplant-shaped flask, THF (100 mL) was added, and an aqueous NaOH solution (0.477 g, dissolved in 1 mL water) was added. The mixture was stirred at 30° C. for 12 hr, and the solid was filtered. The filter cake was dried under vacuum at 40° C. to give the crystal form F. The obtained crystal form F has an XRPD pattern as shown in FIG. 16, a DSC pattern as shown in FIG. 17, and a TGA pattern as shown in FIG. 18.

Example 9-1: Preparation of Crystal Form F 202 mg of the crystal form F obtained in Example 9 was added into EtOH:H$_2$O=3:1 (4 mL). The mixture was stirred at 30° C. for 12 hr, and the solid was filtered. The filter cake was dried under vacuum at 40° C. to give the crystal form F. The obtained crystal form F was substantially consistent with the crystal form F of Example 9.

Example 10: Preparation of Crystal Form G

Figure 19:
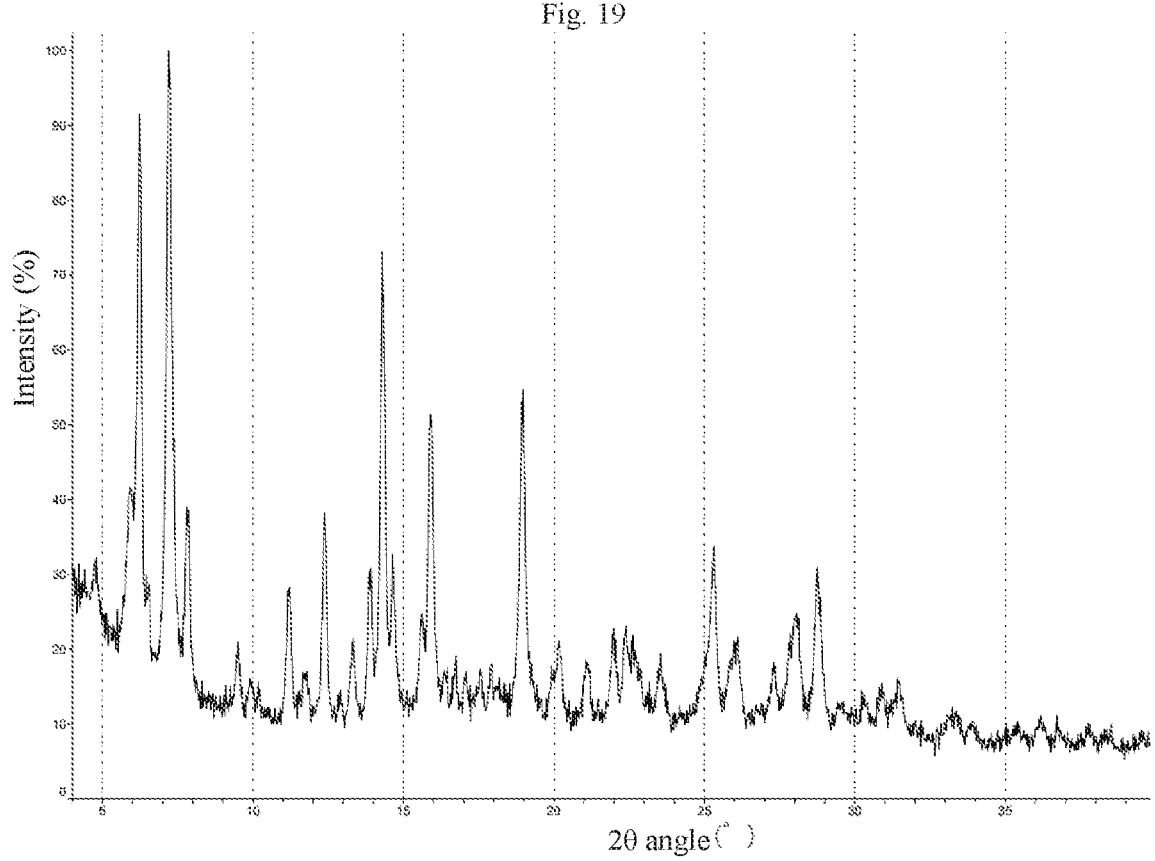
FIG. 19: A Cu-Kα radiated XRPD pattern of the crystal form G.
Figure 20:
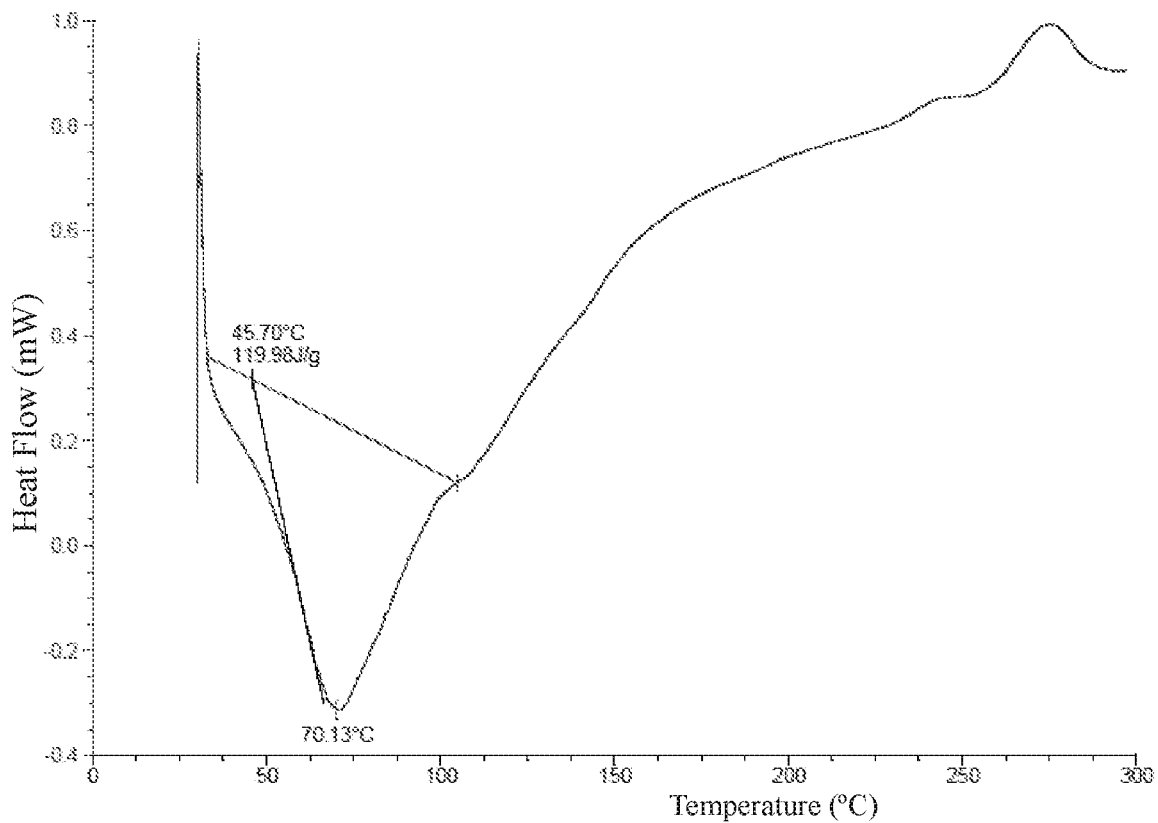
FIG. 20: A DSC pattern of the crystal form G.
Figure 21:
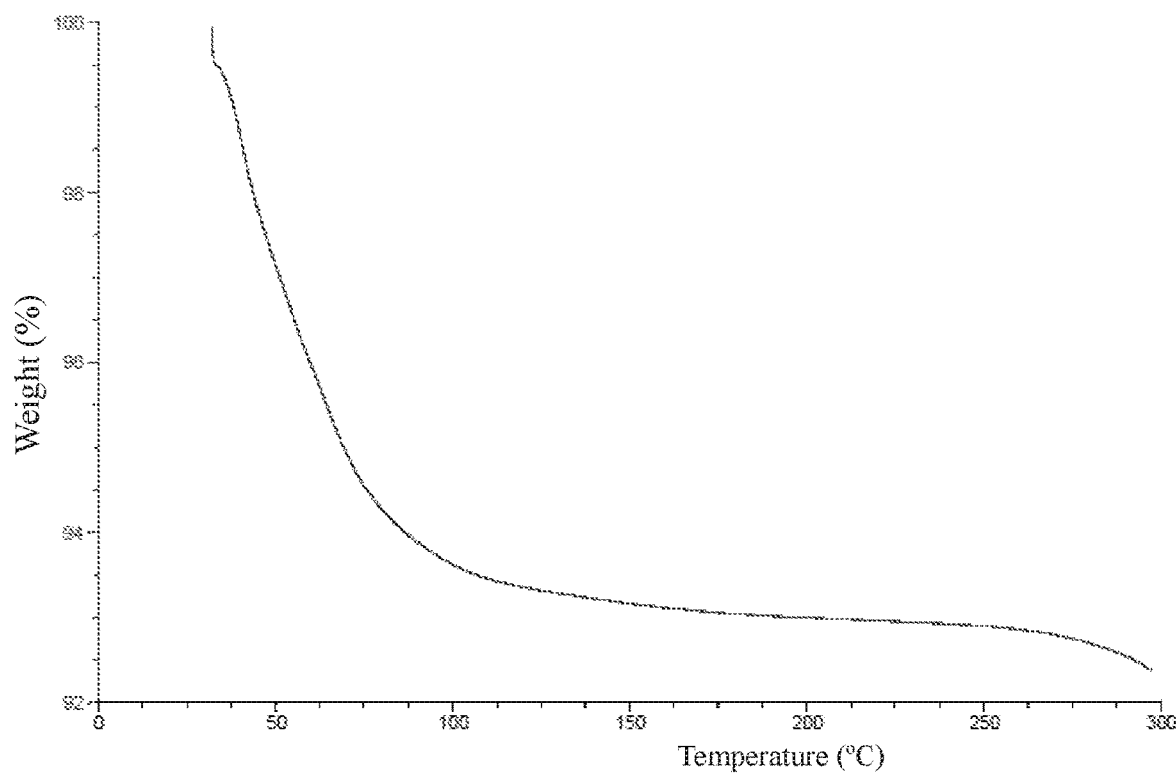
FIG. 21: A TGA pattern of the crystal form G.

Crystal form F (0.206 g) was dissolved into acetonitrile (3 mL) and beaten. The mixture was stirred at 30° C. for 12 hr, and the solid was filtered. The filter cake was dried under vacuum at 40° C. to give the crystal form G. The obtained crystal form G has an XRPD pattern as shown in FIG. 19, a DSC pattern as shown in FIG. 20, and a TGA pattern as shown in FIG. 21.

Example 11: Preparation of Crystal Form H

Figure 22:
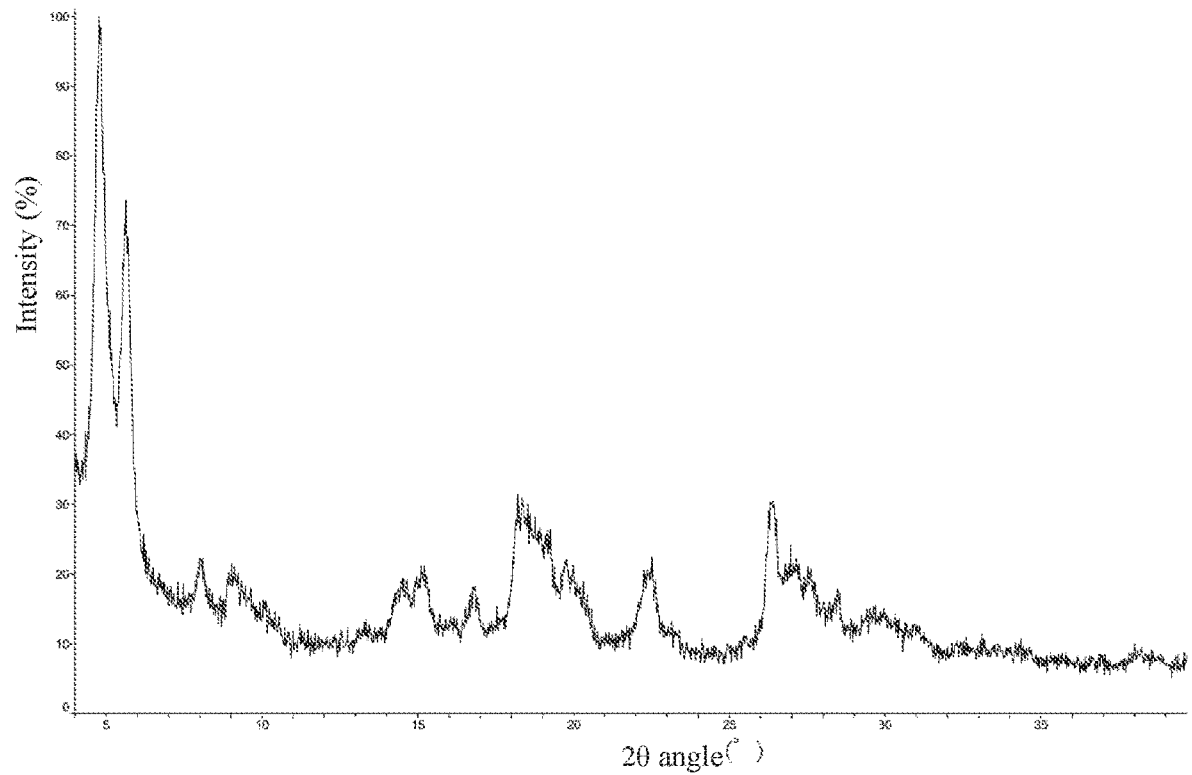
FIG. 22: A Cu-Kα radiated XRPD pattern of the crystal form H.
Figure 23:
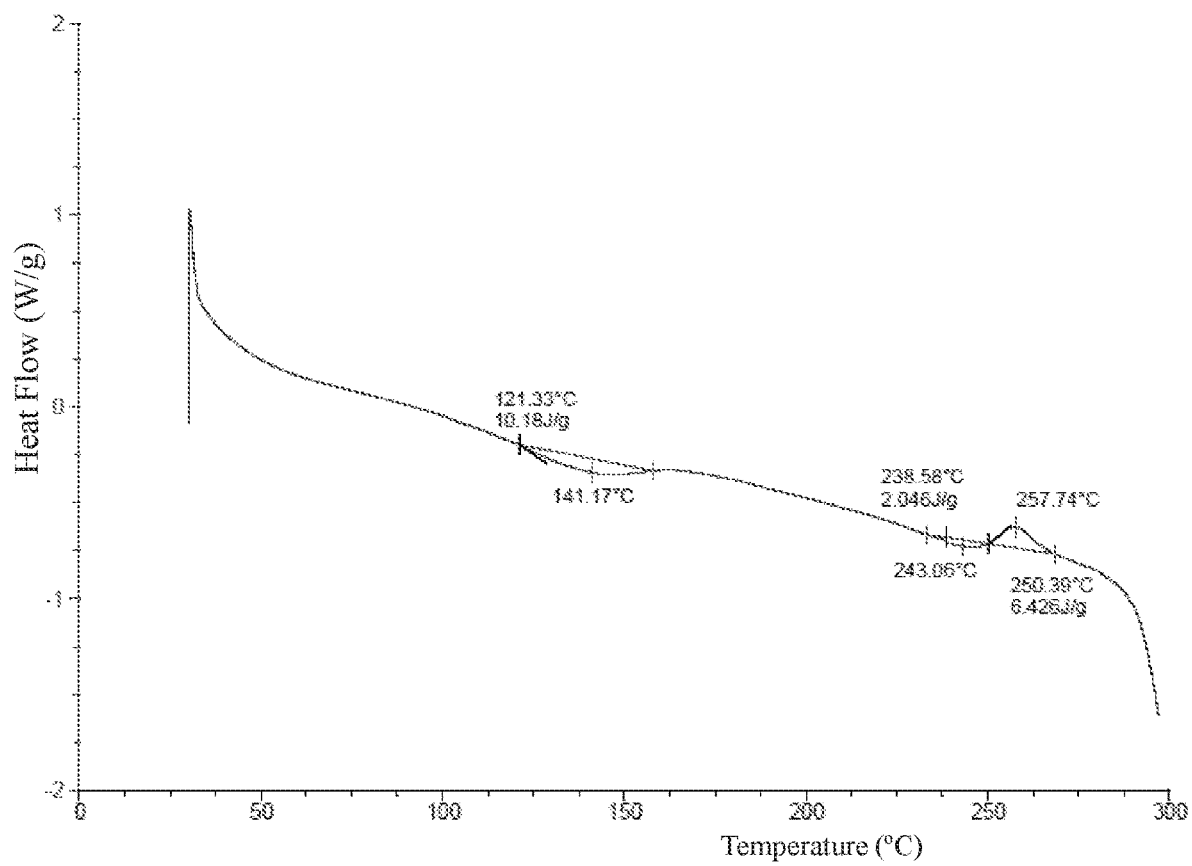
FIG. 23: A DSC pattern of the crystal form H.
Figure 24:
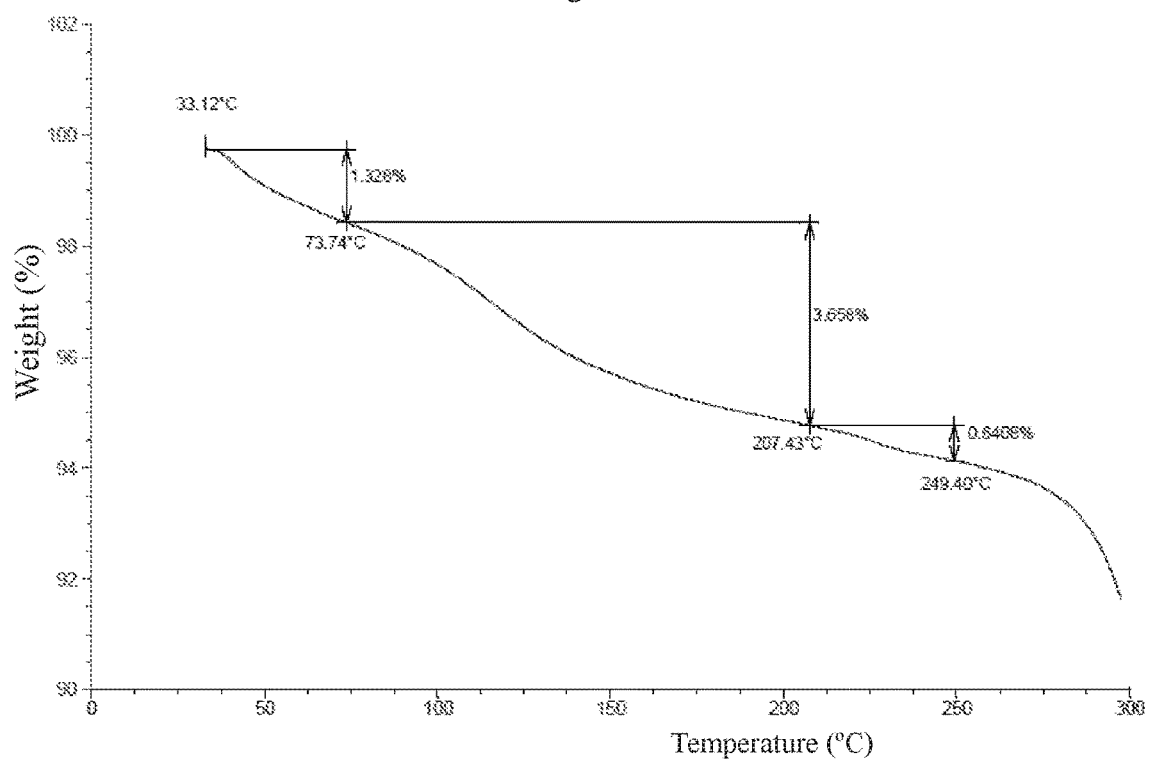
FIG. 24: A TGA pattern of the crystal form H.

About 2 g of Compound 1 was added into a 100 mL eggplant-shaped flask, THF (35 mL) was added, and an aqueous KOH solution (0.255 g, dissolved in 0.5 mL and 5 mL THF) was added. The mixture was stirred at 30° C. for 12 hr, and the solid was filtered. The filter cake was dried under vacuum at 40° C. to give the crystal form H. The obtained crystal form H has an XRPD pattern as shown in FIG. 22, a DSC pattern as shown in FIG. 23, and a TGA pattern as shown in FIG. 24.

Example 12: Preparation of Crystal Form I

Figure 25:
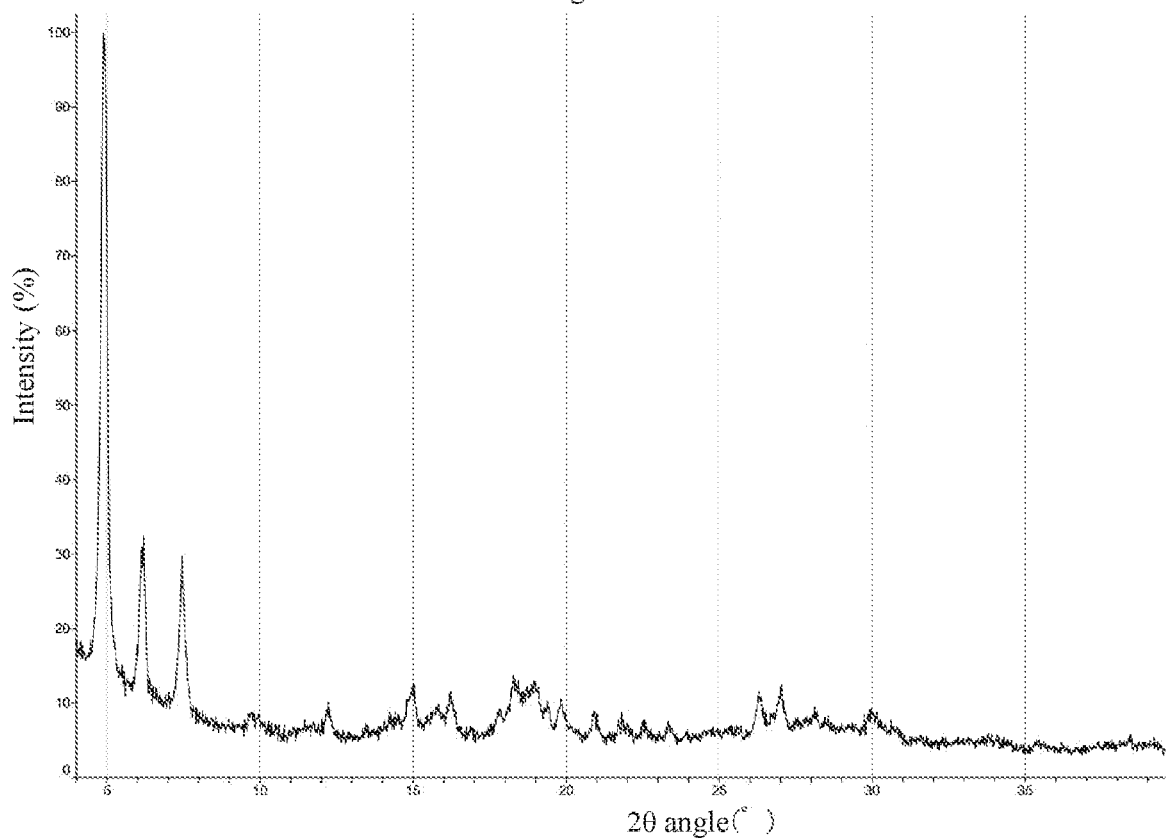
FIG. 25: A Cu-Kα radiated XRPD pattern of the crystal form I.
Figure 26:
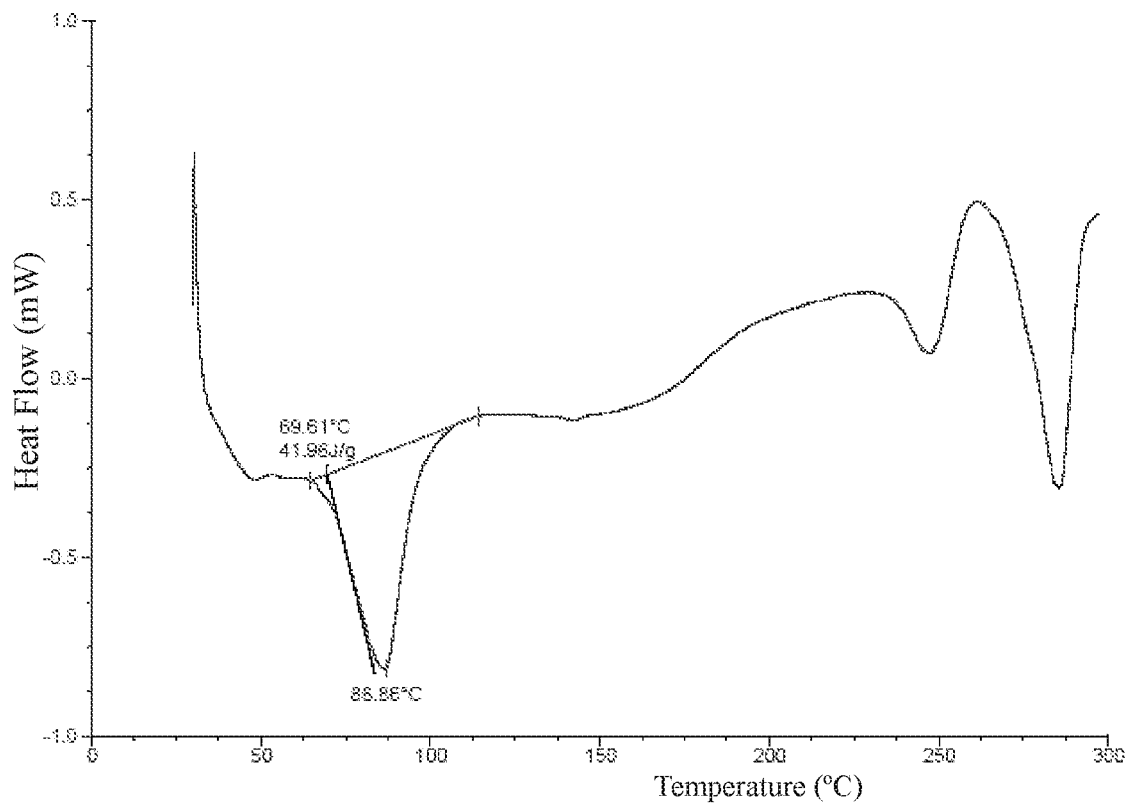
FIG. 26: A DSC pattern of the crystal form I.
Figure 27:
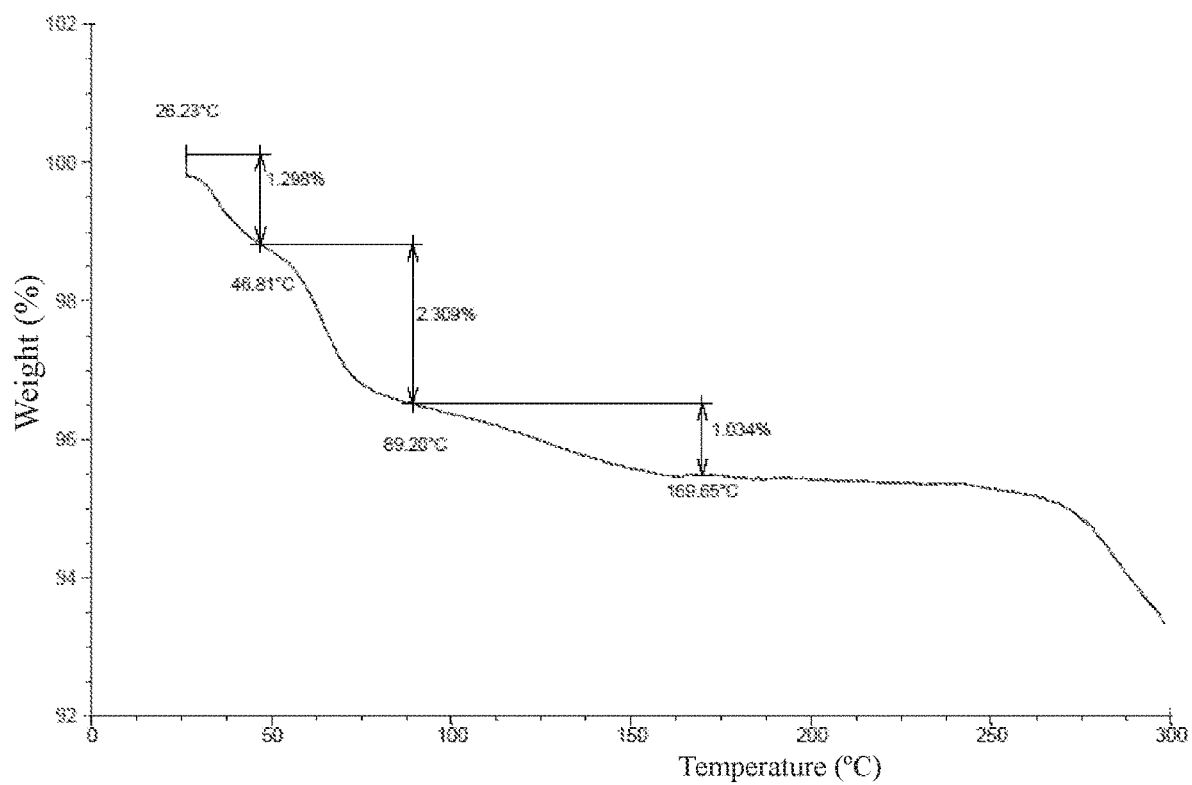
FIG. 27: A TGA pattern of the crystal form I.

Crystal form H (0.201 g) was dissolved into acetonitrile (3 mL) and beaten. The mixture was stirred at 25° C. for 12 hr, and the solid was filtered. The filter cake was dried under vacuum at 40° C. to give the crystal form I. The obtained crystal form I has an XRPD pattern as shown in FIG. 25, a DSC pattern as shown in FIG. 26, and a TGA pattern as shown in FIG. 27.

Example 13: Preparation of Crystal Form J

Figure 28:
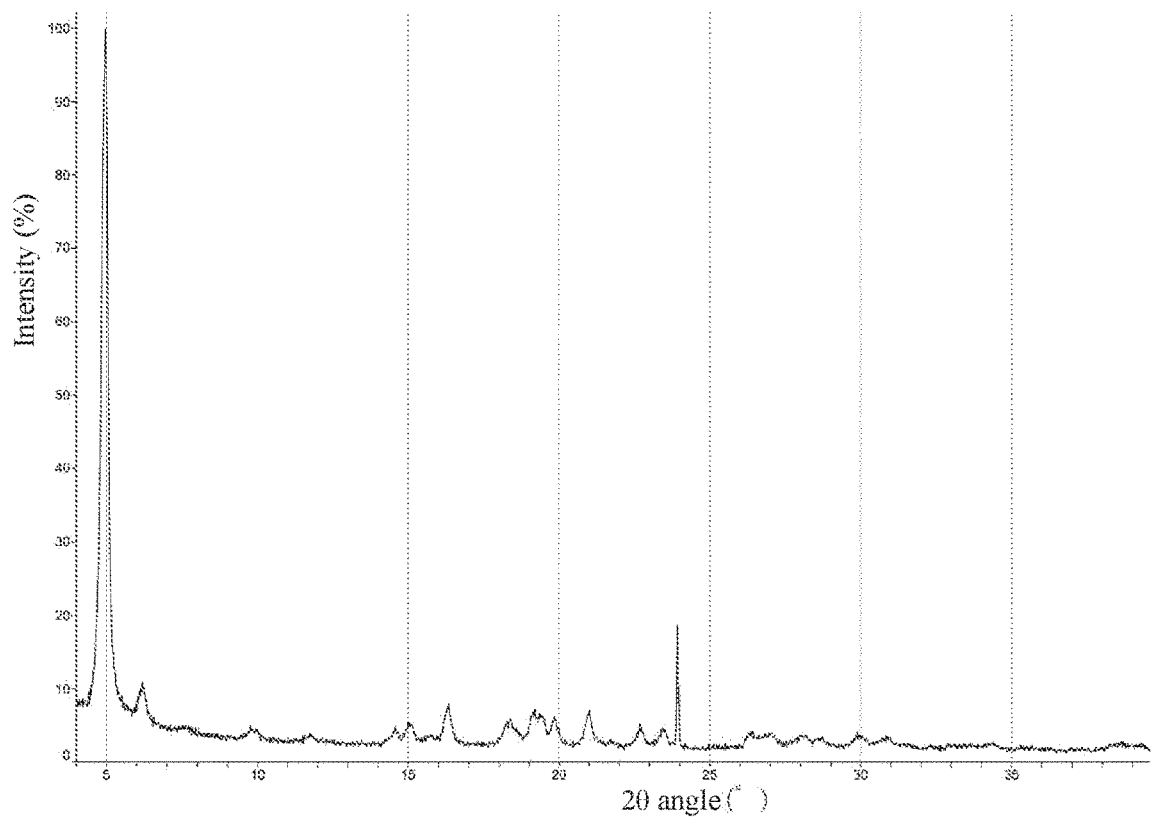
FIG. 28: A Cu-Kα radiated XRPD pattern of the crystal form J.
Figure 29:
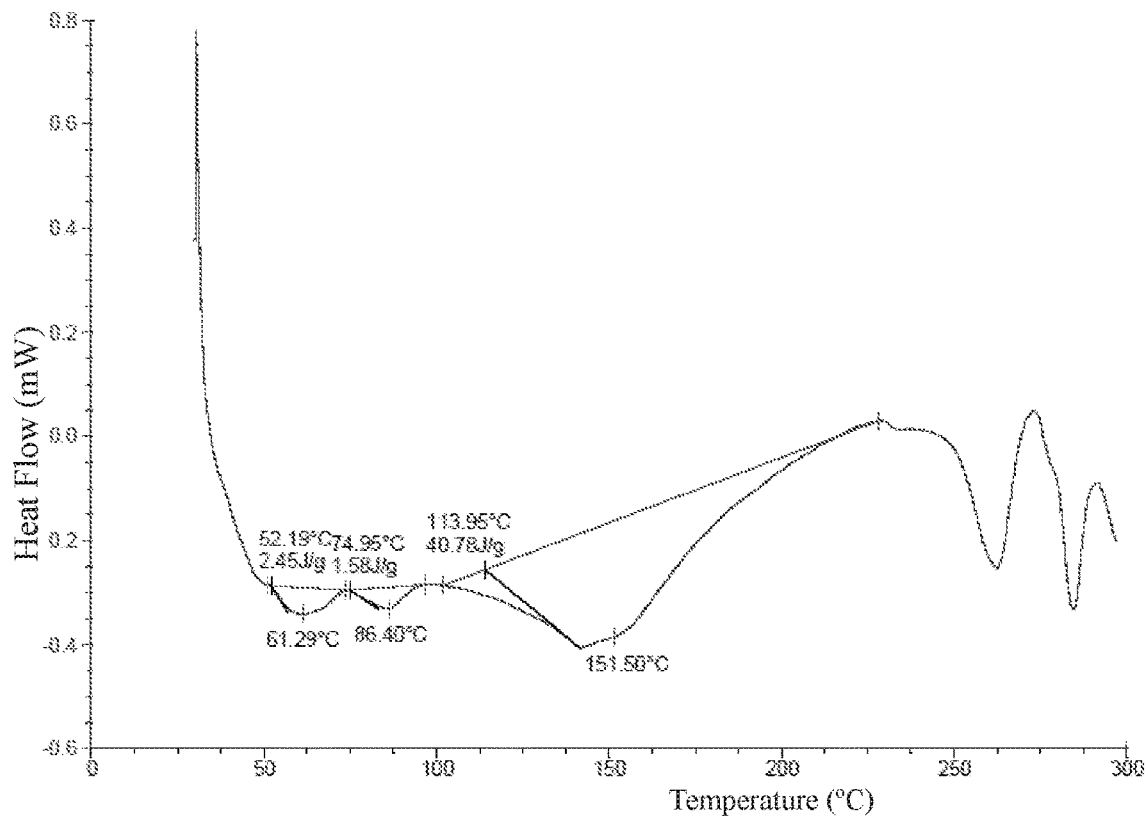
FIG. 29: A DSC pattern of the crystal form J.
Figure 30:
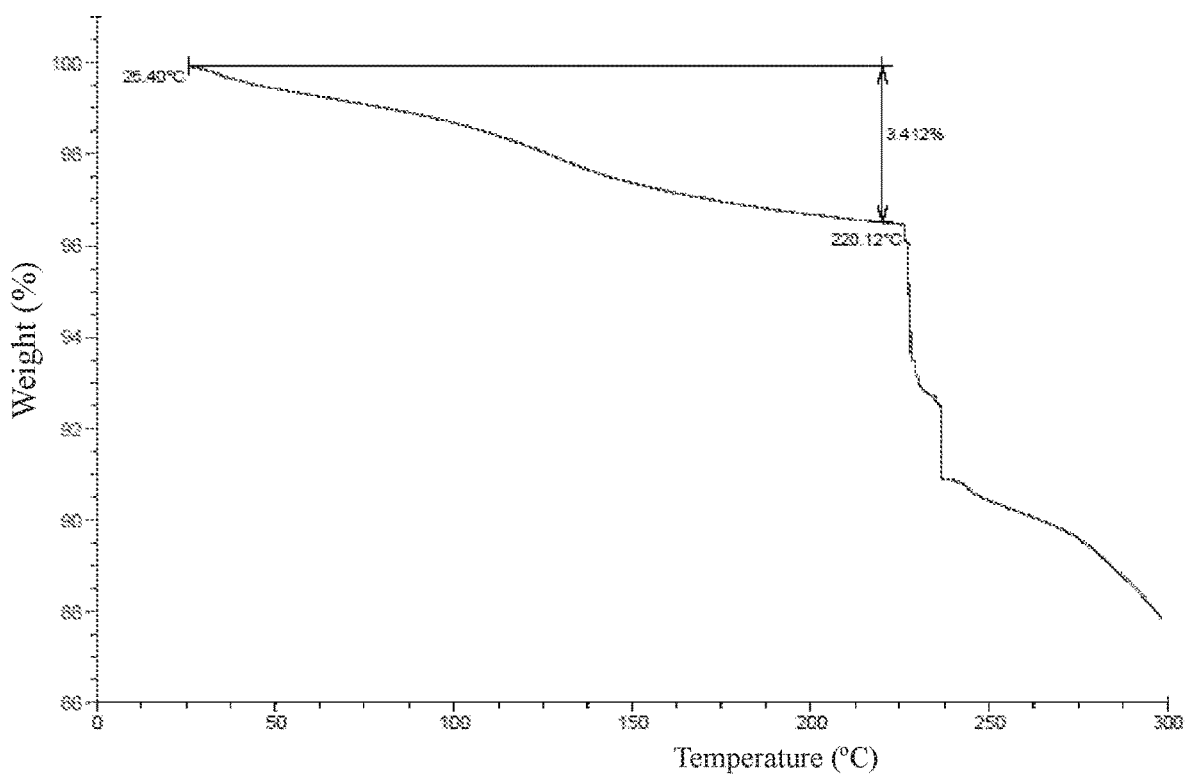
FIG. 30: A TGA pattern of the crystal form J.

Crystal form H (0.202 g) was dissolved into acetone (3 mL) and beaten. The mixture was stirred at 25° C. for 12 hr, and the solid was filtered. The filter cake was dried under vacuum at 40° C. to give the crystal form J. The obtained crystal form J has an XRPD pattern as shown in FIG. 28, a DSC pattern as shown in FIG. 29, and a TGA pattern as shown in FIG. 30.

Example 14: Preparation of Crystal Form K

Figure 31:
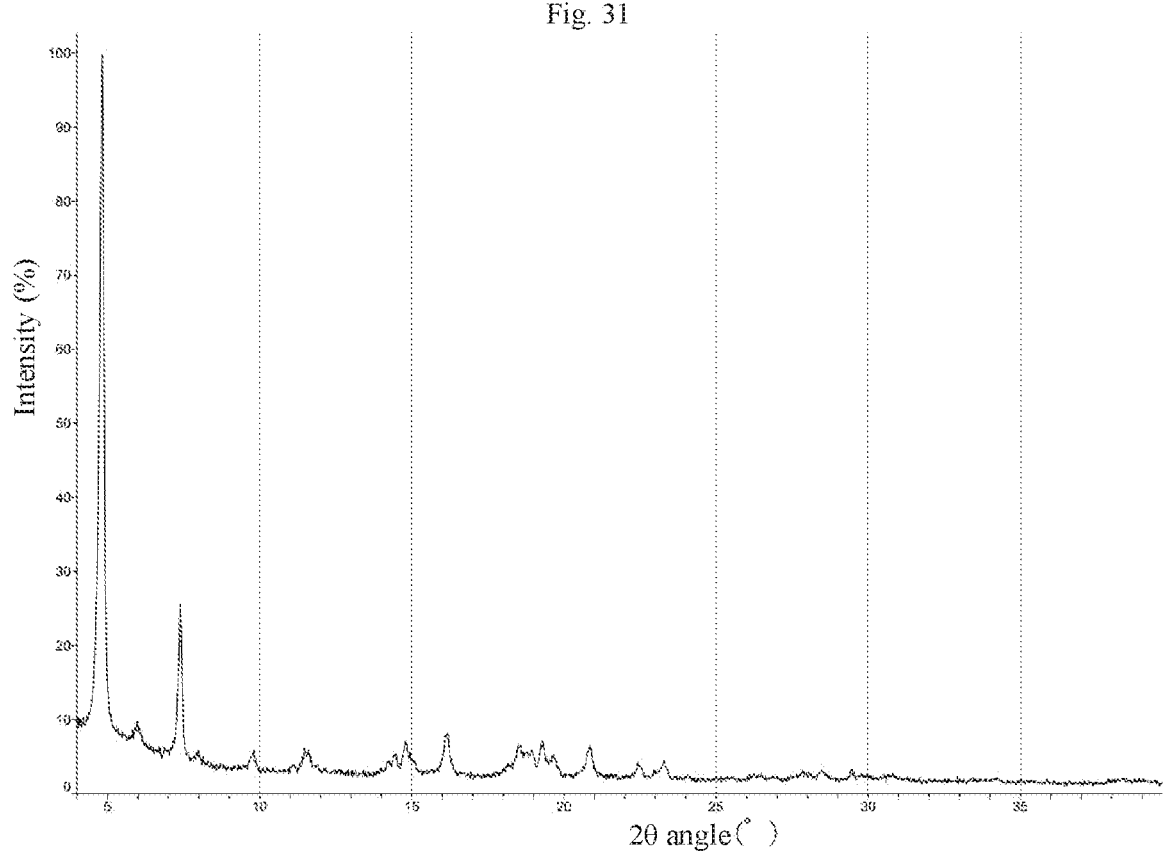
FIG. 31: A Cu-Kα radiated XRPD pattern of the crystal form K.
Figure 32:
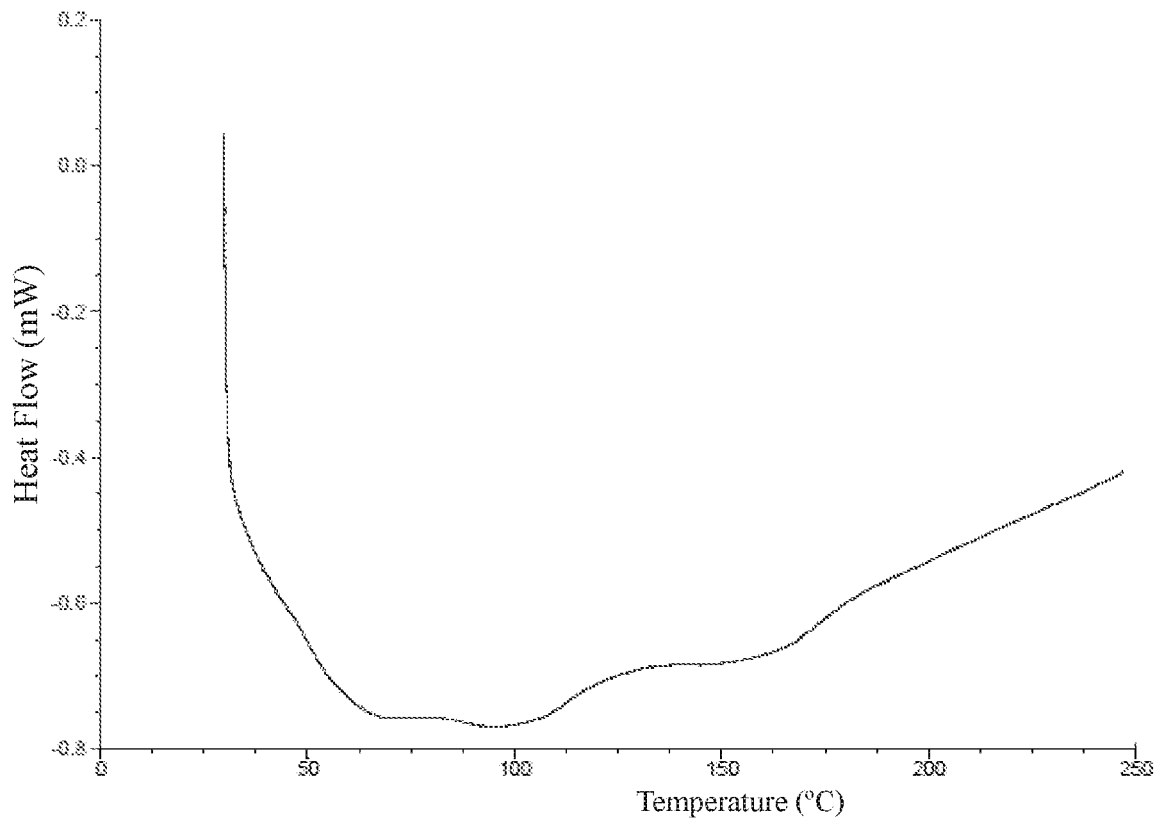
FIG. 32: A DSC pattern of the crystal form K.
Figure 33:
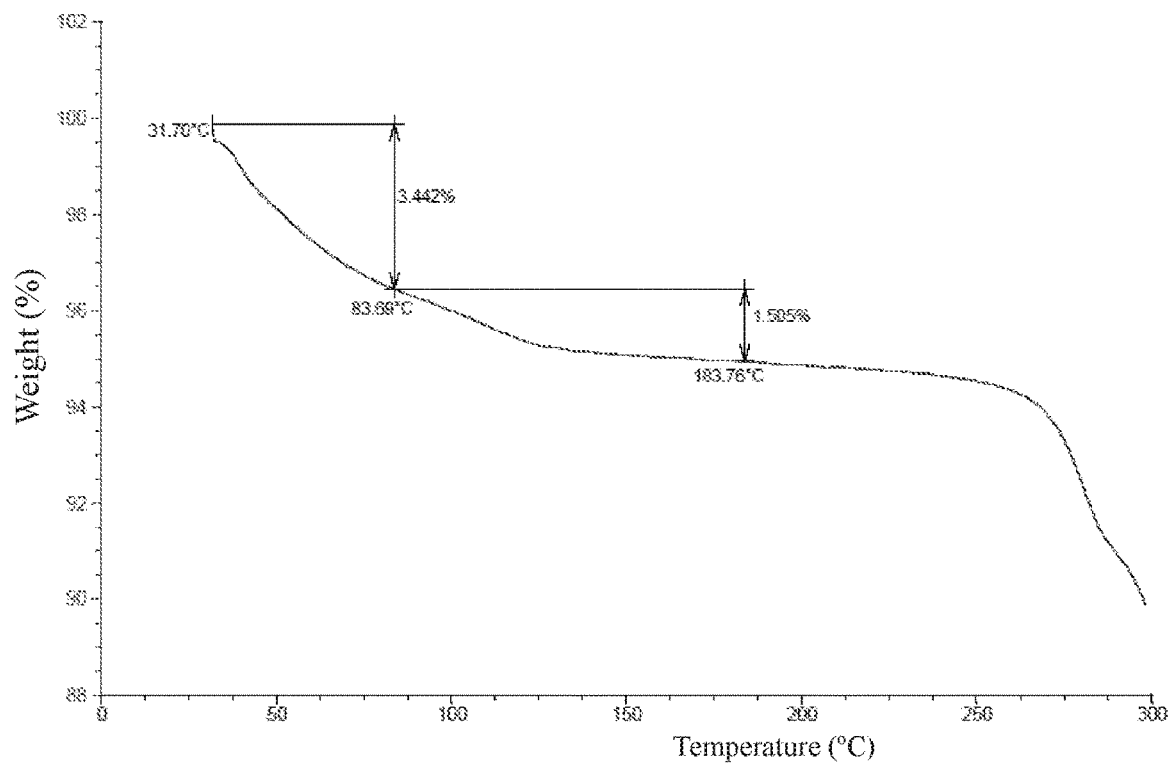
FIG. 33: A TGA pattern of the crystal form K.

Crystal form H (0.201 g) was dissolved into a mixed solvent of ethanol and water (ethanol: water=3:1) (4 mL) and beaten. The mixture was stirred at 25° C. for 12 hr, and the solid was filtered. The filter cake was dried under vacuum at 40° C. to give the crystal form K. The obtained crystal form K has an XRPD pattern as shown in FIG. 31, a DSC pattern as shown in FIG. 32, and a TGA pattern as shown in FIG. 33.

Figure 34:
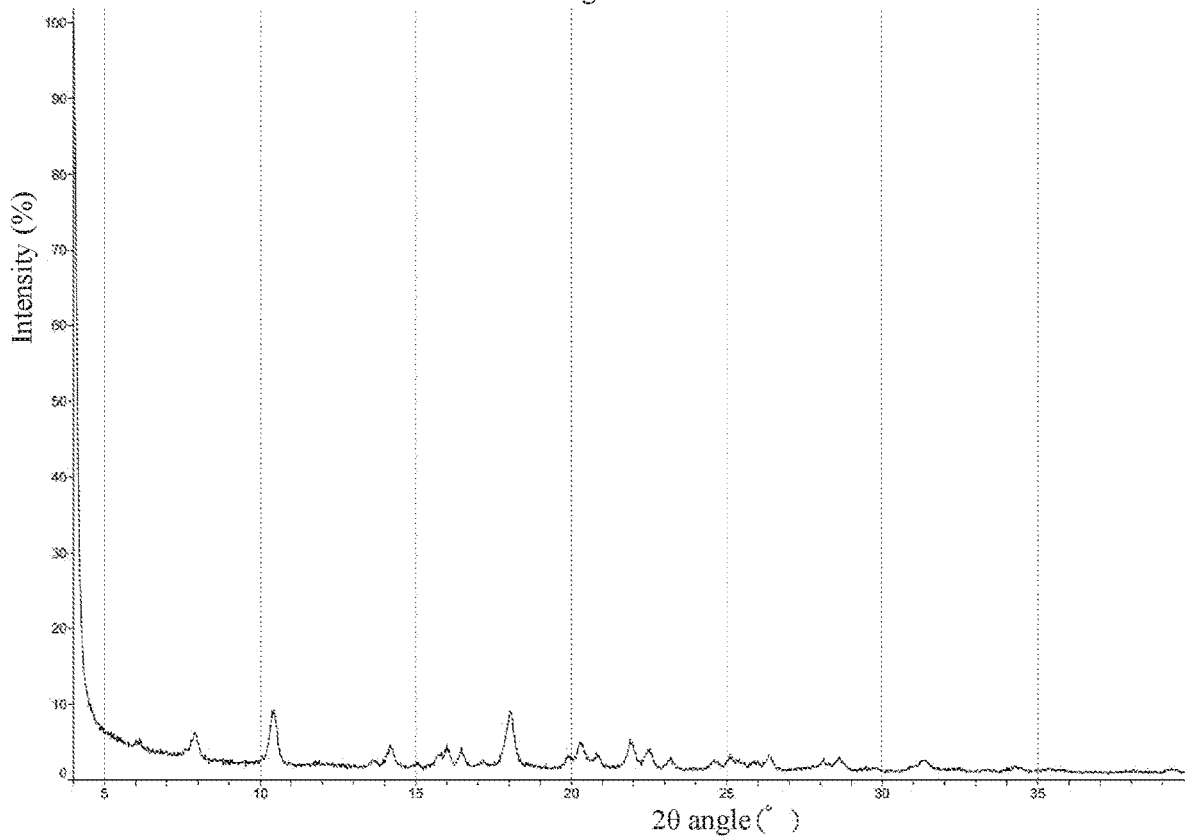
FIG. 34: A Cu-Kα radiated XRPD pattern of the crystal form L.
Figure 35:
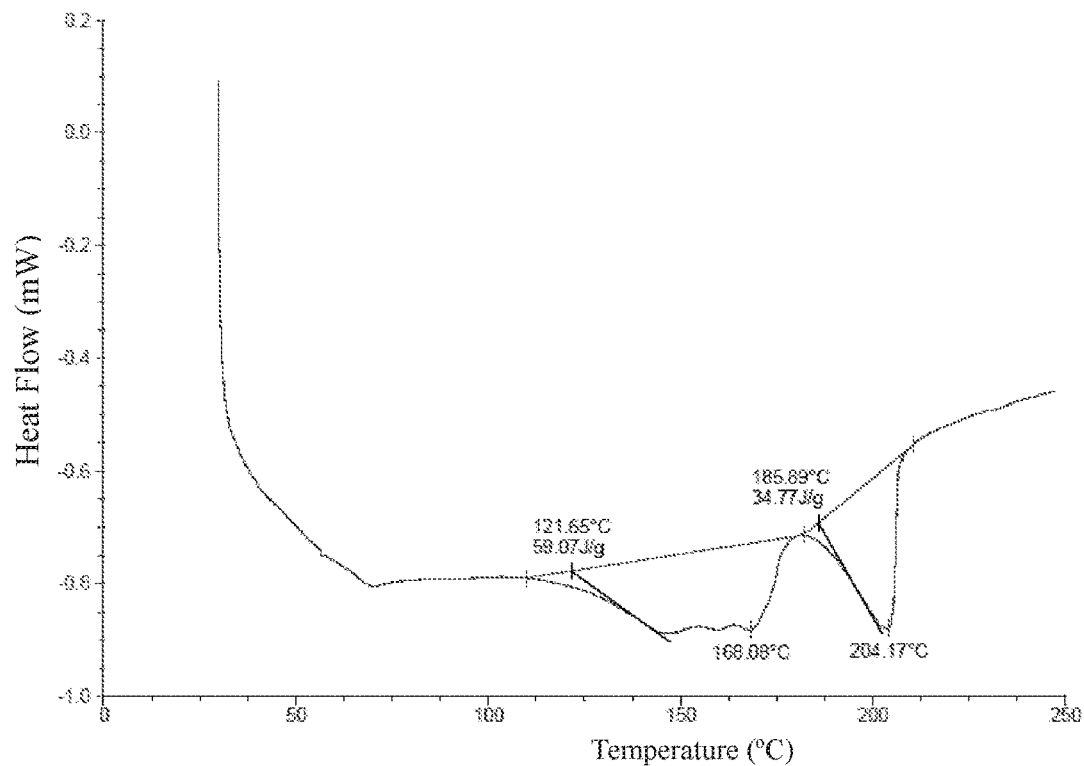
FIG. 35: A DSC pattern of the crystal form L
Figure 36:
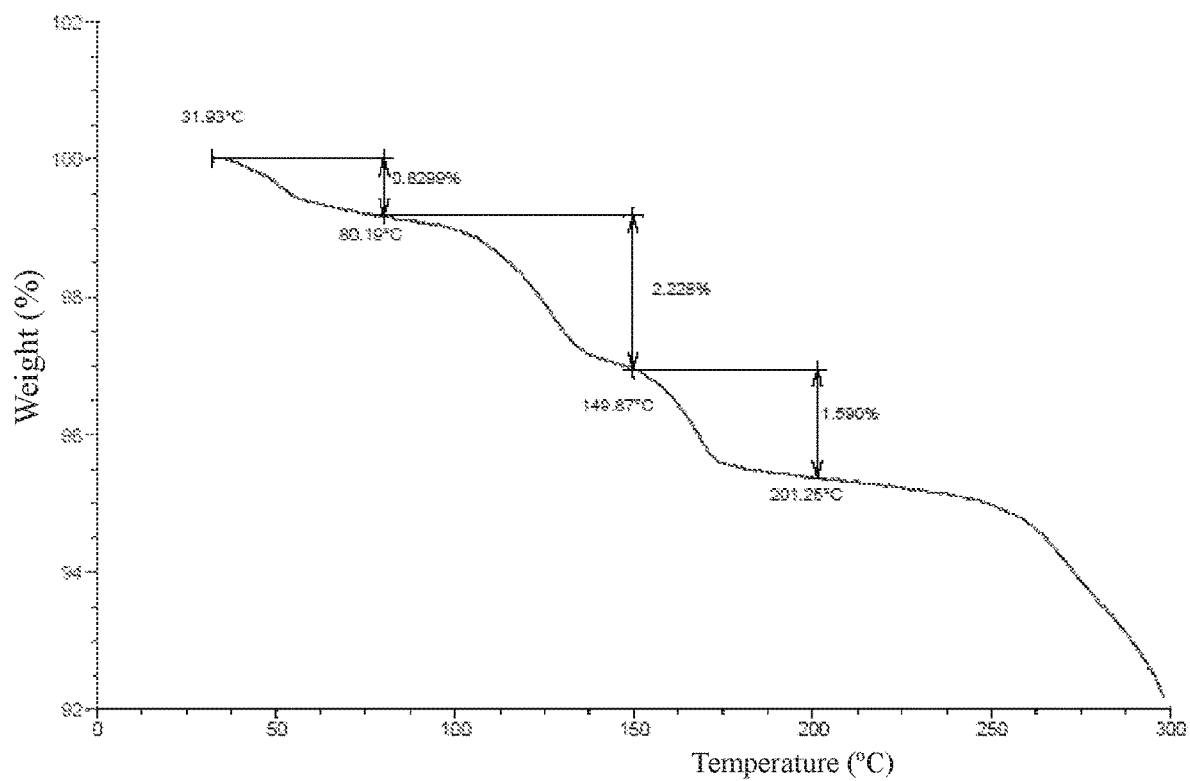
FIG. 36: A TGA pattern of the crystal form L.

Example 15: Preparation of Crystal Form L 2 g of Compound 1 was added into a 100 mL eggplant-shaped flask, THF (35 mL) was added, and an aqueous solution of calcium hydroxide (0.168 g, dissolved in 0.5 mL and 5 mL THF) was added. The mixture was stirred at 25° C. for 12 hr, and the solid was filtered. The filter cake was dried under vacuum at 40° C. to give a solid (1.440 g). The solid (0.204 g) was dissolved into a mixed solvent of ethanol and water (ethanol: water=3:1) (4 mL) and beaten. The mixture was stirred at 25° C. for 12 hr, and the solid was filtered. The filter cake was dried under vacuum at 40° C. to give the crystal form L. The obtained crystal form L has an XRPD pattern as shown in FIG. 34, a DSC pattern as shown in FIG. 35, and a TGA pattern as shown in FIG. 36.

Experimental Example 1: Solid Stability Test of Crystal Form A

A sample of crystal form A was placed at the bottom of a glass bottle to form a thin layer. The sample was placed under high temperature, high humidity and acceleration conditions. The bottle was sealed with an aluminum foil, and some small holes were pierced on the aluminum foil to ensure that the sample could fully contact with the ambient air. The sample placed under light radiation was placed upright at room temperature and open to the air. The sample was exposed to a light source, and radiated with sufficient energy prior to taking samples for detection. Samples were taken at various time points for analysis, and the detection results were compared with the initial detection results obtained at Day 0. The investigation items include appearance, content and impurities. The test results are shown in the following table:

| Test Conditions | Time Point | Appearance | Content (%) | Total Impurities (%) | XPRD |
|---|---|---|---|---|---|
| — | Day 0 | Off-white solid | 98.51 | 1.49 | Crystal form A |
| High temperature | Day 5 | Off-white solid | Not detected | Not detected | Not detected |
| (60° C., open) | Day 10 | Off-white solid | 98.25 | 1.75 | Crystal form A |
| High Humidity | Day 5 | Off-white solid | Not detected | Not detected | Not detected |
| (room temperature/relative humidity 92.5%, open) | Day 10 | Off-white solid | 98.25 | 1.75 | Crystal form A |
| Light Radiation | Day 5 | Off-white solid | Not detected | Not detected | Not detected |
| (total illumination: $1.2 \times 10^6$ Lux · hr/) | Day 10 | Off-white solid | 96.89 | 3.11 | Crystal form A |
| Acceleration Test | Day 5 | Off-white solid | Not detected | Not detected | Not detected |
| (40° C./relative humidity 75%, open) | Day 10 | Off-white solid | 98.36 | 1.64 | Crystal form A |

It can be seen from the above test results that the crystal form A prepared in the aforesaid examples shows that there is a relatively small change in total impurity content under the conditions of high temperature, high humidity and accelerated experiments. The XRPD detection method found that the crystal form A does not change and has a relatively high stability.

Experimental Example 2: Solid Stability Test of Crystal Form B

A sample of the crystal form B was placed at the bottom of a glass bottle to form a thin layer. The sample was placed under high temperature, high humidity and acceleration conditions. The bottle was sealed with an aluminum foil, and some small holes were pierced on the aluminum foil to ensure that the sample could fully contact with the ambient air. The sample placed under light radiation was placed upright at room temperature and open to the air. The sample was exposed to a light source, and radiated with sufficient energy prior to taking samples for detection. Samples were taken at various time points for analysis, and the detection results were compared with the initial detection results obtained at Day 0. The investigation items include appearance, content and impurities. The test results are shown in the following table:

| Test Conditions | Time points | Appearance | Content (%) | Total Impurities (%) | XPRD |
|---|---|---|---|---|---|
| — | Day 0 | Off-white solid | 98.89 | 1.11 | Crystal form B |
| High temperature (60° C., open) | Day 5 | Off-white solid | 98.91 | 1.09 | Not detected |
| | Day 10 | Off-white solid | 98.89 | 1.11 | Crystal form B |
| High Humidity (room temperature/relative humidity 92.5%, open) | Day 5 | Off-white solid | 98.92 | 1.08 | Not detected |
| | Day 10 | Off-white solid | 98.90 | 1.10 | Crystal form B |
| Light Radiation (total illumination: 1.2 × $10^6$ Lux · hr/) | Day 5 | Off-white solid | Not detected | Not detected | Not detected |
| | Day 10 | Off-white solid | 98.03 | 1.97 | Crystal form B |

It can be seen from the above test results that the crystal form B prepared in the aforesaid examples shows that there is almost no change in total impurity content under the conditions of high temperature, high humidity, and a relatively small change in total impurity in the accelerated experiments. The XRPD detection method found that the crystal form B does not change, and has a relatively high stability.

Experimental Example 3

The stability of the crystal form D was tested by the same method as that of Experimental Example 1. Samples were taken at various time points, and the test results were compared with the initial test results obtained at Day 0. The investigation items include appearance, impurities, and crystal forms. The test results are shown in the following table:

| Test Conditions | Time Points | Appearance | Total Impurities (%) | XPRD |
|---|---|---|---|---|
| — | Day 0 | Off-white solid | 3.3 | Crystal form D |
| High temperature (60° C., open) | Day 5 | Off-white solid | Not detected | Not detected |
| | Day 12 | Off-white solid | 3.3 | Crystal form D |
| High Humidity (room temperature/relative humidity 92.5%, open) | Day 5 | Off-white solid | Not detected | Not detected |
| | Day 12 | Off-white solid | 3.4 | Crystal form D |
| Light Radiation (total illumination: 1.2 × $10^6$ Lux · hr/) | Day 5 | Off-white solid | Not detected | Not detected |
| | Day 12 | Off-white solid | 3.4 | Crystal form D |
| Acceleration Test (40° C./relative humidity 75%, open) | Day 5 | Off-white solid | Not detected | Not detected |
| | Day 12 | Off-white solid | 3.5 | Crystal form D |

It can be seen from the above test results that the crystal form D prepared in the aforesaid examples shows that there is almost no change in total impurity content under the conditions of high temperature, high humidity, light radiation and accelerated experiments. The XRPD detection method found that the crystal form D does not change, and has a relatively high stability.

Experimental Example 4

The stability of the crystal form F was tested by the same method as that of Experimental Example 1. Samples were taken at various time points, and the test results were compared with the initial test results obtained at Day 0. The investigation items include appearance, impurities, and crystal forms. The test results are shown in the following table:

| Test Conditions | Time Points | Appearance | Total Impurities (%) | XPRD |
| --- | --- | --- | --- | --- |
| — | Day 0 | Off-white solid | 1.7 | Crystal form F |
| High temperature | Day 5 | Off-white solid | Not detected | Not detected |
| (60° C., open) | Day 12 | Off-white solid | 1.9 | Crystal form F |
| High Humidity | Day 5 | Off-white solid | Not detected | Not detected |
| (room temperature/relative humidity 92.5%, open) | Day 12 | Off-white solid | 1.9 | Crystal form F |
| Light Radiation | Day 5 | Off-white solid | Not detected | Not detected |
| (total illumination: $1.2 \times 10^6$ Lux · hr/) | Day 12 | Off-white solid | 1.8 | Crystal form F |
| Acceleration Test | Day 5 | Off-white solid | Not detected | Not detected |
| (40° C./relative humidity 75%, open) | Day 12 | Off-white solid | 1.9 | Crystal form F |

It can be seen from the above test results that the crystal form F prepared in the aforesaid examples shows that there is almost no change in total impurity content under the conditions of high temperature, high humidity and accelerated experiments. The XRPD detection method found that the crystal form F does not change, and has a relatively high stability.

Experimental Example 5

The stability of the crystal form G was tested by the same method as that of Experimental Example 1. Samples were taken at various time points, and the test results were compared with the initial test results obtained at Day 0. The investigation items include appearance, impurities, and crystal forms. The test results are shown in the following table:

| Test Conditions | Time Points | Appearance | Total Impurities (%) | XPRD |
| --- | --- | --- | --- | --- |
| — | Day 0 | Off-white solid | 0.35 | Crystal form G |
| High temperature | Day 5 | Off-white solid | Not detected | Not detected |
| (60° C., open) | Day 30 | Off-white solid | 0.42 | Crystal form G |
| High Humidity | Day 5 | Off-white solid | Not detected | Not detected |
| (room temperature/relative humidity 92.5%, open) | Day 30 | Off-white solid | 0.33 | Crystal form G |
| Light Radiation | Day 5 | Off-white solid | Not detected | Not detected |
| (total illumination: $1.2 \times 10^6$ Lux · hr/) | Day 12 | Yellowish solid | 0.54 | Crystal form G |
| Acceleration Test | Day 5 | Off-white solid | Not detected | Not detected |
| (40° C./relative humidity 75%, open) | Day 30 | Off-white solid | 0.35 | Crystal form G |

It can be seen from the above test results that the crystal form G prepared in the aforesaid examples shows that there is almost no change in total impurity content under the conditions of high humidity and accelerated experiments, and there is a relatively small change in total impurity content under the conditions of high temperature. The XRPD detection method found that the crystal form G does not change, and thus it can be known that the crystal form has a relatively high stability.

Experimental Example 6

The stability of the crystal form H was tested by the same method as that of Experimental Example 1. Samples were taken at various time points, and the test results were compared with the initial test results obtained at Day 0. The investigation items include appearance, impurities, and crystal forms. The test results are shown in the following table:

| Test Conditions | Time Point | Appearance | Total Impurities (%) | XPRD |
| --- | --- | --- | --- | --- |
| — | Day 0 | Off-white solid | 1.8 | Crystal form H |
| High temperature | Day 5 | Off-white solid | Not detected | Not detected |
| (60° C., open) | Day 30 | Off-white solid | 2.0 | Crystal form H |
| High Humidity | Day 5 | Off-white solid | Not detected | Not detected |
| (room temperature/relative humidity 92.5%, open) | Day 30 | Off-white solid | 1.9 | Crystal form H |
| Light Radiation | Day 5 | Off-white solid | Not detected | Not detected |
| (total illumination: 1.2 × $10^6$ Lux · hr/) | Day 12 | Yellowish solid | 1.9 | Crystal form H |
| Acceleration Test | Day 5 | Off-white solid | Not detected | Not detected |
| (40° C./relative humidity 75%, open) | Day 30 | Off-white solid | 2.0 | Crystal form H |

It can be seen from the above test results that the crystal form H prepared in the aforesaid examples shows that there is almost no change in total impurity content under the conditions of high temperature, high humidity, light radiation and accelerated experiments. The XRPD detection method found that the crystal form H does not change, and it can be seen that the crystal form has a relatively high stability.

Those skilled in the art can understand that the crystal forms in the examples are obtained by long-term stirring and beating/crystallizing, and tend to form a stable state, thereby having a relatively high stability. They have considerable pharmaceutical prospects, and can also be used as an intermediate in the preparation of pharmaceutical products in production.

Biological Part

Influenza Virus Cytopathy (CPE) Experiment

The antiviral activity of a compound against influenza virus (IFV) is evaluated by measuring the half effective concentration ($EC_{50}$) value of a compound. The cytopathic test is widely used to determine the protective effect of the compound on virus-infected cells to reflect the antiviral activity of the compound.

Influenza Virus CPE Experiment

MDCK cells (ATCC, Catalog No. CCL-34) were seeded into a black 384-well cell culture plate at a density of 2,000-3,000 cells/well, and then placed in a 37° C., 5% $CO_2$ incubator overnight. The compounds were diluted by use of Echo555 Non-Contact nanoliter-grade sonic pipetting system, and added into the wells (3-fold dilution, 8 test concentration points). Influenza virus A/Weiss/43 (H1N1) strain (ATCC, Catalog No. VR-96) was then added at 1-2 90% tissue culture infectious dose per well (TCID90) into the wells to allow that the final concentration of DMSO in the medium was 0.5%. Virus control wells (DMSO and virus added, but no compound added) and cell control wells (DMSO added, and no compound and virus added) were set. The plate was placed in a 37° C., 5% $CO_2$ incubator for 5 days. After culturing for 5 days, a cell viability detection kit CCK8 was used to detect the cell viability. The raw data was used to calculate the antiviral activity of the compound.

The antiviral activity of the compound is represented by the inhibition rate (%) of the compound on the cytoviral effect caused by the virus. The calculation formula is as follows:

$$\% \text{ Inhibition Rate} = \left( \frac{\text{Sample value} - \text{Average value of virus controls}}{\text{Average value of cell controls} - \text{Average value of virus controls}} \right) \times 100$$

GraphPad Prism software was used to perform a nonlinear fitting analysis on the inhibition rate of the compound to give the $EC_{50}$ value of the compound. The experimental results are shown in Table 15.

TABLE 15

| In vitro screening test results | |
| --- | --- |
| Compound | $EC_{50}$ (nM) |
| Compound 1 | 0.013 |

Results and Discussion: Compound 1 shows a positive effect in the experiment of inhibiting influenza virus replication at a cell level.

Experimental Example 2: In Vivo Drug Efficacy Studies

Evaluation of the efficacy of compounds in influenza A virus H1N1 mouse infection model Mice were infected with Influenza A virus H1N1 (Virapur Company, Catalog No.: F1003A) by intranasal drip, and were treated with the compound at 36 hr after infection. The mice were orally administered for 7 consecutive days, twice a day. By observing the changes in body weight and survival rate of mice, the anti-influenza A virus H1N1 effect of the compound in this model was evaluated.

The experiment used SPF-grade BALB/c mice (Shanghai Lingchang Biological Technology Co., Ltd.), 6-7 weeks of age, female. The mice adapted to the BSL-2 animal room for at least 3 days and then the experiment started. The infection day was set as Day 0. The mice were anesthetized by intraperitoneal injection of pentobarbital sodium (75 mg/kg, 10 ml/kg). The animal was infected with the H1N1 A/WSN/33 virus by intranasal drip after it entered the state of deep anesthesia, and the infection volume was 50 µl. From Day 1 to Day 7, 10 mg/kg (administration volume of 10 ml/kg) of the test compound was administered orally twice a day. The time of the first administration was 36 hr after infection. The state of the mice was observed daily, and the weight and survival rate of mice were recorded. At Day 14, all the surviving animals were euthanized.

The measured survival rate and weight loss rate of the animals are shown in Table 16.

TABLE 16

Measured survival rate and rate of weight loss of animals

| Compound | Rate of Weight Loss (Day 9) | Survival Rate (%) |
|---|---|---|
| Compound 1 | 4.8% | 100% |

What is claimed is:

1. A crystal form A or B of a compound of Formula (I),

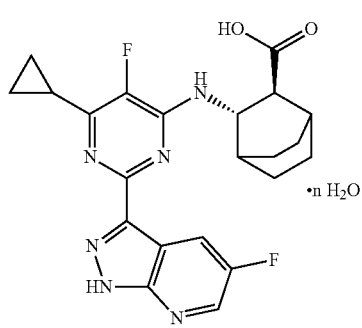

(I)

·n H$_2$O wherein n is selected from 0, 0.5, 1, 1.5, 2, 2.5, 3, 3.5 and 4, wherein the crystal form A has an X-ray powder diffraction pattern (XRPD) with characteristic diffraction peaks at 2θ angles of 6.61±0.2°, 9.27±0.2°, 14.66±0.2°, wherein the crystal form B has an X-ray powder diffraction pattern (XRPD) with characteristic diffraction peaks at 2θ angles of 7.14±0.2°, 11.19±0.2°, 22.39±0.2°.

2. The crystal form A or B of the compound of Formula (I) according to claim 1, wherein the crystal form A of the compound of Formula (I) has an XRPD pattern with characteristic diffraction peaks at 2θ angles of 6.61±0.2°, 9.27±0.2°, 14.66±0.2°, 16.69±0.2°, 18.65±0.2°, 19.79±0.2°, 21.85±0.2°, 24.63±0.2°, and further has an XRPD pattern analysis data as shown in the following table:

| No. | 2θ (±0.2°) |
|---|---|
| 1 | 4.693 |
| 2 | 6.606 |
| 3 | 7.371 |
| 4 | 9.272 |
| 5 | 10.396 |
| 6 | 14.66 |
| 7 | 16.219 |
| 8 | 16.693 |
| 9 | 17.502 |
| 10 | 18.648 |
| 11 | 19.099 |
| 12 | 19.793 |
| 13 | 20.683 |
| 14 | 21.846 |
| 15 | 22.814 |
| 16 | 23.188 |
| 17 | 23.642 |
| 18 | 24.631 |
| 19 | 24.964 |
| 20 | 25.516 |
| 21 | 26.385 |
| 22 | 27.138 |
| 23 | 27.946 |
| 24 | 29.426 |
| 25 | 30.236 |
| 26 | 31.204 |
| 27 | 31.675 |
| 28 | 33.02 |
| 29 | 33.65 |
| 30 | 35.623 |
| 31 | 36.259 |
| 32 | 38.665 | further, the crystal form A of the compound of Formula (I) has an XRPD pattern as shown in FIG. 1;

further, the crystal form A of the compound of Formula (I) has a differential scanning calorimetry (DSC) curve with a starting point of an endothermic peak at 185.46° C.±3° C., and further has a DSC pattern as shown in FIG. 2;

further, the crystal form A of the compound of Formula (I) has a thermogravimetric analysis (TGA) curve with a weight loss of 2.479% at 120.00° C.±3° C., and further has a TGA pattern as shown in FIG. 3;

further, for the crystal form A of the compound of Formula (I), the compound of Formula (I) has a structure as represented by Compound 1:

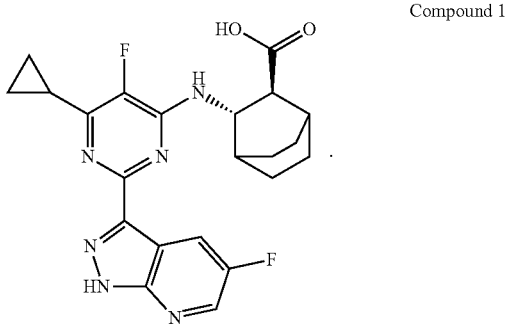 [SMILES: O=C(O)[C@H]1C2CCC(CC2)[C@@H]1Nc1nc(-c2n[nH]c3ncc(F)cc23)nc(C2CC2)c1F]

Compound 1

3. The crystal form A or B of the compound of Formula (I) according to claim 1, wherein the crystal form B has an XRPD pattern with characteristic diffraction peaks at 2θ angles of 7.14±0.2°, 11.19±0.2°, 12.00±0.2°, 17.28±0.2°, 18.84±0.2°, 22.39±0.2°, 26.90±0.2°, 27.95±0.2°, and further has an XRPD pattern analysis data as shown in the following table:

| No. | 2θ (±0.2°) |
|---|---|
| 1 | 7.143 |
| 2 | 8.662 |
| 3 | 11.192 |
| 4 | 12.003 |
| 5 | 14.076 |
| 6 | 14.512 |
| 7 | 15.222 |
| 8 | 15.912 |
| 9 | 16.546 |
| 10 | 17.276 |
| 11 | 18.088 |
| 12 | 18.837 |
| 13 | 19.55 |
| 14 | 19.964 |
| 15 | 20.536 |
| 16 | 21.166 |
| 17 | 22.393 |
| 18 | 22.808 |
| 19 | 23.658 |
| 20 | 24.032 |
| 21 | 25.037 |
| 22 | 25.497 |
| 23 | 25.871 |
| 24 | 26.562 |
| 25 | 26.898 |
| 26 | 27.946 |
| 27 | 29.566 |
| 28 | 30.181 |
| 29 | 30.889 |
| 30 | 31.759 |
| 31 | 32.294 |
| 32 | 32.687 |
| 33 | 33.4 |
| 34 | 34.246 |
| 35 | 34.721 |
| 36 | 36.225 |
| 37 | 38 | further, the crystal form B of the compound of Formula (I) has an XRPD pattern as shown in FIG. 4;
further, the crystal form B of the compound of Formula (I) has a differential scanning calorimetry (DSC) curve with an endothermic peak at 101.04° C.±3° C., and a starting point of an endothermic peak at 188.30° C.±3° C., and further has a DSC pattern as shown in FIG. 5;
further, the crystal form B of the compound of Formula (I) has a thermogravimetric analysis (TGA) curve with a weight loss of 4.087% at 154.18° C.±3° C. and a weight loss of up to 4.610% at 196.80° C.±3° C., and further has a TGA pattern as shown in FIG. 6;
further, for the crystal form B of the compound of Formula (I), the compound of Formula (I) has a structure as represented by Compound 2:

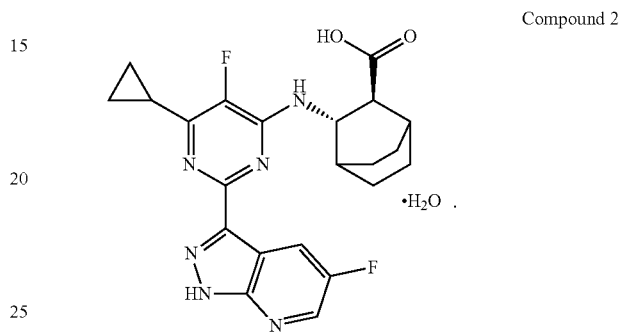

Compound 2

·H₂O .

4. A compound of Formula (II) as represented by the following formula, or a crystal form C or D thereof:

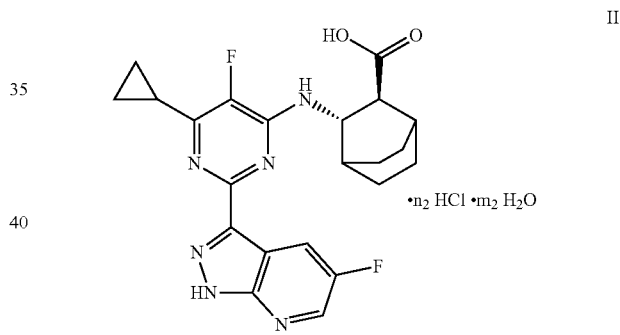

II

·n₂ HCl ·m₂ H₂O wherein, $n_2$ is selected from 1;

$m_2$ is selected from 0, 0.5, 1, 1.5, 2, 2.5, 3, 3.5 and 4;

the crystal form C of the compound of Formula (II) has an X-ray powder diffraction (XRPD) pattern with characteristic diffraction peaks at 2θ angles of 8.00±0.2°, 15.06±0.2°, 15.84±0.2°;

the crystal form D of the compound of Formula (II) has an X-ray powder diffraction (XRPD) pattern with characteristic diffraction peaks at 2θ angles of 6.96±0.2°, 10.31±0.2°, 14.95±0.2°.

5. The compound of Formula (II) as represented by the following formula, or the crystal form C or D thereof according to claim 4, wherein the crystal form C of the compound of Formula (II) has an XRPD pattern with characteristic diffraction peaks at 2θ angles of 5.90±0.2°, 6.52±0.2°, 8.00±0.2°, 12.28±0.2°, 15.06±0.2°, 15.84±0.2°, 21.22±0.2°, 26.82±0.2°, and further has an XRPD pattern analysis data as shown in the following table:

| No. | 2θ (±0.2°) |
|---|---|
| 1 | 5.896 |
| 2 | 6.525 |
| 3 | 7.65 |
| 4 | 8.004 |
| 5 | 10.647 |
| 6 | 11.615 |
| 7 | 12.285 |
| 8 | 12.834 |
| 9 | 13.977 |
| 10 | 15.064 |
| 11 | 15.837 |
| 12 | 17.036 |
| 13 | 17.888 |
| 14 | 19.762 |
| 15 | 21.218 |
| 16 | 21.871 |
| 17 | 24.566 |
| 18 | 25.44 |
| 19 | 26.031 |
| 20 | 26.822 |
| 21 | 31.148 |
| 22 | 32.943 |
| 23 | 37.924 |
| 24 | 38.066 | further, the crystal form C of the compound of Formula (II) has an XRPD pattern as shown in FIG. 7;

further, the crystal form C of the compound of Formula (II) has a differential scanning calorimetry (DSC) curve with an endothermic peak at 193.754° C.±3° C. and an endothermic peak at 235.53° C.±3° C., and further has a DSC pattern as shown in FIG. 8;

further, the crystal form C of the compound of Formula (II) has a thermogravimetric analysis (TGA) curve with a weight loss of 5.000% at 117.79° C.±3° C., and a weight loss of up to 12.377% at 222.15° C.±3° C., and further has a TGA pattern as shown in FIG. 9;

further, for the crystal form C of the compound of Formula (II), the compound of Formula (II) has a structure as represented by Compound II-1:

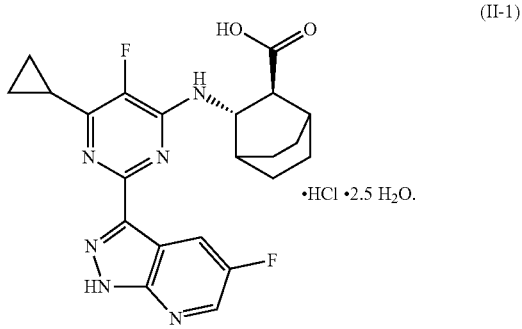 [SMILES: O=C(O)[C@H]1C2CCC(CC2)[C@@H]1Nc1nc(-c2n[nH]c3ncc(F)cc23)nc(C2CC2)c1F]

(II-1)

·HCl ·2.5 H₂O.

6. The compound of Formula (II), or the crystal form C or D thereof according to claim 4, wherein the crystal form D of the compound of Formula (II) has an XRPD pattern with characteristic diffraction peaks at 2θ angles of 6.96±0.2°, 9.44±0.2°, 10.31±0.2°, 14.95±0.2°, 17.38±0.2°, 20.67±0.2°, 21.89±0.2°, 22.72±0.2°, and further has an XRPD pattern analysis data as shown in the following table:

| No. | 2θ (±0.2°) |
|---|---|
| 1 | 6.958 |
| 2 | 9.444 |
| 3 | 10.311 |
| 4 | 12.128 |
| 5 | 12.819 |
| 6 | 14.946 |
| 7 | 15.322 |
| 8 | 15.892 |
| 9 | 16.268 |
| 10 | 17.376 |
| 11 | 18.698 |
| 12 | 19.72 |
| 13 | 20.666 |
| 14 | 21.89 |
| 15 | 22.717 |
| 16 | 23.806 |
| 17 | 24.63 |
| 18 | 24.907 |
| 19 | 25.792 |
| 20 | 26.704 |
| 21 | 27.452 |
| 22 | 28.202 |
| 23 | 28.595 |
| 24 | 28.966 |
| 25 | 30.843 |
| 26 | 31.198 |
| 27 | 31.75 |
| 28 | 32.584 |
| 29 | 34.359 |
| 30 | 35.168 |
| 31 | 35.816 |
| 32 | 37.196 |
| 33 | 37.569 | further, the crystal form D of the compound of Formula (II) has an XRPD pattern as shown in FIG. 10;

further, the crystal form D of the compound of Formula (II) has a differential scanning calorimetry (DSC) curve with an endothermic peak at 193.68° C.±3° C., and further has a DSC pattern as shown in FIG. 11;

further, the crystal form D of the compound of Formula (II) has a thermogravimetric analysis (TGA) curve with a weight loss of 0.231% at 78.99° C.±3° C. and a weight loss of up to 5.826% at 198.74° C.±3° C., and further has a TGA pattern as shown in FIG. 12;

further, for the crystal form D of the compound of Formula (II), the compound of Formula (II) is represented by Compound II-2:

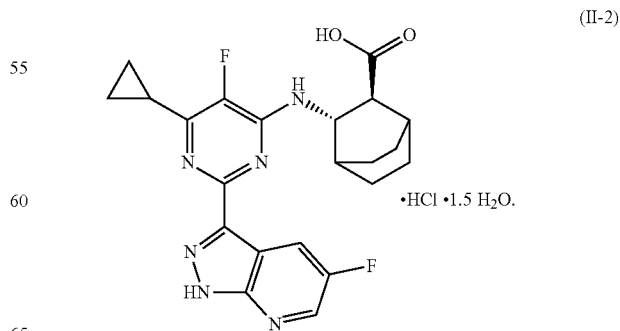

(II-2)

·HCl ·1.5 H₂O.

7. A Compound 3 represented by the following formula, or a crystal form E thereof,

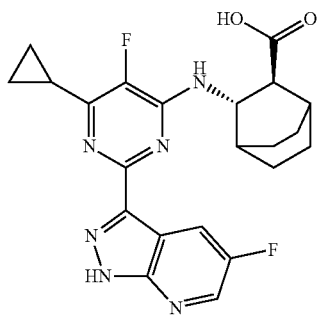

Compound 3

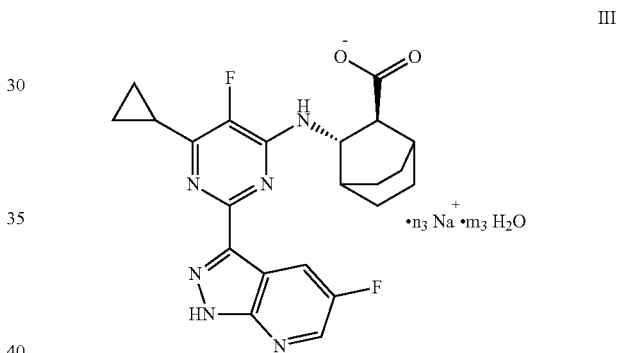

wherein the crystal form E of Compound 3 has an X-ray powder diffraction (XRPD) pattern with characteristic diffraction peaks at 2θ angles of 8.10±0.2°, 9.60±0.2°, 22.97±0.2°.

8. The Compound 3 or the crystal form E thereof according to claim 7, wherein the crystal form E of Compound 3 has an XRPD pattern with characteristic diffraction peaks at 2θ angles of 8.10±0.2°, 9.60±0.2°, 16.09±0.2°, 17.61±0.2°, 18.42±0.2°, 22.97±0.2°, 23.58±0.2°, 25.14±0.2°, and further has an XRPD pattern analysis data as shown in the following table:

| No. | 2θ (±0.2°) |
| --- | --- |
| 1 | 8.104 |
| 2 | 9.599 |
| 3 | 9.833 |
| 4 | 11.066 |
| 5 | 11.712 |
| 6 | 12.487 |
| 7 | 12.978 |
| 8 | 13.707 |
| 9 | 15.753 |
| 10 | 16.093 |
| 11 | 16.722 |
| 12 | 16.996 |
| 13 | 17.612 |
| 14 | 18.415 |
| 15 | 19.227 |
| 16 | 19.542 |
| 17 | 20.077 |
| 18 | 20.351 |
| 19 | 21.513 |
| 20 | 22.204 |
| 21 | 22.595 |
| 22 | 22.974 |
| 23 | 23.254 |
| 24 | 23.585 |
| 25 | 24.199 |
| 26 | 24.907 |
| 27 | 25.143 |
| 28 | 25.595 |
| 29 | 26.073 |
| 30 | 26.765 |
| 31 | 27.252 |
| 32 | 27.507 |
| 33 | 27.885 |
| 34 | 28.417 |
| 35 | 28.932 |
| 36 | 29.564 |
| 37 | 30.076 |
| 38 | 31.055 |
| 39 | 31.673 |
| 40 | 32.263 |
| 41 | 32.539 |
| 42 | 33.116 |
| 43 | 34.414 |
| 44 | 35.364 |
| 45 | 35.634 |
| 46 | 35.735 |
| 47 | 37.236 |
| 48 | 37.851 |
| 49 | 38.124 |
| 50 | 38.953 | further, the crystal form E of Compound 3 has an XRPD pattern as shown in FIG. 13;

further, the crystal form E of Compound 3 has a differential scanning calorimetry (DSC) curve with a starting point of an endothermic peak at 258.27° C.±3° C., and further has a DSC pattern as shown in FIG. 14;

further, the crystal form E of Compound 3 has a thermogravimetric analysis (TGA) curve with a weight loss of 0.905% at 121.35° C.±3° C., and further has a TGA pattern as shown in FIG. 15.

9. A compound of Formula (III) as represented by the following formula, or a crystal form F or G thereof:

III

·$n_3$ Na$^+$ ·$m_3$ H$_2$O wherein,
$n_3$ is selected from 1;
$m_3$ is selected from 0, 0.5, 1, 1.5, 2, 2.5, 3, 3.5 and 4;
wherein the crystal form F of the compound of Formula (III) has an X-ray powder diffraction (XRPD) pattern with characteristic diffraction peaks at 2θ angles of 6.47±0.2°, 9.11±0.2°, 9.90±0.2°;
wherein the crystal form G of the compound of Formula (III) has an X-ray powder diffraction (XRPD) pattern with characteristic diffraction peaks at 2θ angles of 6.23±0.2°, 7.20±0.2°, 14.30±0.2°.

10. The compound of Formula (III), or the crystal form F or G thereof according to claim 9, wherein the crystal form F of the compound of Formula (III) has an XRPD pattern with characteristic diffraction peaks at 2θ angles of 6.47±0.2°, 9.11±0.2°, 9.90±0.2°, 15.85±0.2°, 16.28±0.2°, 19.40±0.2°, 20.37±0.2°, 24.10±0.2°, and further has an XRPD pattern analysis data as shown in the following table:

| No. | 2θ (±0.2°) |
| --- | --- |
| 1 | 4.477 |
| 2 | 6.467 |
| 3 | 9.109 |
| 4 | 9.895 |

| No. | 2θ (±0.2°) |
|---|---|
| 5 | 11.189 |
| 6 | 11.779 |
| 7 | 12.899 |
| 8 | 14.473 |
| 9 | 15.34 |
| 10 | 15.854 |
| 11 | 16.285 |
| 12 | 17.416 |
| 13 | 17.885 |
| 14 | 18.693 |
| 15 | 19.402 |
| 16 | 20.374 |
| 17 | 21.377 |
| 18 | 22.221 |
| 19 | 23.235 |
| 20 | 23.59 |
| 21 | 24.099 |
| 22 | 24.707 |
| 23 | 26.368 |
| 24 | 27.608 |
| 25 | 28.159 |
| 26 | 29.862 |
| 27 | 31.77 |
| 28 | 32.327 |
| 29 | 35.334 |
| 30 | 37.497 | further the crystal form F of the compound of Formula (III) has an XRPD pattern as shown in FIG. 16;

further, the crystal form F of the compound of Formula (III) has a differential scanning calorimetry (DSC) curve with an endothermic peak at 78.73° C.±3° C., a starting point of an endothermic peak at 222.37° C.±3° C., and an exothermic peak at 245.01° C.±3° C., and further has a DSC pattern as shown in FIG. 17;

further, the crystal form F of the compound of Formula (III) has a thermogravimetric analysis (TGA) curve with a weight loss of 1.192% at 39.57° C.±3° C., a weight loss of up to 3.683% at 81.27° C.±3° C. and a weight loss of up to 6.023% at 199.63° C.±3° C., and further has a TGA pattern as shown in FIG. 18;

further, for the crystal form F of the compound of Formula (III), the compound of Formula (III) is represented by Compound III-1:

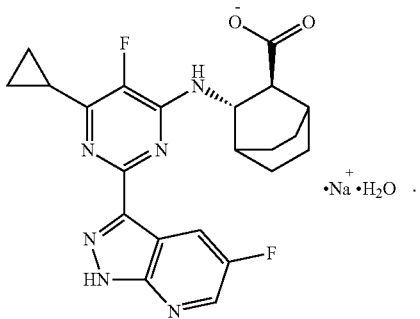

(III-1)

11. The compound of Formula (III), or the crystal form F or G thereof according to claim 9, wherein the crystal form G of the compound of Formula (III) has an XRPD pattern with characteristic diffraction peaks at 2θ angles of 6.23±0.2°, 7.20±0.2°, 7.81±0.2°, 11.22±0.2°, 12.38±0.2°, 14.30±0.2°, 15.90±0.2°, 18.97±0.2°, and further has an XRPD pattern analysis data as shown in the following table:

| No. | 2θ (±0.2°) |
|---|---|
| 1 | 4.806 |
| 2 | 5.933 |
| 3 | 6.23 |
| 4 | 6.527 |
| 5 | 7.197 |
| 6 | 7.809 |
| 7 | 9.5 |
| 8 | 9.9 |
| 9 | 10.182 |
| 10 | 11.217 |
| 11 | 11.785 |
| 12 | 12.383 |
| 13 | 12.915 |
| 14 | 13.327 |
| 15 | 13.918 |
| 16 | 14.298 |
| 17 | 14.634 |
| 18 | 15.617 |
| 19 | 15.895 |
| 20 | 16.439 |
| 21 | 16.737 |
| 22 | 17.071 |
| 23 | 17.555 |
| 24 | 17.931 |
| 25 | 18.177 |
| 26 | 18.969 |
| 27 | 19.921 |
| 28 | 20.173 |
| 29 | 21.065 |
| 30 | 21.984 |
| 31 | 22.401 |
| 32 | 22.679 |
| 33 | 22.816 |
| 34 | 23.528 |
| 35 | 25.319 |
| 36 | 26.107 |
| 37 | 27.315 |
| 38 | 28.063 |
| 39 | 28.753 |
| 40 | 30.273 |
| 41 | 30.905 |
| 42 | 31.454 |
| 43 | 33.08 |
| 44 | 33.43 |
| 45 | 35.019 |
| 46 | 35.402 |
| 47 | 36.172 |
| 48 | 36.721 |
| 49 | 37.749 |
| 50 | 38.508 | further, the crystal form G of the compound of Formula (III) has an XRPD pattern as shown in FIG. 19;

further, the crystal form G of the compound of Formula (III) has a differential scanning calorimetry (DSC) curve with an endothermic peak at 70.13° C.±3° C., and further has a DSC pattern as shown in FIG. 20;

further, the crystal form G of the compound of Formula (III) has a thermogravimetric analysis (TGA) curve as shown in FIG. 21;

further, the crystal form G of the compound of Formula (III), the compound of Formula (III) is represented by Compound III-1:

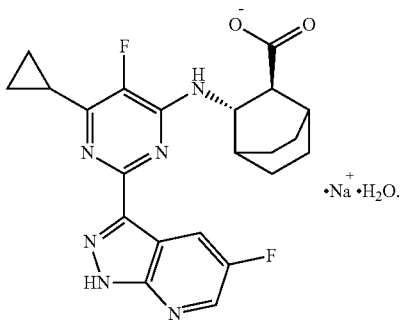

(III-1)

12. A compound of Formula (IV) as represented by the following formula, or a crystal form H, K, I or J thereof:

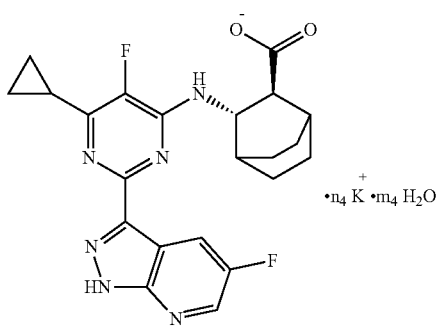

(IV)

wherein,
$n_4$ is selected from 1;
$m_4$ is selected from 0, 0.5, 1, 1.5, 2, 2.5, 3, 3.5 and 4;
wherein the crystal form H of the compound of Formula (IV) has an X-ray powder diffraction (XRPD) pattern with characteristic diffraction peaks at 2θ angles of 4.71±0.2°, 5.56±0.2°, 18.16±0.2°;
wherein the crystal form K of the compound of Formula (IV) has an XRPD pattern with characteristic diffraction peaks at 2θ angles of 4.83±0.2°, 7.39±0.2°, 14.80±0.2°;
wherein the crystal form I of the compound of Formula (IV) has an XRPD pattern with characteristic diffraction peaks at 2θ angles of 4.89±0.2°, 6.19±0.2°, 7.45±0.2°;
wherein the crystal form J of the compound of Formula (IV) has an XRPD pattern with characteristic diffraction peaks at 2θ angles of 4.97±0.2°, 16.33±0.2°, 23.92±0.2°.

13. The compound of Formula (IV), or the crystal form H, K, I or J thereof according to claim 12, wherein the crystal form H of the compound of Formula (IV) has an XRPD pattern with characteristic diffraction peaks at 2θ angles of 4.71±0.2°, 5.56±0.2°, 7.98±0.2°, 8.97±0.2°, 18.16±0.2°, 22.42±0.2°, 26.37±0.2°, 27.10±0.2°, and further has an XRPD pattern analysis data as shown in the following table:

| No. | 2θ (±0.2°) |
|---|---|
| 1 | 4.71 |
| 2 | 5.559 |
| 3 | 7.984 |
| 4 | 8.971 |
| 5 | 12.543 |
| 6 | 13.361 |
| 7 | 14.352 |
| 8 | 15.186 |
| 9 | 16.125 |
| 10 | 16.743 |
| 11 | 18.163 |
| 12 | 18.518 |
| 13 | 19.151 |
| 14 | 19.659 |
| 15 | 19.921 |
| 16 | 22.42 |
| 17 | 23.268 |
| 18 | 26.367 |
| 19 | 27.097 |
| 20 | 27.574 |
| 21 | 28.355 |
| 22 | 29.319 |
| 23 | 30.035 |
| 24 | 32.92 | further, the crystal form H of the compound of Formula (IV) has an XRPD pattern as shown in FIG. 22;
further, the crystal form H of the compound of Formula (IV) has a differential scanning calorimetry (DSC) curve with an endothermic peak at 141.17° C.±3° C., an endothermic peak at 243.06° C.±3° C., and an exothermic peak at 257.74° C.±3° C., and further has a DSC pattern as shown in FIG. 23;
further, the crystal form H of the compound of Formula (IV) has a thermogravimetric analysis (TGA) curve with a weight loss of 1.328% at 73.74±3° C., a weight loss of up to 4.986% at 207.43° C.±3° C., and a weight loss of up to 5.627% at 249.40° C.±3° C., and further has a TGA pattern as shown in FIG. 24.

14. The compound of Formula (IV), or the crystal form H, K, I or J thereof according to claim 12, wherein the crystal form K of the compound of Formula (IV) has an XRPD pattern with characteristic diffraction peaks at 2θ angles of 4.83±0.2°, 7.39±0.2°, 11.61±0.2°, 14.81±0.2°, 16.19±0.2°, 18.50±0.2°, 19.29±0.2°, 20.86±0.2°, and further has an XRPD pattern analysis data as shown in the following table:

| No. | 2θ (±0.2°) |
|---|---|
| 1 | 4.827 |
| 2 | 5.989 |
| 3 | 7.393 |
| 4 | 9.814 |
| 5 | 11.14 |
| 6 | 11.612 |
| 7 | 14.204 |
| 8 | 14.473 |
| 9 | 14.807 |
| 10 | 15.042 |
| 11 | 16.187 |
| 12 | 18.499 |
| 13 | 18.933 |
| 14 | 19.287 |
| 15 | 19.66 |
| 16 | 20.863 |
| 17 | 22.48 |
| 18 | 23.292 |
| 19 | 26.245 |
| 20 | 26.504 |
| 21 | 27.841 |

-continued

| No. | 2θ (±0.2°) |
|---|---|
| 22 | 28.477 |
| 23 | 34.215 | further, the crystal form K of the compound of Formula (IV) has an XRPD pattern as shown in FIG. 31;

further, the crystal form K of the compound of Formula (IV) has a differential scanning calorimetry (DSC) curve as shown in FIG. 32;

further, the crystal form K of the compound of Formula (IV) has a thermogravimetric analysis (TGA) curve with a weight loss of 3.442% at 83.69° C.±3° C. and a weight loss of up to 4.947% at 183.76° C.±3° C., and further has a TGA pattern as shown in FIG. 33.

15. The compound of Formula (IV), or the crystal form H, K, I or J thereof according to claim 12, wherein the crystal form I of the compound of Formula (IV) has an XRPD pattern with characteristic diffraction peaks at 2θ angles of 4.89±0.2°, 6.19±0.2°, 7.45±0.2°, 16.23±0.2°, 18.28±0.2°, 18.95±0.2°, 26.31±0.2°, 27.04±0.2°, and further has an XRPD pattern analysis data as shown in the following table:

| No. | 2θ (±0.2°) |
|---|---|
| 1 | 4.889 |
| 2 | 6.188 |
| 3 | 7.452 |
| 4 | 9.717 |
| 5 | 9.968 |
| 6 | 12.225 |
| 7 | 14.529 |
| 8 | 15.022 |
| 9 | 15.814 |
| 10 | 16.226 |
| 11 | 18.28 |
| 12 | 18.954 |
| 13 | 19.822 |
| 14 | 20.923 |
| 15 | 21.821 |
| 16 | 22.575 |
| 17 | 23.384 |
| 18 | 26.307 |
| 19 | 27.035 |
| 20 | 28.12 |
| 21 | 29.98 |
| 22 | 35.366 |
| 23 | 38.437 | further, the crystal form I of the compound of Formula (IV) has an XRPD pattern as shown in FIG. 25;

further, the crystal form I of the compound of Formula (IV) has a differential scanning calorimetry (DSC) curve with an endothermic peak at 86.86° C.±3° C., and further has a DSC pattern as shown in FIG. 26;

further, the crystal form I of the compound of Formula (IV) has a thermogravimetric analysis (TGA) curve with a weight loss of 1.298% at 46.81° C.±3° C., a weight loss of up to 3.607% at 89.20° C.±3° C. and a weight loss of up to 4.641% at 169.65° C.±3° C., and further has a TGA pattern as shown in FIG. 27.

16. The compound of Formula (IV), or the crystal form H, K, I or J thereof according to claim 12, the crystal form J of the compound of Formula (IV) has an XRPD pattern with characteristic diffraction peaks at 2θ angles of 4.97±0.2°, 6.19±0.2°, 16.33±0.2°, 19.15±0.2°, 19.84±0.2°, 21.02±0.2°, 22.68±0.2°, 23.92±0.2°, and further has an XRPD pattern analysis data as shown in the following table:

| No. | 2θ (±0.2°) |
|---|---|
| 1 | 4.967 |
| 2 | 6.191 |
| 3 | 9.94 |
| 4 | 11.773 |
| 5 | 14.569 |
| 6 | 15.043 |
| 7 | 15.739 |
| 8 | 16.326 |
| 9 | 18.378 |
| 10 | 19.148 |
| 11 | 19.839 |
| 12 | 21.021 |
| 13 | 21.728 |
| 14 | 22.679 |
| 15 | 23.448 |
| 16 | 23.922 |
| 17 | 26.328 |
| 18 | 27.037 |
| 19 | 28.043 |
| 20 | 28.682 |
| 21 | 29.895 |
| 22 | 30.996 |
| 23 | 34.409 |
| 24 | 39.37 | further, the crystal form J of the compound of Formula (IV) has an XRPD pattern as shown in FIG. 28;

further, the crystal form J of the compound of Formula (IV) has a differential scanning calorimetry (DSC) curve with an endothermic peak at 61.29° C.±3° C., an endothermic peak at 86.40° C.±3° C., and an endothermic peak at 151.50° C.±3° C., and further has a DSC pattern as shown in FIG. 29;

further, the crystal form J of the compound of Formula (IV) has a thermogravimetric analysis (TGA) curve with a weight loss of 3.412% at 220.12° C.±3° C., and further has a TGA pattern as shown in FIG. 30.

17. The compound of Formula (IV), or the crystal form H, K, I or J thereof according to claim 12,
wherein, for the crystal form H or K of the compound of Formula (IV), the compound of Formula (IV) is represented by Compound (IV-1):

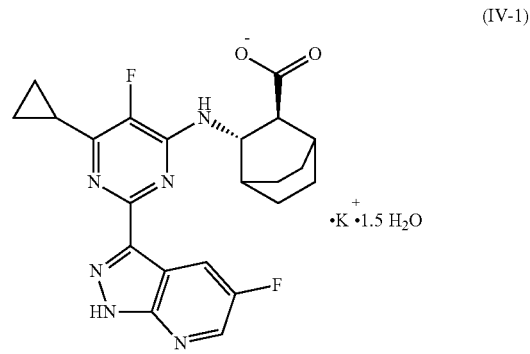

(IV-1)

wherein, for the crystal form I or J of the compound of Formula (IV), the compound of Formula (IV) is represented by Compound (IV-2):

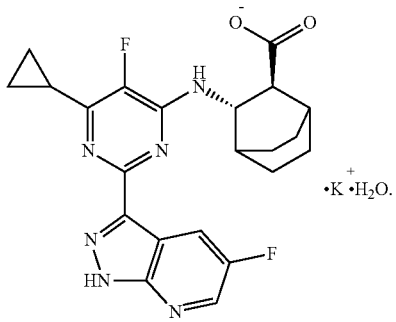

(IV-2)

18. A compound of Formula (V) represented by the following formula, or a crystal form L thereof:

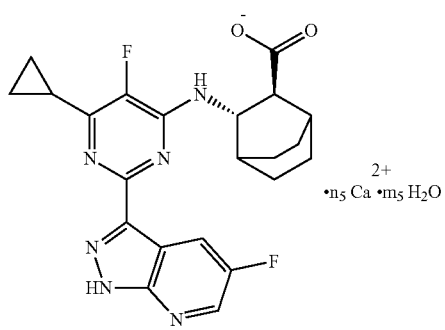

(V)

wherein,
$n_5$ is selected from 0.5 and 1;
$m_5$ is selected from 0, 0.5, 1, 1.5, 2, 2.5, 3, 3.5 and 4;
wherein the crystal form L of the compound of Formula (V) has an X-ray powder diffraction (XRPD) pattern with characteristic diffraction peaks at 2θ angles of 10.39±0.2°, 18.04±0.2°, 20.31±0.2°.

19. The compound of Formula (V), or the crystal form L thereof according to claim 18, wherein the crystal form L of the compound of Formula (V) has an XRPD pattern with characteristic diffraction peaks at 2θ angles of 7.91±0.2°, 10.39±0.2°, 14.18±0.2°, 16.01±0.2°, 16.47±0.2°, 18.04±0.2°, 20.31±0.2°, 21.91±0.2°, and further has an XRPD pattern analysis data as shown in the following table:

| No. | 2θ (±0.2°) |
| --- | --- |
| 1 | 7.906 |
| 2 | 10.393 |
| 3 | 11.788 |
| 4 | 13.626 |
| 5 | 14.18 |
| 6 | 15.049 |
| 7 | 15.774 |
| 8 | 16.012 |
| 9 | 16.466 |
| 10 | 17.164 |
| 11 | 18.044 |
| 12 | 19.86 |
| 13 | 20.311 |
| 14 | 20.829 |
| 15 | 21.91 |
| 16 | 22.538 |
| 17 | 23.194 |
| 18 | 24.59 |
| 19 | 25.124 |
| 20 | 25.417 |
| 21 | 25.894 |
| 22 | 26.35 |
| 23 | 28.104 |
| 24 | 28.632 |
| 25 | 29.821 |
| 26 | 31.395 |
| 27 | 32.48 |
| 28 | 34.257 |
| 29 | 35.399 |
| 30 | 39.383 | further, the crystal form L of the compound of Formula (V) has an XRPD pattern as shown in FIG. 34;

further, the crystal form L of the compound of Formula (V) has a differential scanning calorimetry (DSC) curve with an endothermic peak at 168.08° C.±3° C., an endothermic peak at 204.17° C.±3° C., and further has a DSC pattern as shown in FIG. 35;

further, the crystal form L of the compound of Formula (V) has a thermogravimetric analysis (TGA) curve with a weight loss of 0.830% at 80.19° C.±3° C., a weight loss of up to 3.058% at 149.87° C.±3° C., and a weight loss of up to 4.648% at 201.25° C.±3° C., and further has a TGA pattern as shown in FIG. 36;

further, for the crystal form L of the compound of Formula (V), the compound of Formula (V) is represented by Compound V-1:

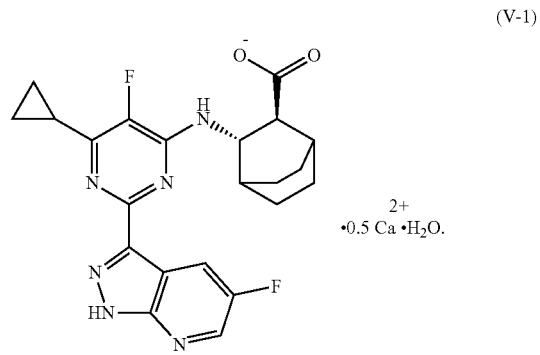 [SMILES: O=C(O)[C@H]1C2CCC(CC2)[C@@H]1Nc1nc(-c2n[nH]c3ncc(F)cc23)nc(C2CC2)c1F]

(V-1)

20. A method of treating an influenza virus-associated disease, comprising administering a therapeutically effective amount of the compound or the crystal form thereof according to claims 1 to a subject in need thereof.

21. A method of treating an influenze virus-associated disease, comprising administering a therapeutically effective amount of the compound or the crystal form thereof according to claim 4 to a subject in need thereof.

22. A method of treating an influenza virus-associated disease, comprising administering a therapeutically effective amount of the compound or the crystal form thereof according to claim 7 to a subject in need thereof.

23. A method of treating an influenza virus-associated disease, comprising administering a therapeutically effective amount of the compound or the crystal form thereof according to claim 9 to a subject in need thereof.

24. A method of treating an influenza virus-associated disease, comprising administering a therapeutically effective amount of the compound or the crystal form thereof according to claim 12 to a subject in need thereof.

25. A method of treating an influenza virus-associated disease, comprising administering a therapeutically effective amount of the compound or the crystal form thereof according to claim 18 to a subject in need thereof.

* * * * *